(12) United States Patent
Fares et al.

(10) Patent No.: US 8,114,836 B2
(45) Date of Patent: *Feb. 14, 2012

(54) LONG-ACTING VETERINARY POLYPEPTIDES AND METHODS OF PRODUCING AND ADMINISTERING SAME

(75) Inventors: Fuad Fares, Hourfish Village (IL); Udi Eyal Fima, Beer-Sheva (IL)

(73) Assignee: Prolor Biotech Ltd., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/401,755

(22) Filed: Mar. 11, 2009

(65) Prior Publication Data

US 2009/0286733 A1 Nov. 19, 2009

Related U.S. Application Data

(63) Continuation of application No. 11/702,156, filed on Feb. 5, 2007, now abandoned.

(60) Provisional application No. 60/764,761, filed on Feb. 3, 2006.

(51) Int. Cl.
| | |
|---|---|
| A61K 38/22 | (2006.01) |
| A61K 38/24 | (2006.01) |
| A61K 38/27 | (2006.01) |
| C07K 14/575 | (2006.01) |
| C07K 14/59 | (2006.01) |
| C07K 14/61 | (2006.01) |

(52) U.S. Cl. ........................ 514/5.1; 530/399
(58) Field of Classification Search ........................ None
See application file for complete search history.

(56) References Cited

U.S. PATENT DOCUMENTS

| | | | |
|---|---|---|---|
| 5,177,193 | A | 1/1993 | Boime |
| 5,759,818 | A | 6/1998 | Boime et al. |
| 5,792,460 | A | 8/1998 | Boime |
| 6,238,890 | B1 | 5/2001 | Boime et al. |
| 6,514,729 | B1 | 2/2003 | Bentzien |
| 7,094,566 | B2 | 8/2006 | Medlock et al. |
| 7,141,547 | B2 | 11/2006 | Rosen et al. |
| 7,371,373 | B2 | 5/2008 | Shirley et al. |
| 7,553,940 | B2 | 6/2009 | Fares et al. |
| 7,553,941 | B2 | 6/2009 | Fares et al. |
| 2003/0216313 | A1 | 11/2003 | Lustbader et al. |
| 2005/0234221 | A1 | 10/2005 | Medlock et al. |
| 2007/0184530 | A1 | 8/2007 | Fares et al. |
| 2007/0190611 | A1 | 8/2007 | Fares et al. |
| 2009/0130060 | A1 | 5/2009 | Weimer et al. |

FOREIGN PATENT DOCUMENTS

| | | |
|---|---|---|
| WO | WO 2005/080544 | 9/2005 |
| WO | WO2005/080544 | 9/2005 |

OTHER PUBLICATIONS

Schein, Catherine H. The shape of the messenger: using protein structure information to design novel cytokine-based therapeutics. ABSTRACT; Current Pharmaceutical Design, vol. 8/No. 24, pp. 2113-2129 (2002).*
Fares et al. Designing a long-acting human growth hormone (hGH) by fusing the carboxy-terminal peptide of human chorionic gonadotropin B-subunit to the coding sequence of hGH. Endocrinology, vol. 151(9):4410-4417 (Sep. 2010).*
Furuhashi, M. et al; 'Fusing the Carboxy-terminal Peptide of the Chorionic Gonadotropin (CG) β-Subunit to the Common a-Subunit: Retention of O-linked Glycosylation and Enhanced in vivo Bioactivity of Chimeric Human CG', Molecular Endocrinology, 1995, vol. 9, No. 1, pp. 54-63.
Furuhashi, M. et al, 'Processing of O-linked Glycosylation in the Chimera Consisting of a-Subunit and Carboxyl-terminal Peptide of the Human Chorionic Gonadotropin β-Subunit is affected by Dimer Formation with Follicle-stimulating Hormone β-Subunit', Endocrine Journal 2004, vol. 51, No. 1, pp. 53-59.
Amirizahdeh et al. "Transient and stable expression of biologically active recombinant B-domain-deleted human factor VIII in mammalian cells" Journal Of Sciences Islamic Republic Of Iran; 16(2):103-112. Spring, 2005.
Boissel et al. "Erythropoietin structure-function relationships. Mutant proteins that test a model of tertiary structure" The Journal of Biological Chemistry, 268, 15983-15993, Jul. 25, 1993.
Fares et al. "Growth Hormone (GH) Retardation of Muscle Damage due to Immobilization in Old Rats Possible Intervention with a New Long-Acting Recombinant GH" Ann NY Acad Sci. 786:430-43. Jun. 15, 1996.
Houdebine et al. "The methods to generate transgenic animals and to control transgene expression" Journal of Biotechnology vol. 98, Issues 2-3, pp. 145-160, Sep. 25, 2002.
Ngo et al. "Computational Complexity, Protein Structure Prediction, and the Levinthal Paradox" The protein folding problem and tertiary structure prediction. pp. 433-440 and 492-495. (1994).
Phillips et al. "The challenge of gene therapy and DNA delivery" Journal of Pharmacy and Pharmacology vol. 53, Issue 9, pp. 1169-1174, Sep. 2001, Abstract.
Unalp et al. "Factor VII deficiency associated with Valproate treatment" Pediatrics International vol. 50, Issue 3, pp. 403-405, Jun. 2008.
Wells. "Additivity of mutational effects in proteins" Biochemistry, 29 (37), pp. 8509-8517. (1990).
Schein CH et al. "The shape of the messenger: using protein structure information to design novel cytokine-based therapeutics" Curr Pharm Des. 8(24):2113-29,(2002), Abstract.
Barker et al. "An immunomagnetic-base method for the purification of ovarian cancer cells from patient-derived ascites". Gynecologic Oncology 82, 57-63 (2001).
Freshney et al. Culture of animal cells: A manual of basic technique, New York, 1983, p. 4.
Su et al. "Curcumin Inhibits Human Lung Cell Carcinoma Cancer Tumour Growth in a Murine Xenograft Model" Phytother. Res 24:189-191, 2010.

* cited by examiner

*Primary Examiner* — Elizabeth C Kemmerer
*Assistant Examiner* — Regina M DeBerry
(74) *Attorney, Agent, or Firm* — Pearl Cohen Zedek Latzer, LLP; Mark S. Cohen

(57) ABSTRACT

A polypeptide and polynucleotides comprising at least two carboxy-terminal peptides (CTP) of chorionic gonadotrophin attached to a non-human peptide-of-interest are disclosed. Pharmaceutical compositions comprising the non-human polypeptides and polynucleotides of the invention and methods of using both human and non-human polypeptides and polynucleotides are also disclosed.

16 Claims, 6 Drawing Sheets

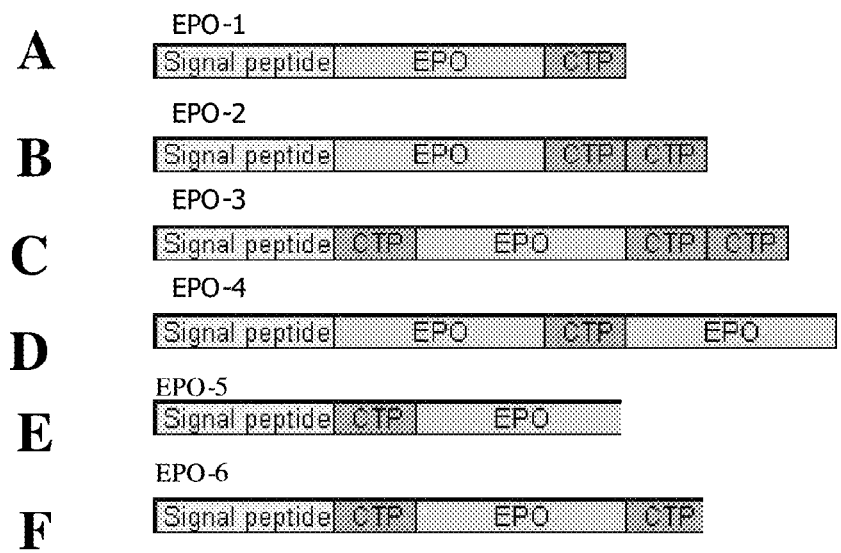
Figures 1A-F
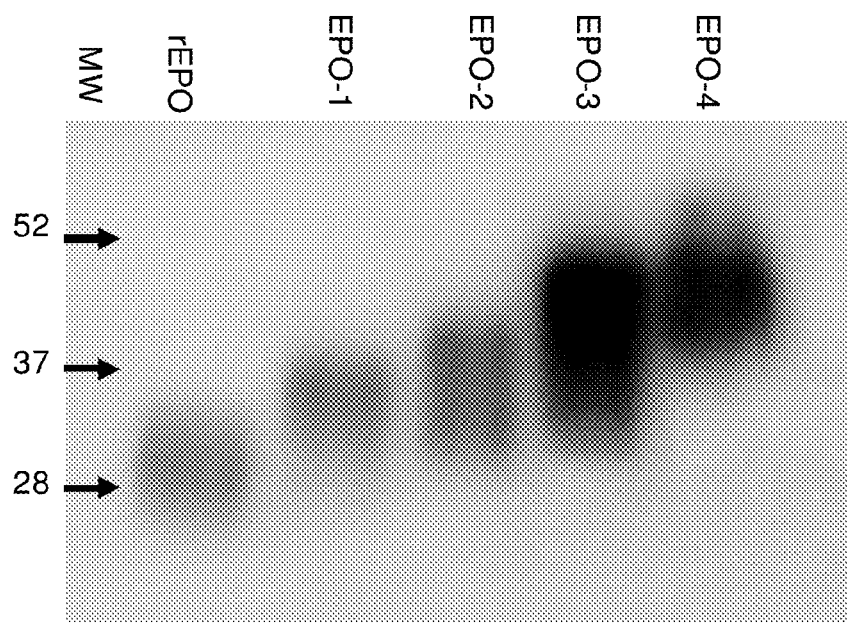
Figure 2

LONG-ACTING VETERINARY POLYPEPTIDES AND METHODS OF PRODUCING AND ADMINISTERING SAME

CROSS REFERENCE TO RELATED APPLICATIONS

This application is a divisional application of U.S. patent application Ser. No. 12/401,755 filed Mar. 11, 2009, which is a continuation of U.S. patent application Ser. No. 11/702,156 filed on Feb. 5, 2007, now abandoned, which claims the benefit of U.S. Provisional Application Ser. No. 60/764,761, filed Feb. 3, 2006, all of which are hereby incorporated by reference herein in their entirety.

FIELD OF INVENTION

A polypeptide and polynucleotides encoding same comprising at least two carboxy-terminal peptides (CTP) of chorionic gonadotrophin attached to a peptide-of-interest are disclosed. Pharmaceutical compositions comprising the polypeptides and polynucleotides of the invention and methods of using same are also disclosed.

BACKGROUND OF THE INVENTION

Polypeptides are susceptible to denaturation or enzymatic degradation in the blood, liver or kidney. Accordingly, polypeptides typically have short circulatory half-lives of several hours. Because of their low stability, peptide drugs are usually delivered in a sustained frequency so as to maintain an effective plasma concentration of the active peptide. Moreover, since peptide drugs are usually administered by infusion, frequent injection of peptide drugs causes considerable discomfort to a subject. Thus, there is a need for technologies that will prolong the half-lives of therapeutic polypeptides while maintaining a high pharmacological efficacy thereof. Such desired peptide drugs should also meet the requirements of enhanced serum stability, high activity and a low probability of inducing an undesired immune response when injected into a subject.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight polypeptide drugs, physiological clearance mechanisms such as renal filtration can make the maintenance of therapeutic levels of a drug unfeasible because of cost or frequency of the required dosing regimen. Conversely, a long serum half-life is undesirable where a drug or its metabolites have toxic side effects.

SUMMARY OF THE INVENTION

In one embodiment, the present invention provides a polypeptide comprising at least two chorionic gonadotrophin carboxy terminal peptides (CTPs) attached to a non-human peptide of interest.

In another embodiment, the present invention provides a polypeptide comprising a first chorionic gonadotrophin CTP attached to the amino terminus of a non-human peptide of interest and a second chorionic gonadotrophin CTP attached to the carboxy terminus of a polypeptide sequence of interest.

In another embodiment, the present invention provides a polypeptide comprising two chorionic gonadotrophin CTPs attached to the carboxy terminus of a non-human peptide of interest.

In another embodiment, the present invention provides a polypeptide comprising a first chorionic gonadotrophin CTP attached to the amino terminus of non-human peptide of interest, and a second and third chorionic gonadotrophin CTP attached to the carboxy terminus of a polypeptide sequence of interest.

In another embodiment, the present invention provides a polypeptide comprising at least three chorionic gonadotrophin CTPs attached to a non-human peptide of interest.

In another embodiment, the present invention provides a polynucleotide comprising a sequence encoding a polypeptide comprising at least two chorionic gonadotrophin CTPs attached to a non-human peptide of interest.

In another embodiment, the present invention provides a polynucleotide comprising a sequence encoding a first chorionic gonadotrophin CTP attached to the amino terminus of non-human peptide of interest and a second chorionic gonadotrophin CTP attached to the carboxy terminus of a polypeptide sequence of interest.

In another embodiment, the present invention provides a polynucleotide comprising a sequence encoding two chorionic gonadotrophin CTPs attached to the carboxy terminus of non-human peptide of interest.

In another embodiment, the present invention provides a polynucleotide comprising a sequence encoding a first chorionic gonadotrophin CTP attached to the amino terminus of non-human peptide of interest, and a second and third chorionic gonadotrophin CTP attached to the carboxy terminus of a polypeptide sequence of interest.

In another embodiment, the present invention provides a polynucleotide comprising a sequence encoding at least three chorionic gonadotrophin CTPs attached to a non-human peptide of interest.

In another embodiment, the present invention provides a method of treating or reducing the incidence associated with a growth, weight-related, or metabolic condition in a non-human subject, comprising administering to a subject a therapeutically effective amount of CTP-GH, thereby treating a non-human subject having a growth, weight-related, or metabolic condition. In another embodiment, the GH peptide is a non-human GH peptide. In another embodiment, the GH peptide is a human peptide. Each possibility represents a separate embodiment of the present invention.

In another embodiment, the present invention provides a method of improving a biological half-life of a non-human peptide of interest, comprising the step of attaching at least two chorionic gonadotrophin CTP sequences to the non-human peptide of interest, thereby improving a biological half-life of a non-human peptide of interest.

In another embodiment, the present invention provides a method of administering a peptide of interest to a non-human subject in need thereof, comprising the step of attaching at least two chorionic gonadotrophin CTP sequences to the peptide of interest, thereby administering a peptide of interest to a non-human subject in need thereof. In another embodiment, the peptide of interest is a non-human peptide of interest. In another embodiment, the peptide of interest is a human peptide of interest. Each possibility represents a separate embodiment of the present invention.

BRIEF DESCRIPTION OF THE DRAWINGS

FIGS. 1A-1F are diagrams illustrating six EPO-CTP constructs.
FIG. 1A is a diagram of the polypeptide of SEQ ID NO: 1.
FIG. 1B is a diagram of the polypeptide of SEQ ID NO: 2.
FIG. 1C is a diagram of the polypeptide of SEQ ID NO: 3.

FIG. 1D is a diagram of the polypeptide of SEQ ID NO: 4.
FIG. 1E is a diagram of the polypeptide of SEQ ID NO: 5.
FIG. 1F is a diagram of the polypeptide of SEQ ID NO: 6.
FIG. 2 is a photograph illustrating the expression of the EPO-CTP variants from transfected DG44 cells. Final test samples from transfected cells were prepared as described under "sample preparation" and run on SDS/PAGE. Proteins were detected by Western blot.

DETAILED DESCRIPTION OF THE INVENTION

Figure 3:
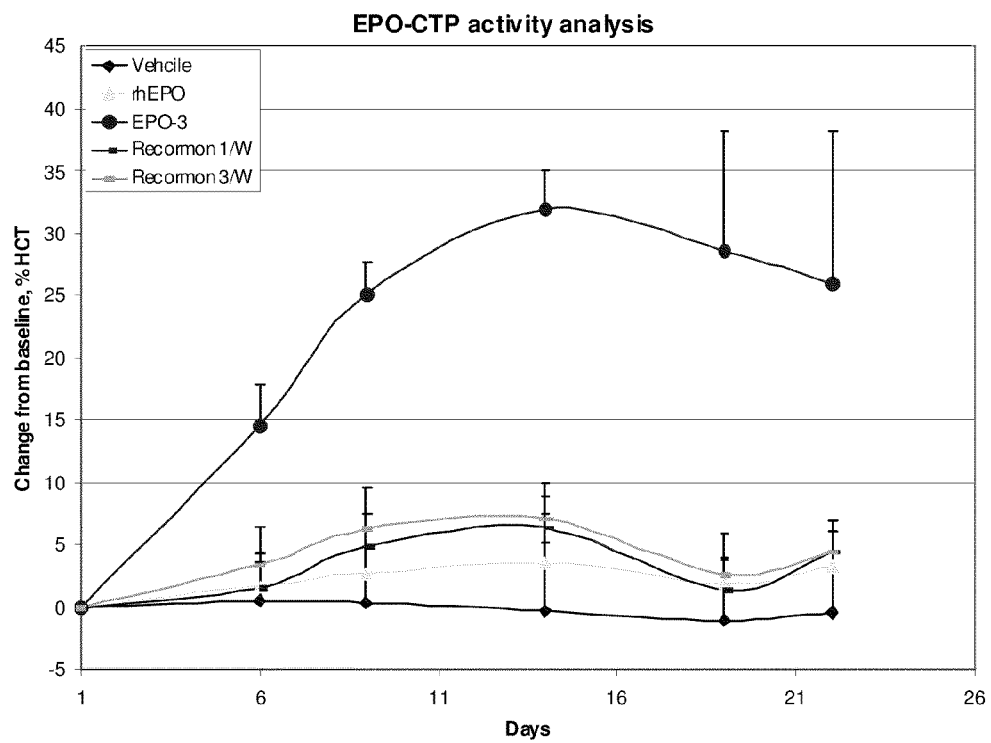
FIG. 3 is a graph illustrating the in vivo bioactivity of recombinant hEPO derivatives and EPO-3 (SEQ ID NO: 3). ICR mice (n=7/group) received a single i.v. injection/week (15 µg/kg) for three weeks of EPO-3, rhEPO-WT (SEQ ID NO: 16), Recormon® (Commercial EPO) or Recormon® (5 µg/kg) 3 times a week. Control animals were injected i.v. with PBS. Blood samples were collected three times a week and haematocrit levels were detected. Each point represents the group average of haematocrit (%)±SE.

In one embodiment, the present invention describes long-acting polypeptides and methods of producing and using same. In another embodiment, long-acting polypeptides comprise carboxy terminal peptide (CTP) of human Chorionic Gonadotropin (hCG). In another embodiment, CTP acts as a protectant against degradation of proteins or peptides derived therefrom. In another embodiment, CTP extends circulatory half-lives of proteins or peptides derived therefrom. In some embodiments, CTP enhances the potency of proteins or peptides derived therefrom.

In another embodiment, "CTP peptide," "carboxy terminal peptide," and "CTP sequence" are used interchangeably herein. In another embodiment, the carboxy terminal peptide is a full-length CTP. In another embodiment, the carboxy terminal peptide is a truncated CTP. Each possibility represents a separate embodiment of the present invention.

In another embodiment, "signal sequence" and "signal peptide" are used interchangeably herein. In another embodiment, "sequence" when in reference to a polynucleotide can refer to a coding portion. Each possibility represents a separate embodiment of the present invention.

In another embodiment, "peptide of interest" and "polypeptide sequence of interest" are used interchangeably herein. In another embodiment, the peptide of interest is a full length protein. In another embodiment, the peptide of interest is a protein fragment. Each possibility represents a separate embodiment of the present invention.

In another embodiment, a polypeptide comprising at least two carboxy-terminal peptide (CTP) sequences of chorionic gonadotrophin attached to a polypeptide sequence of interest, wherein a first CTP sequence of the at least two CTP sequences is attached to the amino terminus of the polypeptide sequence of interest and a second CTP sequence of the at least two CTP sequences is attached to the carboxy terminus of the polypeptide sequence of interest is provided. In another embodiment, the carboxy-terminal peptide (CTP) sequence is of human chorionic gonadotrophin.

In another embodiment, the carboxy-terminal peptide (CTP) is attached to the polypeptide sequence of interest via a linker. In another embodiment, the linker which connects the CTP sequence to the polypeptide sequence of interest is a covalent bond. In another embodiment, the linker which connects the CTP sequence to the polypeptide sequence of interest is a peptide bond. In another embodiment, the linker which connects the CTP sequence to the polypeptide sequence of interest is a substituted peptide bond.

The phrase "polypeptide sequence of interest" refers, in another embodiment, to any polypeptide sequence, such as one comprising a biological activity. In another embodiment, the peptide is glycosylated. In another embodiment, the peptide is non-glycosylated. Examples of polypeptides which benefit from an extension in their circulatory half-life include, but are not limited to erythropoietin (EPO), interferon, human growth hormone (hGH) and glucagon-like peptide-1 (GLP-1).

In another embodiment, the carboxy terminal peptide (CTP) of human Chorionic Gonadotropin (hCG) is fused to a protein. In another embodiment, the carboxy terminal peptide (CTP) of human hCG is fused to a glycoprotein. In another embodiment, the carboxy terminal peptide (CTP) of hCG is fused to a glycoprotein hormone. In another embodiment, the CTP of hCG is fused to a peptide derived from a glycoprotein hormone. In some embodiments, glycoprotein hormones comprise EPO, FSH, or TSH and peptides derived therefrom.

In some embodiments, CTP sequences at both the amino terminal end of a polypeptide and at the carboxy terminal end of the polypeptide provide enhanced protection against degradation of a protein. In some embodiments, CTP sequences at both the amino terminal end of a polypeptide and at the carboxy terminal end of the polypeptide provide an extended half-life to the attached protein.

In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced protection against degradation of a protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide an extended half-life to the attached protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced activity of the attached protein.

In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide enhanced protection against degradation of the attached protein. In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide an extended half-life to the attached protein. In some embodiments, a CTP sequence at the amino terminal end of a polypeptide, a CTP sequence at the carboxy terminal end of the polypeptide, and at least one additional CTP sequence attached in tandem to the CTP sequence at the amino terminus provide enhanced activity the attached protein.

In another embodiment, the carboxy terminal peptide (CTP) peptide of the present invention comprises the amino acid sequence from amino acid 112 to position 145 of human chorionic gonadotrophin, as set forth in SEQ ID NO: 17. In another embodiment, the CTP sequence of the present invention comprises the amino acid sequence from amino acid 118 to position 145 of human chorionic gonadotropin, as set forth in SEQ ID NO: 18. In another embodiment, the CTP sequence also commences from any position between positions 112-118 and terminates at position 145 of human chorionic gonadotrophin. In some embodiments, the CTP sequence peptide is 28, 29, 30, 31, 32, 33 or 34 amino acids long and commences at position 112, 113, 114, 115, 116, 117 or 118 of the CTP amino acid sequence.

In another embodiment, the CTP peptide is a variant of chorionic gonadotrophin CTP which differs from the native CTP by 1-5 conservative amino acid substitutions as described in U.S. Pat. No. 5,712,122. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions. In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof.

In another embodiment, the CTP peptide DNA sequence of the present invention is at least 70% homologous to the native CTP DNA sequence or a peptide thereof. In another embodiment, the CTP peptide DNA sequence of the present invention is at least 80% homologous to the native CTP DNA sequence or a peptide thereof. In another embodiment, the CTP peptide DNA sequence of the present invention is at least 90% homologous to the native CTP DNA sequence or a peptide thereof. In another embodiment, the CTP peptide DNA sequence of the present invention is at least 95% homologous to the native CTP DNA sequence or a peptide thereof.

In one embodiment, at least one of the chorionic gonadotrophin CTP amino acid sequences is truncated. In another embodiment, both of the chorionic gonadotrophin CTP amino acid sequences are truncated. In another embodiment, 2 of the chorionic gonadotrophin CTP amino acid sequences are truncated. In another embodiment, 2 or more of the chorionic gonadotrophin CTP amino acid sequences are truncated. In another embodiment, all of the chorionic gonadotrophin CTP amino acid sequences are truncated. In one embodiment, the truncated CTP comprises the first 10 amino acids of SEQ ID NO: 43. In one embodiment, the truncated CTP comprises the first 11 amino acids of SEQ ID NO: 43. In one embodiment, the truncated CTP comprises the first 12 amino acids of SEQ ID NO: 43. In one embodiment, the truncated CTP comprises the first 13 amino acids of SEQ ID NO: 43. In one embodiment, the truncated CTP comprises the first 14 amino acids of SEQ ID NO: 43. In one embodiment, the truncated CTP comprises the first 15 amino acids of SEQ ID NO: 43. In one embodiment, the truncated CTP comprises the first 16 amino acids of SEQ ID NO: 43. In one embodiment, the truncated CTP comprises the last 14 amino acids of SEQ ID NO: 43.

In one embodiment, at least one of the chorionic gonadotrophin CTP amino acid sequences is glycosylated. In another embodiment, both of the chorionic gonadotrophin CTP amino acid sequences are glycosylated. In another embodiment, 2 of the chorionic gonadotrophin CTP amino acid sequences are glycosylated. In another embodiment, 2 or more of the chorionic gonadotrophin CTP amino acid sequences are glycosylated. In another embodiment, all of the chorionic gonadotrophin CTP amino acid sequences are glycosylated. In one embodiment, the CTP sequence of the present invention comprises at least one glycosylation site. In one embodiment, the CTP sequence of the present invention comprises 2 glycosylation sites. In one embodiment, the CTP sequence of the present invention comprises 3 glycosylation sites. In one embodiment, the CTP sequence of the present invention comprises 4 glycosylation sites. Each possibility represents a separate embodiment of the present invention.

As provided herein, attachment of CTP sequences to both the amino and carboxy termini of the EPO protein results in increased potency at stimulating erythropoiesis (FIGS. 3-5 and Table 6 of Example 4), as compared to recombinant EPO and other combinations of EPO and CTP. In some embodiments, an EPO attached to three CTP sequences does not impair binding to its receptor as evidenced in Table 4 of Example 3, which demonstrates that EPO attached to three CTP sequences is equally effective at stimulating proliferation of TF-1 cells as wild-type EPO.

In some embodiments, "homology" according to the present invention also encompasses deletions, insertions, or substitution variants, including an amino acid substitution thereof, and biologically active polypeptide fragments thereof. In one embodiment, the substitution variant comprises a substitution of the glycine in position 104 of the erythropoietin amino acid sequence with a serine (SEQ ID NO: 22).

In another embodiment, the methods of the present invention provide an EPO peptide having additionally at least one CTP amino acid peptide on the N-terminus and at least one CTP amino acid peptide on the C-terminus for the treatment of anemia. In another embodiment, the methods of the present invention provide an EPO peptide having additionally one CTP amino acid peptide on the N-terminus and two CTP amino acid peptides on the C-terminus for the treatment of anemia. In another embodiment, the methods of the present invention provide an EPO peptide set forth in SEQ ID NO: 1 having additionally at least one CTP amino acid peptide on the N-terminus for the treatment of anemia. In another embodiment, the methods of the present invention provide an EPO peptide set forth in SEQ ID NO: 1 having additionally at least one CTP amino acid peptide on the N-terminus and at least one additional CTP amino acid peptide on the C-terminus for the treatment of anemia. In another embodiment, the methods of the present invention provide an EPO peptide set forth in SEQ ID NO: 2 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 3 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 4 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 5 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 6 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 16 having additionally at least one CTP amino acid peptide on the N-terminus and at least one CTP amino acid peptide on the C-terminus for the treatment of anemia. In another embodiment, the methods of the present invention provide an EPO peptide set forth in SEQ ID NO: 22 having additionally at least one CTP amino acid peptide on the N-terminus and at least one CTP amino acid peptide on the C-terminus for the treatment of anemia.

In another embodiment, the methods of the present invention provide a nucleic acid sequence encoding an EPO peptide having additionally at least one CTP amino acid peptide on the N-terminus and at least one CTP amino acid peptide on the C-terminus for the treatment of anemia. In another embodiment, the methods of the present invention provide a nucleic acid sequence encoding an EPO peptide having additionally one CTP amino acid peptide on the N-terminus and two CTP amino acid peptides on the C-terminus for the treatment of anemia. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for the treatment of anemia. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for the treatment of anemia.

In another embodiment, the methods of the present invention provide an EPO peptide having additionally at least one CTP amino acid peptide on the N-terminus and at least one CTP amino acid peptide on the C-terminus for inhibiting anemia. In another embodiment, the methods of the present invention provide an EPO peptide having additionally one CTP amino acid peptide on the N-terminus and two CTP amino acid peptides on the C-terminus for inhibiting anemia. In another embodiment, the methods of the present invention provide an EPO peptide set forth in SEQ ID NO: 1 having additionally at least one CTP amino acid peptide on the N-terminus for inhibiting anemia. In another embodiment, the methods of the present invention provide an EPO peptide set forth in SEQ ID NO: 1 having additionally at least one CTP amino acid peptide on the N-terminus and at least one additional CTP amino acid peptide on the C-terminus for inhibiting anemia. In another embodiment, the methods of the present invention provide an EPO peptide set forth in SEQ ID NO: 2 having additionally at least one CTP amino acid peptide on the N-terminus and at least one CTP amino acid peptide on the C-terminus for inhibiting anemia. In another embodiment, the methods of the present invention provide an EPO peptide set forth in SEQ ID NO: 3 having additionally at least one CTP amino acid peptide on the N-terminus and at least one CTP amino acid peptide on the C-terminus for inhibiting anemia. In another embodiment, the methods of the present invention provide an EPO peptide set forth in SEQ ID NO: 4 having additionally at least one CTP amino acid peptide on the N-terminus and at least one CTP amino acid peptide on the C-terminus for inhibiting anemia. In another embodiment, the methods of the present invention provide an EPO peptide set forth in SEQ ID NO: 5 having additionally at least one CTP amino acid peptide on the N-terminus and at least one CTP amino acid peptide on the C-terminus for inhibiting anemia. In another embodiment, the methods of the present invention provide an EPO peptide set forth in SEQ ID NO: 6 having additionally at least one CTP amino acid peptide on the N-terminus and at least one CTP amino acid peptide on the C-terminus for inhibiting anemia. In another embodiment, the methods of the present invention provide an EPO peptide set forth in SEQ ID NO: 16 having additionally at least one CTP amino acid peptide on the N-terminus and at least one CTP amino acid peptide on the C-terminus for inhibiting anemia. In another embodiment, the methods of the present invention provide an EPO peptide set forth in SEQ ID NO: 22 having additionally at least one CTP amino acid peptide on the N-terminus and at least one CTP amino acid peptide on the C-terminus for inhibiting anemia.

In another embodiment, the methods of the present invention provide a nucleic acid sequence encoding an EPO peptide having additionally at least one CTP amino acid peptide on the N-terminus and at least one CTP amino acid peptide on the C-terminus for inhibiting anemia. In another embodiment, the methods of the present invention provide a nucleic acid sequence encoding an EPO peptide having one CTP amino acid peptide on the N-terminus and two CTP amino acid peptides on the C-terminus for inhibiting anemia. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for inhibiting anemia. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for inhibiting anemia.

In another embodiment, the methods of the present invention provide an EPO peptide having additionally at least one CTP amino acid peptide on the N-terminus and at least one CTP amino acid peptide on the C-terminus for the treatment of tumor-associated anemia. In another embodiment, the methods of the present invention provide an EPO peptide having additionally one CTP amino acid peptide on the N-terminus and two CTP amino acid peptides on the C-terminus for the treatment of tumor-associated anemia. In another embodiment, the methods of the present invention provide an EPO peptide set forth in SEQ ID NO: 1 having additionally at least one CTP amino acid peptide on the N-terminus for the treatment of tumor-associated anemia. In another embodiment, the methods of the present invention provide an EPO peptide set forth in SEQ ID NO: 1 having additionally at least one CTP amino acid peptide on the N-terminus and at least additional one CTP amino acid peptide on the C-terminus for the treatment of tumor-associated anemia. In another embodiment, the methods of the present invention provide an EPO peptide set forth in SEQ ID NO: 2 having additionally at least one CTP amino acid peptide on the N-terminus and at least one CTP amino acid peptide on the C-terminus for the treatment of tumor-associated anemia. In another embodiment, the methods of the present invention provide an EPO peptide set forth in SEQ ID NO: 3 having additionally at least one CTP amino acid peptide on the N-terminus and at least one CTP amino acid peptide on the C-terminus for the treatment of tumor-associated anemia. In another embodiment, the methods of the present invention provide an EPO peptide set forth in SEQ ID NO: 4 having additionally at least one CTP amino acid peptide on the N-terminus and at least one CTP amino acid peptide on the C-terminus for the treatment of tumor-associated anemia. In another embodiment, the methods of the present invention provide an EPO peptide set forth in SEQ ID NO: 5 having additionally at least one CTP amino acid peptide on the N-terminus and at least one CTP amino acid peptide on the C-terminus for the treatment of tumor-associated anemia. In another embodiment, the methods of the present invention provide an EPO peptide set forth in SEQ ID NO: 6 having additionally at least one CTP amino acid peptide on the N-terminus and at least one CTP amino acid peptide on the C-terminus for the treatment of tumor-associated anemia. In another embodiment, the methods of the present invention provide an EPO peptide set forth in SEQ ID NO: 16 having additionally at least one CTP amino acid peptide on the N-terminus and at least one CTP amino acid peptide on the C-terminus for the treatment of tumor-associated anemia. In another embodiment, the methods of the present invention provide an EPO peptide set forth in SEQ ID NO: 22 having additionally at least one CTP amino acid peptide on the N-terminus and at least one CTP amino acid peptide on the C-terminus for the treatment of tumor-associated anemia.

In another embodiment, the methods of the present invention provide a nucleic acid sequence encoding an EPO peptide having additionally at least one CTP amino acid peptide on the N-terminus and at least one CTP amino acid peptide on the C-terminus for the treatment of tumor-associated anemia. In another embodiment, the methods of the present invention provide a nucleic acid sequence encoding an EPO peptide having additionally one CTP amino acid peptide on the N-terminus and two CTP amino acid peptides on the C-terminus for the treatment of tumor-associated anemia. In another embodiment, the methods of the present invention provide a nucleic acid sequence as set forth in SEQ ID NO: 20 encoding an EPO peptide having additionally one CTP amino acid peptide on the N-terminus and at least one CTP amino acid peptide on the C-terminus for the treatment of tumor-associated anemia. In another embodiment, the methods of the present invention provide a nucleic acid sequence as set forth in SEQ ID NO: 21 encoding an EPO peptide having additionally one CTP amino acid peptide on the N-terminus and two CTP amino acid peptides on the C-terminus for the treatment of tumor-associated anemia.

In another embodiment, the methods of the present invention provide an EPO peptide having additionally at least one CTP amino acid peptide on the N-terminus and at least one CTP amino acid peptide on the C-terminus for inhibiting tumor-associated anemia. In another embodiment, the methods of the present invention provide an EPO peptide having additionally one CTP amino acid peptide on the N-terminus and two CTP amino acid peptides on the C-terminus for inhibiting tumor-associated anemia. In another embodiment, the methods of the present invention provide an EPO peptide set forth in SEQ ID NO: 1 having additionally at least one CTP amino acid peptide on the N-terminus for inhibiting tumor-associated anemia. In another embodiment, the methods of the present invention provide an EPO peptide set forth in SEQ ID NO: 1 having additionally at least one CTP amino acid peptide on the N-terminus and at least additional one CTP amino acid peptide on the C-terminus for inhibiting tumor-associated anemia. In another embodiment, the methods of the present invention provide an EPO peptide set forth in SEQ ID NO: 2 having additionally at least one CTP amino acid peptide on the N-terminus and at least one CTP amino acid peptide on the C-terminus for inhibiting tumor-associated anemia. In another embodiment, the methods of the present invention provide an EPO peptide set forth in SEQ ID NO: 3 having additionally at least one CTP amino acid peptide on the N-terminus and at least one CTP amino acid peptide on the C-terminus for inhibiting tumor-associated anemia. In another embodiment, the methods of the present invention provide an EPO peptide set forth in SEQ ID NO: 4 having additionally at least one CTP amino acid peptide on the N-terminus and at least one CTP amino acid peptide on the C-terminus for inhibiting tumor-associated anemia. In another embodiment, the methods of the present invention provide an EPO peptide set forth in SEQ ID NO: 5 having additionally at least one CTP amino acid peptide on the N-terminus and at least one CTP amino acid peptide on the C-terminus for inhibiting tumor-associated anemia. In another embodiment, the methods of the present invention provide an EPO peptide set forth in SEQ ID NO: 6 having additionally at least one CTP amino acid peptide on the N-terminus and at least one CTP amino acid peptide on the C-terminus for inhibiting tumor-associated anemia. In another embodiment, the methods of the present invention provide an EPO peptide set forth in SEQ ID NO: 16 having additionally at least one CTP amino acid peptide on the N-terminus and at least one CTP amino acid peptide on the C-terminus for inhibiting tumor-associated anemia. In another embodiment, the methods of the present invention provide an EPO peptide set forth in SEQ ID NO: 22 having additionally at least one CTP amino acid peptide on the N-terminus and at least one CTP amino acid peptide on the C-terminus for inhibiting tumor-associated anemia.

In another embodiment, the methods of the present invention provide a nucleic acid sequence encoding an EPO peptide having additionally at least one CTP amino acid peptide on the N-terminus and at least one CTP amino acid peptide on the C-terminus for inhibiting tumor-associated anemia. In another embodiment, the methods of the present invention provide a nucleic acid sequence encoding an EPO peptide having additionally one CTP amino acid peptide on the N-terminus and two CTP amino acid peptides on the C-terminus for inhibiting tumor-associated anemia. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for inhibiting tumor-associated anemia. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for inhibiting tumor-associated anemia.

In another embodiment, the methods of the present invention provide an EPO peptide having additionally at least one CTP amino acid peptide on the N-terminus and at least one CTP amino acid peptide on the C-terminus for the treatment of tumor hypoxia. In another embodiment, the methods of the present invention provide an EPO peptide having additionally one CTP amino acid peptide on the N-terminus and two CTP amino acid peptides on the C-terminus for the treatment of tumor hypoxia. In another embodiment, the methods of the present invention provide an EPO peptide set forth in SEQ ID NO: 1 having additionally at least one CTP amino acid peptide on the N-terminus for the treatment of tumor hypoxia. In another embodiment, the methods of the present invention provide an EPO peptide set forth in SEQ ID NO: 1 having additionally at least one CTP amino acid peptide on the N-terminus and at least additional one CTP amino acid peptide on the C-terminus for the treatment of tumor hypoxia. In another embodiment, the methods of the present invention provide an EPO peptide set forth in SEQ ID NO: 2 having additionally at least one CTP amino acid peptide on the N-terminus and at least one CTP amino acid peptide on the C-terminus for the treatment of tumor hypoxia. In another embodiment, the methods of the present invention provide an EPO peptide set forth in SEQ ID NO: 3 having additionally at least one CTP amino acid peptide on the N-terminus and at least one CTP amino acid peptide on the C-terminus for the treatment of tumor hypoxia. In another embodiment, the methods of the present invention provide an EPO peptide set forth in SEQ ID NO: 4 having additionally at least one CTP amino acid peptide on the N-terminus and at least one CTP amino acid peptide on the C-terminus for the treatment of tumor hypoxia. In another embodiment, the methods of the present invention provide an EPO peptide set forth in SEQ ID NO: 5 having additionally at least one CTP amino acid peptide on the N-terminus and at least one CTP amino acid peptide on the C-terminus for the treatment of tumor hypoxia. In another embodiment, the methods of the present invention provide an EPO peptide set forth in SEQ ID NO: 6 having additionally at least one CTP amino acid peptide on the N-terminus and at least one CTP amino acid peptide on the C-terminus for the treatment of tumor hypoxia. In another embodiment, the methods of the present invention provide an EPO peptide set forth in SEQ ID NO: 16 having additionally at least one CTP amino acid peptide on the N-terminus and at least one CTP amino acid peptide on the C-terminus for the treatment of tumor hypoxia. In another embodiment, the methods of the present invention provide an EPO peptide set forth in SEQ ID NO: 22 having additionally at least one CTP amino acid peptide on the N-terminus and at least one CTP amino acid peptide on the C-terminus for the treatment of tumor hypoxia.

In another embodiment, the methods of the present invention provide a nucleic acid sequence encoding an EPO peptide having additionally at least one CTP amino acid peptide on the N-terminus and at least one CTP amino acid peptide on the C-terminus for the treatment of tumor hypoxia. In another embodiment, the methods of the present invention provide a nucleic acid sequence encoding an EPO peptide having additionally one CTP amino acid peptide on the N-terminus and two CTP amino acid peptides on the C-terminus for the treatment of tumor hypoxia. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for the treatment of tumor hypoxia. In another embodiment, the methods of the present invention provide a nucleic acid sequence as set forth in SEQ ID NO: 21 encoding an EPO peptide having additionally one CTP amino acid peptide on the N-terminus and two CTP amino acid peptides on the C-terminus for the treatment of tumor hypoxia.

In another embodiment, the methods of the present invention provide an EPO peptide having additionally at least one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide an EPO peptide having additionally one CTP amino acid peptide on the N-terminus and two CTP amino acid peptides on the C-terminus for the treatment of chronic infections such as HIV, inflammatory bowel disease, or septic episodes. In another embodiment, the methods of the present invention provide an EPO peptide set forth in SEQ ID NO: 1 having additionally at least one CTP amino acid peptide on the N-terminus for the treatment of chronic infections such as HIV, inflammatory bowel disease, or septic episodes. In another embodiment, the methods of the present invention provide an EPO peptide set forth in SEQ ID NO: 1 having additionally at least one CTP amino acid peptide on the N-terminus and at least additional one CTP amino acid peptide on the C-terminus for the treatment of chronic infections such as HIV, inflammatory bowel disease, or septic episodes. In another embodiment, the methods of the present invention provide an EPO peptide set forth in SEQ ID NO: 2 having additionally at least one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide an EPO peptide set forth in SEQ ID NO: 3 having additionally at least one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide an EPO peptide set forth in SEQ ID NO: 4 having additionally at least one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide an EPO peptide set forth in SEQ ID NO: 5 having additionally at least one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide an EPO peptide set forth in SEQ ID NO: 6 having additionally at least one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide an EPO peptide set forth in SEQ ID NO: 16 having additionally at least one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide an EPO peptide set forth in SEQ ID NO: 22 having additionally at least one CTP amino acid peptide on the N-terminus and at least one CTP amino acid peptide on the C-terminus for the treatment of chronic infections such as HIV, inflammatory bowel disease, or septic episodes.

In another embodiment, the methods of the present invention provide a nucleic acid sequence encoding an EPO peptide having additionally at least one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide a nucleic acid sequence encoding an EPO peptide having additionally one CTP amino acid peptide on the N-terminus and two CTP amino acid peptides on the C-terminus for the treatment of chronic infections such as HIV, inflammatory bowel disease, or septic episodes. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for the treatment of chronic infections such as HIV, inflammatory bowel disease, or septic episodes. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for the treatment of chronic infections such as HIV, inflammatory bowel disease, or septic episodes.

In another embodiment, the methods of the present invention provide an EPO peptide having additionally at least one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide an EPO peptide having additionally one CTP amino acid peptide on the N-terminus and two CTP amino acid peptides on the C-terminus for inhibiting chronic infections such as HIV, inflammatory bowel disease, or septic episodes. In another embodiment, the methods of the present invention provide an EPO peptide set forth in SEQ ID NO: 1 having additionally at least one CTP amino acid peptide on the N-terminus for inhibiting chronic infections such as HIV, inflammatory bowel disease, or septic episodes. In another embodiment, the methods of the present invention provide an EPO peptide set forth in SEQ ID NO: 1 having additionally at least one CTP amino acid peptide on the N-terminus and at least additional one CTP amino acid peptide on the C-terminus for inhibiting chronic infections such as HIV, inflammatory bowel disease, or septic episodes. In another embodiment, the methods of the present invention provide an EPO peptide set forth in SEQ ID NO: 2 having additionally at least one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide an EPO peptide set forth in SEQ ID NO: 3 having additionally at least one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide an EPO peptide set forth in SEQ ID NO: 4 having additionally at least one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide an EPO peptide set forth in SEQ ID NO: 5 having additionally at least one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide an EPO peptide set forth in SEQ ID NO: 6 having additionally at least one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide an EPO peptide set forth in SEQ ID NO: 16 having additionally at least one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide an EPO peptide set forth in SEQ ID NO: 22 having additionally at least one CTP amino acid peptide on the N-terminus and at least one CTP amino acid peptide on the C-terminus for inhibiting chronic infections such as HIV, inflammatory bowel disease, or septic episodes.

In another embodiment, the methods of the present invention provide a nucleic acid sequence encoding an EPO peptide having additionally at least one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide a nucleic acid sequence encoding an EPO peptide having one CTP amino acid peptide on the N-terminus and two CTP amino acid peptides on the C-terminus for inhibiting chronic infections such as HIV, inflammatory bowel disease, or septic episodes. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for inhibiting chronic infections such as HIV, inflammatory bowel disease, or septic episodes. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for inhibiting chronic infections such as HIV, inflammatory bowel disease, or septic episodes.

In another embodiment, the methods of the present invention provide an EPO peptide having additionally at least one CTP amino acid peptide on the N-terminus and at least one CTP amino acid peptide on the C-terminus for the treatment of fatigue syndrome following cancer chemotherapy. In another embodiment, the methods of the present invention provide an EPO peptide having additionally one CTP amino acid peptide on the N-terminus and two CTP amino acid peptides on the C-terminus for the treatment of fatigue syndrome following cancer chemotherapy. In another embodiment, the methods of the present invention provide an EPO peptide set forth in SEQ ID NO: 1 having additionally at least one CTP amino acid peptide on the N-terminus for the treatment of fatigue syndrome following cancer chemotherapy. In another embodiment, the methods of the present invention provide an EPO peptide set forth in SEQ ID NO: 1 having additionally at least one CTP amino acid peptide on the N-terminus and at least additional one CTP amino acid peptide on the C-terminus for the treatment of fatigue syndrome following cancer chemotherapy. In another embodiment, the methods of the present invention provide an EPO peptide set forth in SEQ ID NO: 2 having additionally at least one CTP amino acid peptide on the N-terminus and at least one CTP amino acid peptide on the C-terminus for the treatment of fatigue syndrome following cancer chemotherapy. In another embodiment, the methods of the present invention provide an EPO peptide set forth in SEQ ID NO: 3 having additionally at least one CTP amino acid peptide on the N-terminus and at least one CTP amino acid peptide on the C-terminus for the treatment of fatigue syndrome following cancer chemotherapy. In another embodiment, the methods of the present invention provide an EPO peptide set forth in SEQ ID NO: 4 having additionally at least one CTP amino acid peptide on the N-terminus and at least one CTP amino acid peptide on the C-terminus for the treatment of fatigue syndrome following cancer chemotherapy. In another embodiment, the methods of the present invention provide an EPO peptide set forth in SEQ ID NO: 5 having additionally at least one CTP amino acid peptide on the N-terminus and at least one CTP amino acid peptide on the C-terminus for the treatment of fatigue syndrome following cancer chemotherapy. In another embodiment, the methods of the present invention provide an EPO peptide set forth in SEQ ID NO: 6 having additionally at least one CTP amino acid peptide on the N-terminus and at least one CTP amino acid peptide on the C-terminus for the treatment of fatigue syndrome following cancer chemotherapy. In another embodiment, the methods of the present invention provide an EPO peptide set forth in SEQ ID NO: 16 having additionally at least one CTP amino acid peptide on the N-terminus and at least one CTP amino acid peptide on the C-terminus for the treatment of fatigue syndrome following cancer chemotherapy. In another embodiment, the methods of the present invention provide an EPO peptide set forth in SEQ ID NO: 22 having additionally at least one CTP amino acid peptide on the N-terminus and at least one CTP amino acid peptide on the C-terminus for the treatment of fatigue syndrome following cancer chemotherapy.

In another embodiment, the methods of the present invention provide a nucleic acid sequence encoding an EPO peptide having additionally at least one CTP amino acid peptide on the N-terminus and at least one CTP amino acid peptide on the C-terminus for the treatment of fatigue syndrome following cancer chemotherapy. In another embodiment, the methods of the present invention provide a nucleic acid sequence encoding an EPO peptide having additionally one CTP amino acid peptide on the N-terminus and two CTP amino acid peptides on the C-terminus for the treatment of fatigue syndrome following cancer chemotherapy. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for the treatment of fatigue syndrome following cancer chemotherapy. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for the treatment of fatigue syndrome following cancer chemotherapy.

In another embodiment, the methods of the present invention provide an EPO peptide having additionally at least one CTP amino acid peptide on the N-terminus and at least one CTP amino acid peptide on the C-terminus for improving stem cell engraftment. In another embodiment, the methods of the present invention provide an EPO peptide having additionally one CTP amino acid peptide on the N-terminus and two CTP amino acid peptides on the C-terminus for improving stem cell engraftment. In another embodiment, the methods of the present invention provide an EPO peptide set forth in SEQ ID NO: 1 having additionally at least one CTP amino acid peptide on the N-terminus for improving stem cell engraftment. In another embodiment, the methods of the present invention provide an EPO peptide set forth in SEQ ID NO: 1 having additionally at least one CTP amino acid peptide on the N-terminus and at least additional one CTP amino acid peptide on the C-terminus for improving stem cell engraftment. In another embodiment, the methods of the present invention provide an EPO peptide set forth in SEQ ID NO: 2 having additionally at least one CTP amino acid peptide on the N-terminus and at least one CTP amino acid peptide on the C-terminus for improving stem cell engraftment. In another embodiment, the methods of the present invention provide an EPO peptide set forth in SEQ ID NO: 3 having additionally at least one CTP amino acid peptide on the N-terminus and at least one CTP amino acid peptide on the C-terminus for improving stem cell engraftment. In another embodiment, the methods of the present invention provide an EPO peptide set forth in SEQ ID NO: 4 having additionally at least one CTP amino acid peptide on the N-terminus and at least one CTP amino acid peptide on the C-terminus for improving stem cell engraftment. In another embodiment, the methods of the present invention provide an EPO peptide set forth in SEQ ID NO: 5 having additionally at least one CTP amino acid peptide on the N-terminus and at least one CTP amino acid peptide on the C-terminus for improving stem cell engraftment. In another embodiment, the methods of the present invention provide an EPO peptide set forth in SEQ ID NO: 6 having additionally at least one CTP amino acid peptide on the N-terminus and at least one CTP amino acid peptide on the C-terminus for improving stem cell engraftment. In another embodiment, the methods of the present invention provide an EPO peptide set forth in SEQ ID NO: 16 having additionally at least one CTP amino acid peptide on the N-terminus and at least one CTP amino acid peptide on the C-terminus for improving stem cell engraftment. In another embodiment, the methods of the present invention provide an EPO peptide set forth in SEQ ID NO: 22 having additionally at least one CTP amino acid peptide on the N-terminus and at least one CTP amino acid peptide on the C-terminus for improving stem cell engraftment.

In another embodiment, the methods of the present invention provide a nucleic acid sequence encoding an EPO peptide having additionally at least one CTP amino acid peptide on the N-terminus and at least one CTP amino acid peptide on the C-terminus for improving stem cell engraftment. In another embodiment, the methods of the present invention provide a nucleic acid sequence encoding an EPO peptide having additionally one CTP amino acid peptide on the N-terminus and two CTP amino acid peptides on the C-terminus for improving stem cell engraftment. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for improving stem cell engraftment. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for improving stem cell engraftment.

In another embodiment, the methods of the present invention provide an EPO peptide having additionally at least one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide an EPO peptide having additionally one CTP amino acid peptide on the N-terminus and two CTP amino acid peptides on the C-terminus for increasing the survival rate of a patient with aplastic anemia or myelodysplastic syndrome. In another embodiment, the methods of the present invention provide an EPO peptide set forth in SEQ ID NO: 1 having additionally at least one CTP amino acid peptide on the N-terminus for increasing the survival rate of a patient with aplastic anemia or myelodysplastic syndrome. In another embodiment, the methods of the present invention provide an EPO peptide set forth in SEQ ID NO: 1 having additionally at least one CTP amino acid peptide on the N-terminus and at least additional one CTP amino acid peptide on the C-terminus for increasing the survival rate of a patient with aplastic anemia or myelodysplastic syndrome. In another embodiment, the methods of the present invention provide an EPO peptide set forth in SEQ ID NO: 2 having additionally at least one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide an EPO peptide set forth in SEQ ID NO: 3 having additionally at least one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide an EPO peptide set forth in SEQ ID NO: 4 having additionally at least one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide an EPO peptide set forth in SEQ ID NO: 5 having additionally at least one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide an EPO peptide set forth in SEQ ID NO: 6 having additionally at least one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide an EPO peptide set forth in SEQ ID NO: 16 having additionally at least one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide an EPO peptide set forth in SEQ ID NO: 22 having additionally at least one CTP amino acid peptide on the N-terminus and at least one CTP amino acid peptide on the C-terminus for increasing the survival rate of a patient with aplastic anemia or myelodysplastic syndrome.

In another embodiment, the methods of the present invention provide a nucleic acid sequence encoding an EPO peptide having additionally at least one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide a nucleic acid sequence encoding an EPO peptide having additionally one CTP amino acid peptide on the N-terminus and two CTP amino acid peptides on the C-terminus for increasing the survival rate of a patient with aplastic anemia or myelodysplastic syndrome. In another embodiment, the methods of the present invention provide a nucleic acid sequence as set forth in SEQ ID NO: 20 encoding an EPO peptide and one CTP amino acid peptide on the N-terminus and at least one CTP amino acid peptide on the C-terminus for increasing the survival rate of a patient with aplastic anemia or myelodysplastic syndrome. In another embodiment, the methods of the present invention provide a nucleic acid sequence as set forth in SEQ ID NO: 21 encoding an EPO peptide and one CTP amino acid peptide on the N-terminus and two CTP amino acid peptides on the C-terminus for increasing the survival rate of a patient with aplastic anemia or myelodysplastic syndrome.

Figure 11:
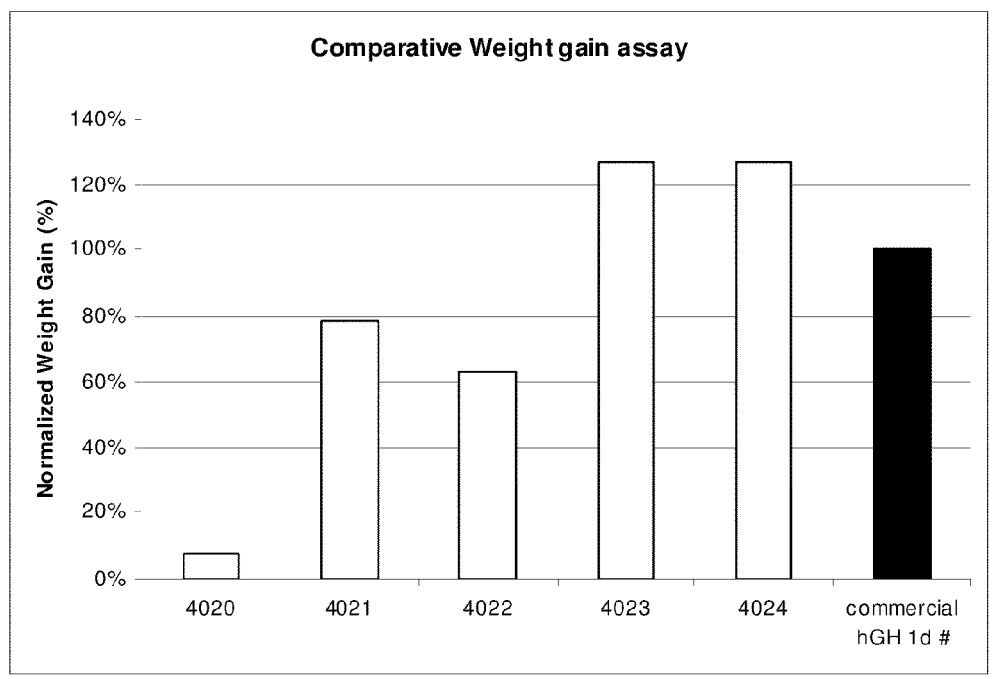
FIG. 11 is a bar graph illustrating the weight gain of hypophysectomized rats following administration of the GH-CTP polypeptides of the present invention.

In some embodiments, human growth hormone (hGH) is utilized according to the teachings of the present invention. In some embodiments, the attachment of CTP sequences to both the amino and carboxy termini of the hGH protein results in increased potency (FIG. 11). In some embodiments, the attachment of CTP sequences to both the amino and carboxy termini of the hGH protein results in prolonged in-vivo activity. In one embodiment, CTP-hGH polypeptides of the present invention are set forth in SEQ ID NOs: 39-41.

As provided herein, growth gain was demonstrated in hypophysectomized rats (which have no growth hormone secretion) following injections of CTP-hGH.

In one embodiment, the phrase "human growth hormone" (hGH) refers to a polypeptide, such as set forth in Genbank Accession No. P01241 (SEQ ID NO: 47), exhibiting hGH activity (i.e. stimulation of growth).

In another embodiment, "human growth hormone" (hGH) refers to a polypeptide, such as set forth in Genbank Accession No. P01241, exhibiting hGH activity (i.e. stimulation of growth). In another embodiment, "GH" of the present invention also refers to homologues. In another embodiment, a GH amino acid sequence of the methods and compositions of the present invention is at least 50% homologous to a GH sequence set forth herein as determined using BlastP software of the National Center of Biotechnology Information (NCBI) using default parameters. In another embodiment, the percent homology is 60%. In another embodiment, the percent homology is 70%. In another embodiment, the percent homology is 80%. In another embodiment, the percent homology is 90%. In another embodiment, the percent homology is at least 95%. In another embodiment, the percent homology is greater than 95%. Each possibility represents a separate embodiment of the present invention.

Exemplary CTP-GH polypeptides and CTP-hGH polypeptides of the present invention are set forth in SEQ ID NO: 39, SEQ ID NO: 40 and SEQ ID NO: 41.

In another embodiment, the methods of the present invention provide an hGh peptide having additionally at least one CTP amino acid peptide on the N-terminus and at least one CTP amino acid peptide on the C-terminus for stimulating muscle growth. In another embodiment, the methods of the present invention provide an hGh peptide having additionally one CTP amino acid peptide on the N-terminus and two CTP amino acid peptides on the C-terminus for stimulating muscle growth. In another embodiment, the methods of the present invention provide an hGH peptide set forth in SEQ ID NO: 23 having additionally at least one CTP amino acid peptide on the N-terminus and at least one CTP amino acid peptide on the C-terminus for stimulating muscle growth. In another embodiment, the methods of the present invention provide an hGH peptide set forth in SEQ ID NO: 36 having additionally at least one CTP amino acid peptide on the N-terminus and at least one CTP amino acid peptide on the C-terminus for stimulating muscle growth. In another embodiment, the methods of the present invention provide an hGH peptide set forth in SEQ ID NO: 37 having additionally at least one CTP amino acid peptide on the N-terminus for stimulating muscle growth. In another embodiment, the methods of the present invention provide an hGH peptide set forth in SEQ ID NO: 38 having additionally at least one CTP amino acid peptide on the N-terminus for stimulating muscle growth. In another embodiment, the methods of the present invention provide an hGH peptide set forth in SEQ ID NO: 39 for stimulating muscle growth. In another embodiment, the methods of the present invention provide an hGH peptide set forth in SEQ ID NO: 40 for stimulating muscle growth. In another embodiment, the methods of the present invention provide an hGH peptide set forth in SEQ ID NO: 41 for stimulating muscle growth. In another embodiment, the methods of the present invention provide an hGH peptide set forth in SEQ ID NO: 42 having additionally at least one CTP amino acid peptide on the N-terminus for stimulating muscle growth. In another embodiment, the methods of the present invention provide an hGH peptide modified by CTPs as described herein for stimulating muscle growth.

In another embodiment, the methods of the present invention provide a growth hormone (GH) peptide having additionally at least one CTP amino acid peptide on the N-terminus and at least one CTP amino acid peptide on the C-terminus for stimulating muscle growth. In another embodiment, the methods of the present invention provide a GH peptide having additionally one CTP amino acid peptide on the N-terminus and two CTP amino acid peptides on the C-terminus for stimulating muscle growth. In another embodiment, the methods of the present invention provide a GH peptide set forth in SEQ ID NO: 23 having additionally at least one CTP amino acid peptide on the N-terminus and at least one CTP amino acid peptide on the C-terminus for stimulating muscle growth. In another embodiment, the methods of the present invention provide a GH peptide set forth in SEQ ID NO: 36 having additionally at least one CTP amino acid peptide on the N-terminus and at least one CTP amino acid peptide on the C-terminus for stimulating muscle growth. In another embodiment, the methods of the present invention provide a GH peptide set forth in SEQ ID NO: 37 having additionally at least one CTP amino acid peptide on the N-terminus for stimulating muscle growth. In another embodiment, the methods of the present invention provide a GH peptide set forth in SEQ ID NO: 38, having additionally at least one CTP amino acid peptide on the N-terminus for stimulating muscle growth. In another embodiment, the methods of the present invention provide a GH peptide set forth in SEQ ID NO: 39 for stimulating muscle growth. In another embodiment, the methods of the present invention provide a GH peptide set forth in SEQ ID NO: 40 for stimulating muscle growth. In another embodiment, the methods of the present invention provide a GH peptide set forth in SEQ ID NO: 41 for stimulating muscle growth. In another embodiment, the methods of the present invention provide a GH peptide set forth in SEQ ID NO: 42 having additionally at least one CTP amino acid peptide on the N-terminus for stimulating muscle growth. In another embodiment, the methods of the present invention provide a GH peptide modified by CTPs as described herein for stimulating muscle growth.

In another embodiment, the methods of the present invention provide an hGh peptide having additionally at least one CTP amino acid peptide on the N-terminus and at least one CTP amino acid peptide on the C-terminus for stimulating bone growth. In another embodiment, the methods of the present invention provide an hGh peptide having additionally one CTP amino acid peptide on the N-terminus and two CTP amino acid peptides on the C-terminus for stimulating bone growth. In another embodiment, the methods of the present invention provide an hGH peptide set forth in SEQ ID NO: 23 having additionally at least one CTP amino acid peptide on the N-terminus and at least one CTP amino acid peptide on the C-terminus for stimulating bone growth. In another embodiment, the methods of the present invention provide an hGH peptide set forth in SEQ ID NO: 36 having additionally at least one CTP amino acid peptide on the N-terminus and at least one CTP amino acid peptide on the C-terminus for stimulating bone growth. In another embodiment, the methods of the present invention provide an hGH peptide set forth in SEQ ID NO: 37 having additionally at least one CTP amino acid peptide on the N-terminus for stimulating bone growth. In another embodiment, the methods of the present invention provide an hGH peptide set forth in SEQ ID NO: 38 having additionally at least one CTP amino acid peptide on the N-terminus for stimulating bone growth. In another embodiment, the methods of the present invention provide an hGH peptide set forth in SEQ ID NO: 39 for stimulating bone growth. In another embodiment, the methods of the present invention provide an hGH peptide set forth in SEQ ID NO: 40 for stimulating bone growth. In another embodiment, the methods of the present invention provide an hGH peptide set forth in SEQ ID NO: 41 for stimulating bone growth. In another embodiment, the methods of the present invention provide an hGH peptide set forth in SEQ ID having additionally at least one CTP amino acid peptide on the N-terminus for stimulating bone growth. In another embodiment, the methods of the present invention provide an hGH peptide modified by CTPs as described herein for stimulating bone growth.

In another embodiment, the methods of the present invention provide a GH peptide having additionally at least one CTP amino acid peptide on the N-terminus and at least one CTP amino acid peptide on the C-terminus for stimulating bone growth. In another embodiment, the methods of the present invention provide a GH peptide having additionally one CTP amino acid peptide on the N- terminus and two CTP amino acid peptides on the C-terminus for stimulating bone growth. In another embodiment, the methods of the present invention provide a GH peptide set forth in SEQ ID NO: 23 having additionally at least one CTP amino acid peptide on the N-terminus and at least one CTP amino acid peptide on the C-terminus for stimulating bone growth. In another embodiment, the methods of the present invention provide a GH peptide set forth in SEQ ID NO: 36 having additionally at least one CTP amino acid peptide on the N-terminus and at least one CTP amino acid peptide on the C-terminus for stimulating bone growth. In another embodiment, the methods of the present invention provide a GH peptide set forth in SEQ ID NO: 37 having additionally at least one CTP amino acid peptide on the N-terminus for stimulating bone growth. In another embodiment, the methods of the present invention provide a GH peptide set forth in SEQ ID NO: 38 having additionally at least one CTP amino acid peptide on the N-terminus for stimulating bone growth. In another embodiment, the methods of the present invention provide a GH peptide set forth in SEQ ID NO: 39 for stimulating bone growth. In another embodiment, the methods of the present invention provide a GH peptide set forth in SEQ ID NO: 40 for stimulating bone growth. In another embodiment, the methods of the present invention provide a GH peptide set forth in SEQ ID NO: 41 for stimulating bone growth. In another embodiment, the methods of the present invention provide a GH peptide set forth in SEQ ID NO: 42 having additionally at least one CTP amino acid peptide on the N-terminus for stimulating bone growth. In another embodiment, the methods of the present invention provide a GH peptide modified by CTPs as described herein for stimulating bone growth.

In another embodiment, the methods of the present invention provide a nucleic acid sequence encoding a GH peptide having additionally at least one CTP amino acid peptide on the N-terminus and at least one CTP amino acid peptide on the C-terminus for stimulating muscle growth. In another embodiment, the methods of the present invention provide a nucleic acid sequence encoding a GH peptide having additionally one CTP amino acid peptide on the N-terminus and two CTP amino acid peptides on the C-terminus for stimulating muscle growth. In another embodiment, the methods of the present invention provide a nucleic acid of SEQ ID NO: 45 encoding a GH peptide comprising one CTP amino acid peptide on the N-terminus and two CTP amino acid peptides on the C-terminus for stimulating muscle growth. In another embodiment, the methods of the present invention provide a nucleic acid of SEQ ID NO: 46 encoding a GH peptide and one CTP amino acid peptide on the N-terminus and two CTP amino acid peptides on the C-terminus for stimulating muscle growth.

In another embodiment, the methods of the present invention provide a GH peptide of the present invention for maintaining muscle quality.

In another embodiment, the methods of the present invention provide a GH of the present invention for maintaining bone quality.

In another embodiment, the methods of the present invention provide an hGh peptide having additionally at least one CTP amino acid peptide on the N-terminus and at least one CTP amino acid peptide on the C-terminus for treating a wasting disease. In another embodiment, the methods of the present invention provide an hGh peptide having additionally one CTP amino acid peptide on the N-terminus and two CTP amino acid peptides on the C-terminus for treating a wasting disease. In another embodiment, the methods of the present invention provide an hGH peptide set forth in SEQ ID NO: 23 having additionally at least one CTP amino acid peptide on the N-terminus and at least one CTP amino acid peptide on the C-terminus for treating a wasting disease. In another embodiment, the methods of the present invention provide an hGH peptide set forth in SEQ ID NO: 36 having additionally at least one CTP amino acid peptide on the N-terminus and at least one CTP amino acid peptide on the C-terminus for treating a wasting disease. In another embodiment, the methods of the present invention provide an hGH peptide set forth in SEQ ID NO: 37 having additionally at least one CTP amino acid peptide on the N-terminus for treating a wasting disease. In another embodiment, the methods of the present invention provide an hGH peptide set forth in SEQ ID NO: 38 having additionally at least one CTP amino acid peptide on the N-terminus for treating a wasting disease. In another embodiment, the methods of the present invention provide an hGH peptide set forth in SEQ ID NO: 39 for treating a wasting disease. In another embodiment, the methods of the present invention provide an hGH peptide set forth in SEQ ID NO: 40 for treating a wasting disease. In another embodiment, the methods of the present invention provide an hGH peptide set forth in SEQ ID NO: 41 for treating a wasting disease. In another embodiment, the methods of the present invention provide an hGH peptide set forth in SEQ ID NO: 42 having additionally at least one CTP amino acid peptide on the N-terminus for treating a wasting disease. In another embodiment, the methods of the present invention provide an hGH peptide modified by CTPs as described herein for treating a wasting disease.

In another embodiment, the methods of the present invention provide a UH peptide having additionally at least one CTP amino acid peptide on the N-terminus and at least one CTP amino acid peptide on the C-terminus for treating a wasting disease. In another embodiment, the methods of the present invention provide a UH peptide having additionally one CTP amino acid peptide on the N-terminus and two CTP amino acid peptides on the C-terminus for treating a wasting disease. In another embodiment, the methods of the present invention provide a GH peptide set forth in SEQ ID NO: 23 having additionally at least one CTP amino acid peptide on the N-terminus and at least one CTP amino acid peptide on the C-terminus for treating a wasting disease. In another embodiment, the methods of the present invention provide a GH peptide set forth in SEQ ID NO: 36 having additionally at least one CTP amino acid peptide on the N-terminus and at least one CTP amino acid peptide on the C-terminus for treating a wasting disease. In another embodiment, the methods of the present invention provide a GH peptide set forth in SEQ ID NO: 37 having additionally at least one CTP amino acid peptide on the N-terminus for treating a wasting disease. In another embodiment, the methods of the present invention provide a GH peptide set forth in SEQ ID NO: 38 having additionally at least one CTP amino acid peptide on the N-terminus for treating a wasting disease. In another embodiment, the methods of the present invention provide a GH peptide set forth in SEQ ID NO: 39 for treating a wasting disease. In another embodiment, the methods of the present invention provide a GH peptide set forth in SEQ ID NO: 40 for treating a wasting disease. In another embodiment, the methods of the present invention provide a GH peptide set forth in SEQ ID NO: 41 for treating a wasting disease. In another embodiment, the methods of the present invention provide a GH peptide set forth in SEQ ID NO: 42 having additionally at least one CTP amino acid peptide on the N-terminus for treating a wasting disease. In another embodiment, the methods of the present invention provide a GH peptide modified by CTPs as described herein for treating a wasting disease.

In another embodiment, the methods of the present invention provide an hGh peptide having additionally at least one CTP amino acid peptide on the N-terminus and at least one CTP amino acid peptide on the C-terminus for increasing cardiac function. In another embodiment, the methods of the present invention provide an hGh peptide having additionally one CTP amino acid peptide on the N-terminus and two CTP amino acid peptides on the C-terminus for increasing cardiac function. In another embodiment, the methods of the present invention provide an hGH peptide set forth in SEQ ID NO: 23 having additionally at least one CTP amino acid peptide on the N-terminus and at least one CTP amino acid peptide on the C-terminus for increasing cardiac function. In another embodiment, the methods of the present invention provide an hGH peptide set forth in SEQ ID NO: 36 having additionally at least one CTP amino acid peptide on the N-terminus and at least one CTP amino acid peptide on the C-terminus for increasing cardiac function. In another embodiment, the methods of the present invention provide an hGH peptide set forth in SEQ ID NO: 37 having additionally at least one CTP amino acid peptide on the N-terminus for increasing cardiac function. In another embodiment, the methods of the present invention provide an hGH peptide set forth in SEQ ID NO: 38 having additionally at least one CTP amino acid peptide on the N-terminus for increasing cardiac function. In another embodiment, the methods of the present invention provide an hGH peptide set forth in SEQ ID NO: 39 for increasing cardiac function. In another embodiment, the methods of the present invention provide an hGH peptide set forth in SEQ ID NO: 40 for increasing cardiac function. In another embodiment, the methods of the present invention provide an hGH peptide set forth in SEQ ID NO: 41 for increasing cardiac function. In another embodiment, the methods of the present invention provide an hGH peptide set forth in SEQ ID NO: 42 having additionally at least one CTP amino acid peptide on the N-terminus for increasing cardiac function. In another embodiment, the methods of the present invention provide an hGH peptide modified by CTPs as described herein for increasing cardiac function.

In another embodiment, the methods of the present invention provide a nucleic acid sequence encoding a GH peptide having additionally at least one CTP amino acid peptide on the N-terminus and at least one CTP amino acid peptide on the C-terminus for increasing cardiac function. In another embodiment, the methods of the present invention provide a nucleic acid sequence encoding a GH peptide having additionally one CTP amino acid peptide on the N-terminus and two CTP amino acid peptides on the C-terminus for increasing cardiac function. In another embodiment, the methods of the present invention provide a nucleic acid of SEQ ID NO: 45 encoding a GH peptide comprising one CTP amino acid peptide on the N-terminus and two CTP amino acid peptides on the C-terminus for increasing cardiac function. In another embodiment, the methods of the present invention provide a nucleic acid of SEQ ID NO: 46 encoding a GH peptide and one CTP amino acid peptide on the N-terminus and two CTP amino acid peptides on the C-terminus for increasing cardiac function.

In another embodiment, the methods of the present invention provide an hGh peptide having additionally at least one CTP amino acid peptide on the N-terminus and at least one CTP amino acid peptide on the C-terminus for increasing lipolysis. In another embodiment, the methods of the present invention provide an hGh peptide having additionally one CTP amino acid peptide on the N-terminus and two CTP amino acid peptides on the C-terminus for increasing lipolysis. In another embodiment, the methods of the present invention provide an hGH peptide set forth in SEQ ID NO: 23 having additionally at least one CTP amino acid peptide on the N-terminus and at least one CTP amino acid peptide on the C-terminus for increasing lipolysis. In another embodiment, the methods of the present invention provide an hGH peptide set forth in SEQ ID NO: 36 having additionally at least one CTP amino acid peptide on the N-terminus and at least one CTP amino acid peptide on the C-terminus for increasing lipolysis. In another embodiment, the methods of the present invention provide an hGH peptide set forth in SEQ ID NO: 37 having additionally at least one CTP amino acid peptide on the N-terminus for increasing lipolysis. In another embodiment, the methods of the present invention provide an hGH peptide set forth in SEQ ID NO: 38 having additionally at least one CTP amino acid peptide on the N-terminus for increasing lipolysis. In another embodiment, the methods of the present invention provide an hGH peptide set forth in SEQ ID NO: 39 for increasing lipolysis. In another embodiment, the methods of the present invention provide an hGH peptide set forth in SEQ ID NO: 40 for increasing lipolysis. In another embodiment, the methods of the present invention provide an hGH peptide set forth in SEQ ID NO: 41 for increasing lipolysis. In another embodiment, the methods of the present invention provide an hGH peptide set forth in SEQ ID NO: 42 having additionally at least one CTP amino acid peptide on the N-terminus for increasing lipolysis. In another embodiment, the methods of the present invention provide an hGH modified by CTPs as described herein for increasing lipolysis.

In another embodiment, the methods of the present invention provide a nucleic acid sequence encoding a GH peptide having additionally at least one CTP amino acid peptide on the N-terminus and at least one CTP amino acid peptide on the C-terminus for increasing lipolysis. In another embodiment, the methods of the present invention provide a nucleic acid sequence encoding a GH peptide having additionally one CTP amino acid peptide on the N-terminus and two CTP amino acid peptides on the C-terminus for increasing lipolysis. In another embodiment, the methods of the present invention provide a nucleic acid of SEQ ID NO: 45 encoding a GH peptide comprising one CTP amino acid peptide on the N-terminus and two CTP amino acid peptides on the C-terminus for increasing lipolysis. In another embodiment, the methods of the present invention provide a nucleic acid of SEQ ID NO: 46 encoding a GH peptide and one CTP amino acid peptide on the N-terminus and two CTP amino acid peptides on the C-terminus for increasing lipolysis.

In another embodiment, the methods of the present invention provide an hGh peptide having additionally at least one CTP amino acid peptide on the N-terminus and at least one CTP amino acid peptide on the C-terminus for improving fluid balance. In another embodiment, the methods of the present invention provide an hGh peptide having additionally one CTP amino acid peptide on the N-terminus and two CTP amino acid peptides on the C-terminus for improving fluid balance. In another embodiment, the methods of the present invention provide an hGH peptide set forth in SEQ ID NO: 23 having additionally at least one CTP amino acid peptide on the N-terminus and at least one CTP amino acid peptide on the C-terminus for improving fluid balance. In another embodiment, the methods of the present invention provide an hGH peptide set forth in SEQ ID NO: 36 having additionally at least one CTP amino acid peptide on the N-terminus and at least one CTP amino acid peptide on the C-terminus for improving fluid balance. In another embodiment, the methods of the present invention provide an hGH peptide set forth in SEQ ID NO: 37 having additionally at least one CTP amino acid peptide on the N-terminus for improving fluid balance. In another embodiment, the methods of the present invention provide an hGH peptide set forth in SEQ ID NO: 38 having additionally at least one CTP amino acid peptide on the N-terminus for improving fluid balance. In another embodiment, the methods of the present invention provide an hGH peptide set forth in SEQ ID NO: 39 for improving fluid balance. In another embodiment, the methods of the present invention provide an hGH peptide set forth in SEQ ID NO: 40 for improving fluid balance. In another embodiment, the methods of the present invention provide an hGH peptide set forth in SEQ ID NO: 41 for improving fluid balance. In another embodiment, the methods of the present invention provide an hGH peptide set forth in SEQ ID NO: 42 having additionally at least one CTP amino acid peptide on the N-terminus for improving fluid balance. In another embodiment, the methods of the present invention provide an hGH modified by CTPs as described herein for improving fluid balance.

In another embodiment, the methods of the present invention provide a nucleic acid sequence encoding a GH peptide having additionally at least one CTP amino acid peptide on the N-terminus and at least one CTP amino acid peptide on the C-terminus for improving fluid balance. In another embodiment, the methods of the present invention provide a nucleic acid sequence encoding a GH peptide having additionally one CTP amino acid peptide on the N-terminus and two CTP amino acid peptides on the C-terminus for improving fluid balance. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving fluid balance. In another embodiment, the methods of the present invention provide a nucleic acid of SEQ ID NO: 46 encoding a GH peptide and one CTP amino acid peptide on the N-terminus and two CTP amino acid peptides on the C-terminus for improving fluid balance.

In another embodiment, the methods of the present invention provide an hGh peptide having additionally at least one CTP amino acid peptide on the N-terminus and at least one CTP amino acid peptide on the C-terminus for treating osteoporosis. In another embodiment, the methods of the present invention provide an hGh peptide having additionally one CTP amino acid peptide on the N-terminus and two CTP amino acid peptides on the C-terminus for treating osteoporosis. In another embodiment, the methods of the present invention provide an hGH peptide set forth in SEQ ID NO: 23 having additionally at least one CTP amino acid peptide on the N-terminus and at least one CTP amino acid peptide on the C-terminus for treating osteoporosis. In another embodiment, the methods of the present invention provide an hGH peptide set forth in SEQ ID NO: 36 having additionally at least one CTP amino acid peptide on the N-terminus and at least one CTP amino acid peptide on the C-terminus for treating osteoporosis. In another embodiment, the methods of the present invention provide an hGH peptide set forth in SEQ ID NO: 37 having additionally at least one CTP amino acid peptide on the N-terminus for treating osteoporosis. In another embodiment, the methods of the present invention provide an hGH peptide set forth in SEQ ID NO: 38 having additionally at least one CTP amino acid peptide on the N-terminus for treating osteoporosis. In another embodiment, the methods of the present invention provide an hGH peptide set forth in SEQ ID NO: 39 for treating osteoporosis. In another embodiment, the methods of the present invention provide an hGH peptide set forth in SEQ ID NO: 40 for treating osteoporosis. In another embodiment, the methods of the present invention provide an hGH peptide set forth in SEQ ID NO: 41 for treating osteoporosis. In another embodiment, the methods of the present invention provide an hGH peptide set forth in SEQ ID NO: 42 having additionally at least one CTP amino acid peptide on the N-terminus for treating osteoporosis. In another embodiment, the methods of the present invention provide an hGH peptide modified by CTPs as described herein for treating osteoporosis.

In another embodiment, the methods of the present invention provide a nucleic acid sequence encoding a GH peptide having additionally at least one CTP amino acid peptide on the N-terminus and at least one CTP amino acid peptide on the C-terminus for treating osteoporosis. In another embodiment, the methods of the present invention provide a nucleic acid sequence encoding a GH peptide having additionally one CTP amino acid peptide on the N-terminus and two CTP amino acid peptides on the C-terminus for treating osteoporosis. In another embodiment, the methods of the present invention provide a nucleic acid of SEQ ID NO: 45 encoding a GH peptide comprising one CTP amino acid peptide on the N-terminus and two CTP amino acid peptides on the C-terminus for treating osteoporosis. In another embodiment, the methods of the present invention provide a nucleic acid of SEQ ID NO: 46 encoding a GH peptide and one CTP amino acid peptide on the N-terminus and two CTP amino acid peptides on the C-terminus for treating osteoporosis.

In another embodiment, the methods of the present invention provide an hGh peptide having additionally at least one CTP amino acid peptide on the N-terminus and at least one CTP amino acid peptide on the C-terminus for inhibiting osteoporosis. In another embodiment, the methods of the present invention provide an hGh peptide having additionally one CTP amino acid peptide on the N-terminus and two CTP amino acid peptides on the C-terminus for inhibiting osteoporosis. In another embodiment, the methods of the present invention provide an hGH peptide set forth in SEQ ID NO: 23 having additionally at least one CTP amino acid peptide on the N-terminus and at least one CTP amino acid peptide on the C-terminus for inhibiting osteoporosis. In another embodiment, the methods of the present invention provide an hGH peptide set forth in SEQ ID NO: 36 having additionally at least one CTP amino acid peptide on the N-terminus and at least one CTP amino acid peptide on the C-terminus for inhibiting osteoporosis. In another embodiment, the methods of the present invention provide an hGH peptide set forth in SEQ ID NO: 37 having additionally at least one CTP amino acid peptide on the N-terminus for inhibiting osteoporosis. In another embodiment, the methods of the present invention provide an hGH peptide set forth in SEQ ID NO: 38 having additionally at least one CTP amino acid peptide on the N-terminus for inhibiting osteoporosis. In another embodiment, the methods of the present invention provide an hGH peptide set forth in SEQ ID NO: 39 for inhibiting osteoporosis. In another embodiment, the methods of the present invention provide an hGH peptide set forth in SEQ ID NO: 40 for inhibiting osteoporosis. In another embodiment, the methods of the present invention provide an hGH peptide set forth in SEQ ID NO: 41 for inhibiting osteoporosis. In another embodiment, the methods of the present invention provide an hGH peptide set forth in SEQ ID NO: 42 having additionally at least one CTP amino acid peptide on the N-terminus for inhibiting osteoporosis. In another embodiment, the methods of the present invention provide an hGH peptide modified by CTPs as described herein for inhibiting osteoporosis.

In another embodiment, the methods of the present invention provide a nucleic acid sequence encoding a GH peptide having additionally at least one CTP amino acid peptide on the N-terminus and at least one CTP amino acid peptide on the C-terminus for inhibiting osteoporosis. In another embodiment, the methods of the present invention provide a nucleic acid sequence encoding a GH peptide having additionally one CTP amino acid peptide on the N-terminus and two CTP amino acid peptides on the C-terminus for inhibiting osteoporosis. In another embodiment, the methods of the present invention provide a nucleic acid of SEQ ID NO: 45 encoding a GH peptide comprising one CTP amino acid peptide on the N-terminus and two CTP amino acid peptides on the C-terminus for inhibiting osteoporosis. In another embodiment, the methods of the present invention provide a nucleic acid of SEQ ID NO: 46 encoding a GH peptide and one CTP amino acid peptide on the N-terminus and two CTP amino acid peptides on the C-terminus for inhibiting osteoporosis.

In another embodiment, the methods of the present invention provide a GH peptide of the present invention for improving exercise capacity.

In another embodiment, the methods of the present invention provide an hGh peptide having additionally at least one CTP amino acid peptide on the N-terminus and at least one CTP amino acid peptide on the C-terminus for improving lung function. In another embodiment, the methods of the present invention provide an hGh peptide having additionally one CTP amino acid peptide on the N-terminus and two CTP amino acid peptides on the C-terminus for improving lung function. In another embodiment, the methods of the present invention provide an hGH peptide set forth in SEQ ID NO: 23 having additionally at least one CTP amino acid peptide on the N-terminus and at least one CTP amino acid peptide on the C-terminus for improving lung function. In another embodiment, the methods of the present invention provide an hGH peptide set forth in SEQ ID NO: 36 having additionally at least one CTP amino acid peptide on the N-terminus and at least one CTP amino acid peptide on the C-terminus for improving lung function. In another embodiment, the methods of the present invention provide an hGH peptide set forth in SEQ ID NO: 37 having additionally at least one CTP amino acid peptide on the N-terminus for improving lung function. In another embodiment, the methods of the present invention provide an hGH peptide set forth in SEQ ID NO: 38 having additionally at least one CTP amino acid peptide on the N-terminus for improving lung function. In another embodiment, the methods of the present invention provide an hGH peptide set forth in SEQ ID NO: 39 for improving lung function. In another embodiment, the methods of the present invention provide an hGH peptide set forth in SEQ ID NO: 40 for improving lung function. In another embodiment, the methods of the present invention provide an hGH peptide set forth in SEQ ID NO: 41 for improving lung function. In another embodiment, the methods of the present invention provide an hGH peptide set forth in SEQ ID NO: 42 having additionally at least one CTP amino acid peptide on the N-terminus for improving lung function. In another embodiment, the methods of the present invention provide an hGH peptide modified by CTPs as described herein for improving lung function.

In another embodiment, the methods of the present invention provide a nucleic acid sequence encoding a GH peptide having additionally at least one CTP amino acid peptide on the N-terminus and at least one CTP amino acid peptide on the C-terminus for improving lung function. In another embodiment, the methods of the present invention provide a nucleic acid sequence encoding a GH peptide having additionally one CTP amino acid peptide on the N-terminus and two CTP amino acid peptides on the C-terminus for improving lung function. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving lung function. In another embodiment, the methods of the present invention provide a nucleic acid of SEQ ID NO: 46 encoding a GH peptide and one CTP amino acid peptide on the N-terminus and two CTP amino acid peptides on the C-terminus for improving lung function.

In another embodiment, the methods of the present invention provide an hGh peptide having additionally at least one CTP amino acid peptide on the N-terminus and at least one CTP amino acid peptide on the C-terminus for improving immunity. In another embodiment, the methods of the present invention provide an hGh peptide having additionally one CTP amino acid peptide on the N-terminus and two CTP amino acid peptides on the C-terminus for improving immunity. In another embodiment, the methods of the present invention provide an hGH peptide set forth in SEQ ID NO: 23 having additionally at least one CTP amino acid peptide on the N-terminus and at least one CTP amino acid peptide on the C-terminus for improving immunity. In another embodiment, the methods of the present invention provide an hGH peptide set forth in SEQ ID NO: 36 having additionally at least one CTP amino acid peptide on the N-terminus and at least one CTP amino acid peptide on the C-terminus for improving immunity. In another embodiment, the methods of the present invention provide an hGH peptide set forth in SEQ ID NO: 37 having additionally at least one CTP amino acid peptide on the N-terminus for improving immunity. In another embodiment, the methods of the present invention provide an hGH peptide set forth in SEQ ID NO: 38 having additionally at least one CTP amino acid peptide on the N-terminus for improving immunity. In another embodiment, the methods of the present invention provide an hGH peptide set forth in SEQ ID NO: 39 for improving immunity. In another embodiment, the methods of the present invention provide an hGH peptide set forth in SEQ ID NO: 40 for improving immunity. In another embodiment, the methods of the present invention provide an hGH peptide set forth in SEQ ID NO: 41 for improving immunity. In another embodiment, the methods of the present invention provide an hGH peptide set forth in SEQ ID NO: 42 having additionally at least one CTP amino acid peptide on the N-terminus for improving immunity. In another embodiment, the methods of the present invention provide an hGH peptide modified by CTPs as described herein for improving immunity.

In another embodiment, the methods of the present invention provide a nucleic acid sequence encoding a GH peptide having additionally at least one CTP amino acid peptide on the N-terminus and at least one CTP amino acid peptide on the C-terminus for improving immunity. In another embodiment, the methods of the present invention provide a nucleic acid sequence encoding a GH peptide having additionally one CTP amino acid peptide on the N-terminus and two CTP amino acid peptides on the C-terminus for improving immunity. In another embodiment, the methods of the present invention provide a nucleic acid of SEQ ID NO: 45 encoding a GH peptide comprising one CTP amino acid peptide on the N-terminus and two CTP amino acid peptides on the C-terminus for improving immunity. In another embodiment, the methods of the present invention provide a nucleic acid of SEQ ID NO: 46 encoding a GH peptide and one CTP amino acid peptide on the N-terminus and two CTP amino acid peptides on the C-terminus for improving immunity.

In another embodiment, the methods of the present invention provide an hGh peptide having additionally at least one CTP amino acid peptide on the N-terminus and at least one CTP amino acid peptide on the C-terminus for regrowing vital organs. In another embodiment, the methods of the present invention provide an hGh peptide having additionally one CTP amino acid peptide on the N-terminus and two CTP amino acid peptides on the C-terminus for regrowing vital organs. In another embodiment, the methods of the present invention provide an hGH peptide set forth in SEQ ID NO: 23 having additionally at least one CTP amino acid peptide on the N-terminus and at least one CTP amino acid peptide on the C-terminus for regrowing vital organs. In another embodiment, the methods of the present invention provide an hGH peptide set forth in SEQ ID NO: 36 having additionally at least one CTP amino acid peptide on the N-terminus and at least one CTP amino acid peptide on the C-terminus for regrowing vital organs. In another embodiment, the methods of the present invention provide an hGH peptide set forth in SEQ ID NO: 37 having additionally at least one CTP amino acid peptide on the N-terminus for regrowing vital organs. In another embodiment, the methods of the present invention provide an hGH peptide set forth in SEQ ID NO: 38 having additionally at least one CTP amino acid peptide on the N-terminus for regrowing vital organs. In another embodiment, the methods of the present invention provide an hGH peptide set forth in SEQ ID NO: 39 for regrowing vital organs. In another embodiment, the methods of the present invention provide an hGH peptide set forth in SEQ ID NO: 40 for regrowing vital organs. In another embodiment, the methods of the present invention provide an hGH peptide set forth in SEQ ID NO: 41 for regrowing vital organs. In another embodiment, the methods of the present invention provide an hGH peptide set forth in SEQ ID NO: 42 having additionally at least one CTP amino acid peptide on the N-terminus for regrowing vital organs. In another embodiment, the methods of the present invention provide an hGH peptide modified by CTPs as described herein for regrowing vital organs.

In another embodiment, the methods of the present invention provide a nucleic acid sequence encoding a GH peptide having additionally at least one CTP amino acid peptide on the N-terminus and at least one CTP amino acid peptide on the C-terminus for regrowing vital organs. In another embodiment, the methods of the present invention provide a nucleic acid sequence encoding a GH peptide having additionally one CTP amino acid peptide on the N-terminus and two CTP amino acid peptides on the C-terminus for regrowing vital organs. In another embodiment, the methods of the present invention provide a nucleic acid of SEQ ID NO: 45 encoding a GH peptide comprising one CTP amino acid peptide on the N-terminus and two CTP amino acid peptides on the C-terminus for regrowing vital organs. In another embodiment, the methods of the present invention provide a nucleic acid of SEQ ID NO: 46 encoding a GH peptide and one CTP amino acid peptide on the N-terminus and two CTP amino acid peptides on the C-terminus for regrowing vital organs.

In another embodiment, the methods of the present invention provide a GH peptide of the present invention for increasing sense of well-being.

In another embodiment, the methods of the present invention provide an hGh peptide having additionally at least one CTP amino acid peptide on the N-terminus and at least one CTP amino acid peptide on the C-terminus for restoring REM sleep. In another embodiment, the methods of the present invention provide an hGh peptide having additionally one CTP amino acid peptide on the N-terminus and two CTP amino acid peptides on the C-terminus for restoring REM sleep. In another embodiment, the methods of the present invention provide an hGH peptide set forth in SEQ ID NO: 23 having additionally at least one CTP amino acid peptide on the N-terminus and at least one CTP amino acid peptide on the C-terminus for restoring REM sleep. In another embodiment, the methods of the present invention provide an hGH peptide set forth in SEQ ID NO: 36 having additionally at least one CTP amino acid peptide on the N-terminus and at least one CTP amino acid peptide on the C-terminus for restoring REM sleep. In another embodiment, the methods of the present invention provide an hGH peptide set forth in SEQ ID NO: 37 having additionally at least one CTP amino acid peptide on the N-terminus for restoring REM sleep. In another embodiment, the methods of the present invention provide an hGH peptide set forth in SEQ ID NO: 38 having additionally at least one CTP amino acid peptide on the N-terminus for restoring REM sleep. In another embodiment, the methods of the present invention provide an hGH peptide set forth in SEQ ID NO: 39 for restoring REM sleep. In another embodiment, the methods of the present invention provide an hGH peptide set forth in SEQ ID NO: 40 for restoring REM sleep. In another embodiment, the methods of the present invention provide an hGH peptide set forth in SEQ ID NO: 41 for restoring REM sleep. In another embodiment, the methods of the present invention provide an hGH peptide set forth in SEQ ID NO: 42 having additionally at least one CTP amino acid peptide on the N-terminus for restoring REM sleep. In another embodiment, the methods of the present invention provide an hGH peptide modified by CTPs as described herein for restoring REM sleep.

In another embodiment, the methods of the present invention provide a nucleic acid sequence encoding a GH peptide having additionally at least one CTP amino acid peptide on the N-terminus and at least one CTP amino acid peptide on the C-terminus for restoring REM sleep. In another embodiment, the methods of the present invention provide a nucleic acid sequence encoding a GH peptide having additionally one CTP amino acid peptide on the N-terminus and two CTP amino acid peptides on the C-terminus for restoring REM sleep. In another embodiment, the methods of the present invention provide a nucleic acid of SEQ ID NO: 45 encoding a GH peptide comprising one CTP amino acid peptide on the N-terminus and two CTP amino acid peptides on the C-terminus for restoring REM sleep. In another embodiment, the methods of the present invention provide a nucleic acid of SEQ ID NO: 46 encoding a GH peptide and one CTP amino acid peptide on the N-terminus and two CTP amino acid peptides on the C-terminus for restoring REM sleep.

In some embodiments, "homology" according to the present invention also encompasses deletions, insertions, or substitution variants, including an amino acid substitution thereof, and biologically active polypeptide fragments thereof. In one embodiment the substitution variant is one in which the glutamine in position 65 of hGH is substituted by a valine (SEQ ID NO: 23) [Gellerfors et al., J Pharm Biomed Anal 1989, 7:173-83].

In some embodiments, interferon is utilized according to the teachings of the present invention. In some embodiments, the attachment of CTP sequences to both the amino and carboxy termini of the interferon protein results in increased potency. In some embodiments, the attachment of CTP sequences to both the amino and carboxy termini of the interferon protein results in prolonged in-vivo activity.

In one embodiment, "interferon" refers to the mammalian interferon polypeptide Type I. In one embodiment, "interferon" refers to the mammalian interferon polypeptide Type II. In some embodiments, additional suitable interferon polypeptides as known to those of ordinary skill in the art are utilized. In some embodiments, the interferon is alpha-interferon. In some embodiments, the interferon is beta-interferon. In some embodiments, the interferon is gamma-interferon. In some embodiments, the interferon is omega-interferon. In some embodiments, the interferon is a subspecies interferon. In one embodiment, the subspecies of interferon (IFN) is IFN-α2a. In one embodiment, the subspecies of interferon IFN) is IFN-α2b. In one embodiment, the subspecies interferon (IFN) is IFN-β1a. In one embodiment, the interferon (IFN) subspecies is IFN-β1b.

In one embodiment, an interferon of the present invention exhibits interferon activity, such as antiviral or antiproliferative activity. In some embodiments, GenBank Accession Numbers of non-limiting examples of interferons are listed in Table 1 below.

In one embodiment, an interferon of the present invention also refers to homologues. In one embodiment, an interferon amino acid sequence of the present invention is at least 50% homologous to an interferon sequence disclosed herein. In one embodiment, an interferon amino acid sequence of the present invention is at least 60% homologous an interferon sequence disclosed herein. In one embodiment, interferon amino acid sequence of the present invention is at least 70% homologous an interferon sequence disclosed herein. In one embodiment, an interferon amino acid sequence of the present invention is at least 80% homologous to an interferon sequence disclosed herein. In one embodiment, an interferon amino acid sequence of the present invention is at least 90% homologous to an interferon sequence disclosed herein. In one embodiment, an interferon amino acid sequence of the present invention is at least 95% homologous an interferon sequence disclosed herein. In some embodiments, homology according to the present invention also encompasses deletions, insertions, or substitution variants, including an amino acid substitution thereof and biologically active polypeptide fragments thereof. In one embodiment, the cysteine in position 17 of interferon β is substituted by a serine (SEQ ID NO: 24).

Table 1 below lists examples of interferons with their respective NCBI sequence numbers.

TABLE 1

| Interferon name | NCBI sequence number |
| --- | --- |
| interferon, α 1 | NP_076918.1 |
| interferon, α 10 | NP_002162.1 |
| interferon, α13 | NP_008831.2 |
| interferon, α14 | NP_002163.1 |
| interferon, α16 | NP_002164.1 |
| interferon, α17 | NP_067091.1 |
| interferon, α2 | NP_000596.2 |
| interferon, α21 | NP_002166.1 |
| interferon, α4 | NP_066546.1 |
| interferon, α5 | NP_002160.1 |
| interferon, α6 | NP_066282.1 |
| interferon, α7 | NP_066401.2 |
| interferon, α8 | NP_002161.2 |
| interferon, β 1 | NP_002167.1 |
| interferon, ε1 | NP_795372.1 |
| interferon, γ | NP_000610.2 |
| interferon, ε | NP_064509.1 |
| interferon, Ω1 | NP_002168.1 |

In another embodiment, the methods of the present invention provide an interferon beta 1 peptide having additionally at least one CTP amino acid peptide on the N-terminus and at least one CTP amino acid peptide on the C-terminus for treating or inhibiting multiple sclerosis. In another embodiment, the methods of the present invention provide an interferon beta 1 peptide having additionally one CTP amino acid peptide on the N-terminus and two CTP amino acid peptides on the C-terminus for treating or inhibiting multiple sclerosis. In another embodiment, the methods of the present invention provide an interferon beta 1 peptide set forth in SEQ ID NO: 24 having additionally at least one CTP amino acid peptide on the N-terminus and one CTP amino acid peptide on the C-terminus for treating or inhibiting multiple sclerosis. In another embodiment, the methods of the present invention provide an interferon beta 1 peptide set forth in SEQ ID NO: 24 having additionally on the N-terminus the signal peptide of SEQ ID NO: 26 and at least one CTP amino acid peptide on the N-terminus of SEQ ID NO: 26 and at least one CTP amino acid peptide on the C-terminus of SEQ ID NO: 24 for treating or inhibiting multiple sclerosis.

In some embodiments, glucagon-like peptide-1 is utilized according to the teachings of the present invention. In some embodiments, the attachment of CTP sequences to both the amino and carboxy termini of a "glucagon-like peptide-1" results in increased potency. In some embodiments, the attachment of CTP sequences to both the amino and carboxy termini of a peptide results in prolonged in-vivo activity. In some embodiments, the attachment of CTP sequences to both the amino and carboxy termini of the glucagon-like peptide-results in prolonged in-vivo activity.

In one embodiment, "glucagon-like peptide-1" (GLP-1) refers to a mammalian polypeptide. In one embodiment, "glucagon-like peptide-1" (GLP-1) refers to a human polypeptide. In some embodiments, GLP-1 is cleaved from the glucagon preproprotein (Genbank ID No. NP002045) that has the ability to bind to the GLP-1 receptor and initiate a signal transduction pathway resulting in insulinotropic activity. In one embodiment, "insulinotropic activity" refers to the ability to stimulate insulin secretion in response to elevated glucose levels, thereby causing glucose uptake by cells and decreased plasma glucose levels. In some embodiments, GLP-1 polypeptides include, but are not limited to those described in U.S. Pat. No. 5,118,666; which is incorporated by reference herein.

In one embodiment, "GLP-1" refers to a polypeptide, such as set forth in sequences set forth in SEQ ID NO: 25 as determined using BlastP software of the National Center of Biotechnology Information (NCBI) using default parameters. In one embodiment, a GLP-1 of the present invention also refers to a GLP-1 homologue. In one embodiment, a GLP-1 amino acid sequence of the present invention is at least 50% homologous to GLP-1 sequences set forth in SEQ ID NO: 25 as determined using BlastP software of the National Center of Biotechnology Information (NCBI) using default parameters. In one embodiment, a GLP-1 amino acid sequence of the present invention is at least 60% homologous to GLP-1 sequences set forth in SEQ ID NO: 25 as determined using BlastP software of the National Center of Biotechnology Information (NCBI) using default parameters. In one embodiment, a GLP-1 amino acid sequence of the present invention is at least 70% homologous to GLP-1 sequences set forth in SEQ ID NO: 25 as determined using BlastP software of the National Center of Biotechnology Information (NCBI) using default parameters. In one embodiment, GLP-1 amino acid sequence of the present invention is at least 80% homologous to GLP-1 sequences set forth in SEQ ID NO: 25 as determined using BlastP software of the National Center of Biotechnology Information (NCBI) using default parameters. In one embodiment, a GLP-1 amino acid sequence of the present invention is at least 90% homologous to GLP-1 sequences set forth in SEQ ID NO: 25 as determined using BlastP software of the National Center of Biotechnology Information (NCBI) using default parameters. In one embodiment, a GLP-1 amino acid sequence of the present invention is at least 95% homologous to GLP-1 sequences set forth in SEQ ID NO: 25 as determined using BlastP software of the National Center of Biotechnology Information (NCBI) using default parameters.

In another embodiment, the methods of the present invention provide a GLP-1 peptide having additionally at least one CTP amino acid peptide on the N-terminus and at least one CTP amino acid peptide on the C-terminus for treating or inhibiting type II diabetes. In another embodiment, the methods of the present invention provide a GLP-1 peptide having additionally one CTP amino acid peptide on the N-terminus and two CTP amino acid peptides on the C-terminus for treating or inhibiting type II diabetes. In another embodiment, the methods of the present invention provide a GLP-1 peptide set forth in SEQ ID NO: 25 having additionally at least one CTP amino acid peptide on the N-terminus and at least one CTP amino acid peptide on the C-terminus for treating or inhibiting type II diabetes.

In one embodiment, the homologue also refers to a deletion, insertion, or substitution variant, including an amino acid substitution thereof, and biologically active polypeptide fragments thereof.

In one embodiment the polypeptide sequence of interest is an EPO. In one embodiment, the polypeptide sequence of interest is an interferon. In another embodiment, the polypeptide sequence of interest is an hGH. In another embodiment, the polypeptide sequence of interest is a GLP-1. In another embodiment the polypeptide sequence of interest is an insulin. In another embodiment, the polypeptide sequence of interest is enkephalin. In another embodiment, the polypeptide sequence of interest is an ACTH. In another, embodiment the polypeptide sequence of interest is a glucagon. In another embodiment, the polypeptide sequence of interest is an insulin-like growth factor. In another embodiment, the polypeptide sequence of interest is an epidermal growth factor. In another embodiment, the polypeptide sequence of interest is an acidic or basic fibroblast growth factor. In another embodiment, the polypeptide sequence of interest is a platelet-derived growth factor. In another embodiment, the polypeptide sequence of interest is a granulocyte-CSF. In another embodiment, the polypeptide sequence of interest is a macrophage-CSF. In another embodiment, the polypeptide sequence of interest is an IL-2. In another embodiment, the polypeptide sequence of interest is an IL-3. In another embodiment, the polypeptide sequence of interest is a tumor necrosis factor. In another embodiment, the polypeptide sequence of interest is an LHRH. In another embodiment, the polypeptide sequence of interest is an LHRH analog. In another embodiment, the polypeptide sequence of interest is a somatostatin. In another embodiment, the polypeptide sequence of interest is a growth hormone releasing factor. In another embodiment, the polypeptide sequence of interest is an endorphin. In another embodiment, the polypeptide sequence of interest is an alveolar surfactant protein. In another embodiment, the polypeptide sequence of interest is a natriuretic factor. In another embodiment, the polypeptide sequence of interest is an adhesion. In another embodiment, the polypeptide sequence of interest is an angiostatin. In another embodiment, the polypeptide sequence of interest is an endostatin. In another embodiment, the polypeptide sequence of interest is a receptor peptide. In another embodiment, the polypeptide sequence of interest is a receptor binding ligand. In another embodiment, the polypeptide sequence of interest is an antibody. In another embodiment, the polypeptide sequence of interest is an antibody fragment. In another embodiment, the polypeptide sequence of interest is a peptide or a protein including any modified form.

In another embodiment, the peptide of the invention comprises a peptide of interest having additionally at least one CTP amino acid peptide on the N-terminus and one CTP amino acid peptide on the C-terminus. In another embodiment, the peptide of interest having additionally at least one CTP amino acid peptide on the N-terminus and one CTP amino acid peptide on the C-terminus comprises a protein selected from the following list: insulin, Albutein/albumin, Activase® Alteplase/tPA, adenosine deaminase, immune globulin, glucocerebrosidase, Leukine-sargramostim/GM-CSF, G-CSF, Venoglobulin-S/IgG, Proleukin aldesleukin, DNase, Factor VIII, Helixate, L-asparaginase, WinRho SDF Rh I, Retavase retaplase/tPA, Factor IX, FSH, globulin, fibrin, interleukin-11, becaplermin/PDGF, lepirudin/herudin, TNF, Thymoglobulin, Factor VIa, interferon alpha-2a, interferon alfa n-1, interferon alfa-N3, interferon beta-1b, interferon gamma-1b, Interleukin-2, HGH, or monoclonal antibodies.

In another embodiment, the methods of the present invention provide insulin having additionally at least one CTP amino acid peptide on the N-terminus and one CTP amino acid peptide on the C-terminus for the treatment of diabetes.

In another embodiment, the methods of the present invention provide albumin having additionally at least one CTP amino acid peptide on the N-terminus and one CTP amino acid peptide on the C-terminus for the treatment of hypovolemic shock, hemodialysis or cardiopulmonary bypass.

In another embodiment, the methods of the present invention provide Activase®-Alteplase/tPA having additionally at least one CTP amino acid peptide on the N-terminus and one CTP amino acid peptide on the C-terminus for the treatment of acute myocardial infarction, acute massive pulmonary embolism, or ischemic stroke.

In another embodiment, the methods of the present invention provide adenosine deaminase having additionally at least one CTP amino acid peptide on the N-terminus and one CTP amino acid peptide on the C-terminus for the treatment of severe combined immunodeficiency disease.

In another embodiment, the methods of the present invention provide immune globulin having additionally at least one CTP amino acid peptide on the N-terminus and one CTP amino acid peptide on the C-terminus for the treatment of transplant recipients.

In another embodiment, the methods of the present invention provide CMV immune globulin. In another embodiment, the methods of the present invention provide glucocerebrosidase having additionally at least one CTP amino acid peptide on the N-terminus and one CTP amino acid peptide on the C-terminus for the treatment of Gaucher disease.

In another embodiment, the methods of the present invention provide Leukine-sargramostim/GM-CSF having additionally at least one CTP amino acid peptide on the N-terminus and one CTP amino acid peptide on the C-terminus for the Stimulation of hematopoietic progenitor cells.

In another embodiment, the methods of the present invention provide G-CSF having additionally at least one CTP amino acid peptide on the N-terminus and one CTP amino acid peptide on the C-terminus for the treatment of Neutropenia. In another embodiment, the methods of the present invention provide Venoglobulin-S/IgG having additionally at least one CTP amino acid peptide on the N-terminus and one CTP amino acid peptide on the C-terminus for the treatment of immunodeficiency diseases.

In another embodiment, the methods of the present invention provide Proleukin-aldesleukin having additionally at least one CTP amino acid peptide on the N-terminus and one CTP amino acid peptide on the C-terminus for the treatment of renal carcinoma or metastatic melanoma.

In another embodiment, the methods of the present invention provide DNase having additionally at least one CTP amino acid peptide on the N-terminus and one CTP amino acid peptide on the C-terminus for the treatment of cystic fibrosis.

In another embodiment, the methods of the present invention provide Factor VIII having additionally at least one CTP amino acid peptide on the N-terminus and one CTP amino acid peptide on the C-terminus for the treatment of Hemophilia A.

In another embodiment, the methods of the present invention provide helixate having additionally at least one CTP amino acid peptide on the N-terminus and one CTP amino acid peptide on the C-terminus for the treatment of Hemophilia A.

In another embodiment, the methods of the present invention provide L-asparaginase having additionally at least one CTP amino acid peptide on the N-terminus and one CTP amino acid peptide on the C-terminus for the treatment of acute lymphoblastic leukemia.

In another embodiment, the methods of the present invention provide WinRho SDF Rh IgG having additionally at least one CTP amino acid peptide on the N-terminus and one CTP amino acid peptide on the C-terminus for the treatment of Rh isoimmunization and immune thrombocytopenic purpura.

In another embodiment, the methods of the present invention provide Retavase retaplase/tPA having additionally at least one CTP amino acid peptide on the N-terminus and one CTP amino acid peptide on the C-terminus for the treatment of acute myocardial infarction.

In another embodiment, the methods of the present invention provide Factor IX having additionally at least one CTP amino acid peptide on the N-terminus and at least one CTP amino acid peptide on the C-terminus for the treatment of Hemophilia B.

In another embodiment, the methods of the present invention provide FSH having additionally at least one CTP amino acid peptide on the N-terminus and at least one CTP amino acid peptide on the C-terminus for stimulation of ovulation during assisted reproduction.

In another embodiment, the methods of the present invention provide globulin having additionally at least one CTP amino acid peptide on the N-terminus and at least one CTP amino acid peptide on the C-terminus for the prevention of respiratory syncytial virus disease.

In another embodiment, the methods of the present invention provide fibrin having additionally at least one CTP amino acid peptide on the N-terminus and at least one CTP amino acid peptide on the C-terminus for wound management and hemostasis. In another embodiment, the methods of the present invention provide interleukin-11 having additionally at least one CTP amino acid peptide on the N-terminus and at least one CTP amino acid peptide on the C-terminus for chemotherapy-induced thrombocytopenia.

In another embodiment, the methods of the present invention provide becaplermin/PDGF having additionally at least one CTP amino acid peptide on the N-terminus and at least one CTP amino acid peptide on the C-terminus for the treatment of diabetic foot ulcers.

In another embodiment, the methods of the present invention provide lepirudin/herudin having additionally at least one CTP amino acid peptide on the N-terminus and at least one CTP amino acid peptide on the C-terminus for anticoagulation in heparin-induced thrombocytopenia.

In another embodiment, the methods of the present invention provide soluble TNF having additionally at least one CTP amino acid peptide on the N-terminus and at least one CTP amino acid peptide on the C-terminus for the treatment of rheumatoid arthritis.

In another embodiment, the methods of the present invention provide Thymoglobulin having additionally at least one CTP amino acid peptide on the N-terminus and at least one CTP amino acid peptide on the C-terminus for the treatment of organ transplant rejection disease.

In another embodiment, the methods of the present invention provide Factor VIIa having additionally at least one CTP amino acid peptide on the N-terminus and at least one CTP amino acid peptide on the C-terminus for the treatment of hemophilia.

In another embodiment, the methods of the present invention provide interferon alpha-2a having additionally at least one CTP amino acid peptide on the N-terminus and at least one CTP amino acid peptide on the C-terminus for the treatment of hairy cell leukemia and AIDS-related Kaposi's sarcoma.

In another embodiment, the methods of the present invention provide interferon alpha-2b having additionally at least one CTP amino acid peptide on the N-terminus and at least one CTP amino acid peptide on the C-terminus for the treatment of Hairy cell leukemia, genital warts, AIDS-related Kaposi's sarcoma, Hepatitis C, Hepatitis B, malignant melanoma, and follicular lymphoma.

In another embodiment, the methods of the present invention provide interferon alfa-N3 having additionally at least one CTP amino acid peptide on the N-terminus and at least one CTP amino acid peptide on the C-terminus for the treatment of genital warts.

In another embodiment, the methods of the present invention provide interferon gamma-1b having additionally at least one CTP amino acid peptide on the N-terminus and at least one CTP amino acid peptide on the C-terminus for the treatment of chronic granulomatous disease.

In another embodiment, the methods of the present invention provide interferon alfa n–1 having additionally at least one CTP amino acid peptide on the N-terminus and at least one CTP amino acid peptide on the C-terminus for the treatment of Hepatitis C infection.

In another embodiment, the methods of the present invention provide Interleukin-2 having additionally at least one CTP amino acid peptide on the N-terminus and at least one CTP amino acid peptide on the C-terminus for the treatment of renal carcinoma and metastatic melanoma.

In another embodiment, the methods of the present invention provide interferon beta-1b having additionally at least one CTP amino acid peptide on the N-terminus and at least one CTP amino acid peptide on the C-terminus for the treatment of multiple sclerosis.

In another embodiment, the methods of the present invention provide hGH having additionally at least one CTP amino acid peptide on the N-terminus and at least one CTP amino acid peptide on the C-terminus for the treatment of wasting disease, AIDS, cachexia, or hGH deficiency.

In another embodiment, the methods of the present invention provide an OKT3 monoclonal antibody having additionally at least one CTP amino acid peptide on the N-terminus and at least one CTP amino acid peptide on the C-terminus for organ transplant.

In another embodiment, the methods of the present invention provide a Reo monoclonal antibody having additionally at least one CTP amino acid peptide on the N-terminus and at least one CTP amino acid peptide on the C-terminus for prevention of complications from coronary intervention and angioplasty.

In another embodiment, the methods of the present invention provide a monoclonal antibody having additionally at least one CTP amino acid peptide on the N-terminus and at least one CTP amino acid peptide on the C-terminus for treating colorectal cancer, Non-Hodgkin's lymphoma, kidney transplant rejection, metastatic breast cancer, or the prevention of respiratory syncytial virus disease.

In one embodiment, the invention is employed in veterinary medicine. In one embodiment, the present invention provides treatment of domesticated mammals which are maintained as human companions (e.g., dogs, cats, horses), which have significant commercial value (e.g., dairy cows. beef cattle, sporting animals), which have significant scientific value (e.g., captive or free specimens of endangered species), or which otherwise have value.

In one embodiment, polypeptides, antibodies, or polynucleotides of the present invention are administered to an animal (e.g., mouse, rat, rabbit, hamster, guinea pig, pigs, micro-pig, chicken, camel, goat, horse, cow, sheep, dog, cat, non-human primate, and human). In one embodiment, the recited applications have uses in a wide variety of hosts. In some embodiments, such hosts include, but are not limited to, human, murine, rabbit, goat, guinea pig, camel, horse, mouse, rat, hamster, pig, micro-pig, chicken, goat, cow, sheep, dog, cat, or non-human primate.

In one embodiment, farm animals are treated by the methods of the present invention. In one embodiment, farm animals include pigs, cattle, dairy cows, horses, goats, sheep, chickens, turkeys, geese, ducks and related species. In one embodiment, laboratory animals are treated by the methods of the present invention. In one embodiment, laboratory animals include rats, mice, guinea pigs, rabbits, goats, monkeys, dogs, cats and others. In one embodiment, zoo animals are treated by the methods of the present invention. In one embodiment, zoo animals include all vertebrate animals kept in zoos. In one embodiment, aquatic animals are treated by the methods of the present invention. In one embodiment, aquatic animals include fish, eels, turtles, seals, penguins, sharks, whales, and related species. In one embodiment, domesticated animals are treated by the methods of the present invention. In one embodiment, domesticated animals include any pet, such as cats and dogs, or animal that is kept by humans, e.g., horses, cattle, pigs, goats, rabbits, chickens, turkeys, geese, ducks and the like.

According to the present invention the term pigs includes pigs, piglets, hogs, gilts, barrows, boars and sows. In another embodiment, "cattle" refers to calves, cows, dairy cows, heifers, steers and bulls.

In one embodiment, bovine growth hormone is utilized by the methods of the present invention. In one embodiment, artificial bovine growth hormone is utilized by the methods of the present invention. In one embodiment, the artificial bovine growth hormone has a sequence set forth in NCBI sequence ID number AAA72262. In another embodiment, the artificial bovine growth hormone is any other artificial bovine growth hormone known in the art. Each possibility represents a separate embodiment of the present invention.

In one embodiment, sheep growth hormone is utilized by the methods of the present invention. In one embodiment, sheep growth hormone has a sequence set forth in NCBI sequence ID number NP_001009315. In another embodiment, the sheep growth hormone is any other sheep growth hormone known in the art. Each possibility represents a separate embodiment of the present invention.

In one embodiment, horse growth hormone is utilized by the methods of the present invention. In one embodiment, horse growth hormone has a sequence set forth in NCBI sequence ID number AAA21027. In another embodiment, the horse growth hormone is any other horse growth hormone known in the art. Each possibility represents a separate embodiment of the present invention.

In one embodiment, chicken growth hormone is utilized by the methods of the present invention. In one embodiment, chicken growth hormone has a sequence set forth in NCBI sequence ID number CAA3561. In another embodiment, the chicken growth hormone is any other chicken growth hormone known in the art. Each possibility represents a separate embodiment of the present invention.

In one embodiment, murine growth hormone is utilized by the methods of the present invention. In one embodiment, the murine growth hormone has a sequence set forth in NCBI sequence ID number NP_032143. In another embodiment, the murine growth hormone is any other murine growth hormone known in the art. Each possibility represents a separate embodiment of the present invention.

In one embodiment, tilapia growth hormone is utilized by the methods of the present invention. In one embodiment, the tilapia growth hormone has a sequence set forth in NCBI sequence ID number CAA00818. In another embodiment, the tilapia growth hormone is any other tilapia growth hormone known in the art. Each possibility represents a separate embodiment of the present invention.

In one embodiment, bovine EPO is utilized by the methods of the present invention. In one embodiment, artificial bovine growth hormone is utilized by the methods of the present invention. In one embodiment, artificial bovine growth hormone has a sequence set forth in NCBI sequence ID number NP_776334. In another embodiment, the bovine EPO is any other bovine EPO known in the art. Each possibility represents a separate embodiment of the present invention.

In one embodiment, pig EPO is utilized by the methods of the present invention. In one embodiment, pig EPO has a sequence set forth in NCBI sequence ID number NP_999299. In another embodiment, the pig EPO is any other pig EPO known in the art. Each possibility represents a separate embodiment of the present invention.

In one embodiment, sheep EPO is utilized by the methods of the present invention. In one embodiment, sheep growth hormone has a sequence set forth in NCBI sequence ID number NP_001019908. In another embodiment, the sheep growth hormone is any other sheep growth hormone known in the art. Each possibility represents a separate embodiment of the present invention.

In one embodiment, murine EPO is utilized by the methods of the present invention. In one embodiment, the murine growth hormone has a sequence set forth in NCBI sequence ID number CAA72707. In another embodiment, the murine growth hormone is any other murine growth hormone known in the art. Each possibility represents a separate embodiment of the present invention.

In one embodiment, bovine GLP-1 is utilized by the methods of the present invention. In one embodiment, bovine GLP-1 has a sequence set forth in NCBI sequence ID number P01272. In another embodiment, the bovine GLP-1 is any other bovine GLP-1 known in the art. Each possibility represents a separate embodiment of the present invention.

In one embodiment, sheep GLP-1 is utilized by the methods of the present invention. In one embodiment, sheep GLP-1 has a sequence set forth in NCBI sequence ID number Q8MJ25. In another embodiment, the sheep GLP-1 is any other sheep GLP-1 known in the art. Each possibility represents a separate embodiment of the present invention.

In one embodiment, pig GLP-1 is utilized by the methods of the present invention. In one embodiment, chicken GLP-1 has a sequence set forth in NCBI sequence ID number P01274. In another embodiment, the chicken GLP-1 is any other chicken GLP-1 known in the art. Each possibility represents a separate embodiment of the present invention.

In one embodiment, murine GLP-1 is utilized by the methods of the present invention. In one embodiment, the murine GLP-1 has a sequence set forth in NCBI sequence ID number NP_032127. In another embodiment, the murine GLP-1 is any other murine GLP-1 known in the art. Each possibility represents a separate embodiment of the present invention.

In one embodiment, bovine interferon alpha is utilized by the methods of the present invention. In one embodiment, bovine interferon alpha has a sequence set forth in NCBI sequence ID number ABD57311. In another embodiment, the bovine interferon alpha is any other bovine interferon alpha known in the art. Each possibility represents a separate embodiment of the present invention.

In one embodiment, sheep interferon alpha is utilized by the methods of the present invention. In one embodiment, sheep interferon alpha has a sequence set forth in NCBI sequence ID number CAA41790. In another embodiment, the sheep interferon alpha is any other sheep interferon alpha known in the art. Each possibility represents a separate embodiment of the present invention.

In one embodiment, pig interferon alpha is utilized by the methods of the present invention. In one embodiment, chicken interferon alpha has a sequence set forth in NCBI sequence ID number AAP92118. In another embodiment, the pig interferon alpha is any other pig interferon alpha known in the art. Each possibility represents a separate embodiment of the present invention.

In one embodiment, murine interferon alpha is utilized by the methods of the present invention. In one embodiment, murine interferon alpha has a sequence set forth in NCBI sequence ID number AAA37886. In another embodiment, the murine interferon alpha is any other murine interferon alpha known in the art. Each possibility represents a separate embodiment of the present invention.

In some embodiments, the CTP sequence modification is advantageous in permitting lower dosages to be used.

In some embodiments, "polypeptide" as used herein encompasses native polypeptides (either degradation products, synthetically synthesized polypeptides or recombinant polypeptides) and peptidomimetics (typically, synthetic polypeptides), as well as peptoids and semipeptoids which are polypeptide analogs, which have, in some embodiments, modifications rendering the polypeptides even more stable while in a body or more capable of penetrating into cells.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinbelow.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by (x-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, be substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid" is understood to include the 20 naturally occurring amino acids; those amino acid often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. In one embodiment, "amino acid" includes both D- and L-amino acids.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the polypeptides of the present invention are utilized in a linear form, although it will be appreciated by one skilled in the art that in cases where cyclicization does not severely interfere with polypeptide characteristics, cyclic forms of the polypeptide can also be utilized.

In some embodiments, the polypeptides of present invention are biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides are purified by preparative high performance liquid chromatography [Creighton T. (1983) Proteins, structures and molecular principles. WH Freeman and Co. N.Y.], the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acids). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In one embodiment, a polypeptide of the present invention is synthesized using a polynucleotide encoding a polypeptide of the present invention. In some embodiments, the polynucleotide encoding a polypeptide of the present invention is ligated into an expression vector, comprising a transcriptional control of a cis-regulatory sequence (e.g., promoter sequence). In some embodiments, the cis-regulatory sequence is suitable for directing constitutive expression of the polypeptide of the present invention. In some embodiments, the cis-regulatory sequence is suitable for directing tissue-specific expression of the polypeptide of the present invention. In some embodiments, the cis-regulatory sequence is suitable for directing inducible expression of the polypeptide of the present invention.

In some embodiments, polynucleotides which express the polypeptides of the present invention are as set forth in SEQ ID NOs: 20, 21, 44, 45 and 46.

In some embodiments, tissue-specific promoters suitable for use with the present invention include sequences which are functional in specific cell populations. Examples include, but are not limited to, promoters such as albumin that is liver specific [Pinkert et al., (1987) Genes Dev. 1:268-277], lymphoid-specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. U.S.A. 86:5473-5477], pancreas-specific promoters [Edlunch et al. (1985) Science 230: 912-916] or mammary gland-specific promoters such as the milk whey promoter (U.S. Pat. No. 4,873,316 and European Application Publication No. 264,166). Inducible promoters suitable for use with the present invention include for example the tetracycline-inducible promoter (Srour, M. A., et al., 2003. Thromb. Haemost. 90: 398-405).

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing there between. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In some embodiments, signal sequences include, but are not limited to the endogenous signal sequence for EPO as set forth in SEQ ID NO: 19 or the endogenous signal sequence for IFN-β1 as set forth in SEQ ID NO: 26. In another embodiment, the signal sequence is N-terminal to the CTP sequence that is in turn N-terminal to the polypeptide sequence of interest; e.g. the sequence is (a) signal sequence- (b) CTP- (c) sequence of interest- (d) optionally 1 or more additional CTP sequences. In another embodiment, 1 or more CTP sequences is inserted between the signal sequence of a polypeptide sequence of interest and the polypeptide sequence of interest itself, thus interrupting the wild-type sequence of interest. Each possibility represents a separate embodiment of the present invention.

In one embodiment, following expression and secretion, the signal peptides are cleaved from the precursor proteins resulting in the mature proteins.

In some embodiments, polynucleotides of the present invention are prepared using PCR techniques as described in Example 1, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhancers) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the polypeptide of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion proteins are engineered with a specific cleavage site to aid in recovery of the polypeptide. In one embodiment, vectors adaptable to such manipulation include, but are not limited to, the pET series of E. coli expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV, which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Barr virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, in vivo gene therapy using EPO has been attempted in animal models such as rodents [Bohl et al., Blood. 2000; 95:2793-2798], primates [Gao et al., Blood, 2004, Volume 103, Number 9] and has proven successful in human clinical trials for patients with chronic renal failure [Lippin et al Blood 2005, 106, Number 7].

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in $E.\ coli$; or retained on the outer surface of a cell or viral membrane.

In one embodiment, following a predetermined time in culture, recovery of the recombinant polypeptide is effected.

In one embodiment, the phrase "recovering the recombinant polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

In one embodiment, production of CTP-EPO-CTP polypeptides using recombinant DNA technology is illustrated in Example 1.

In some embodiments, the recombinant polypeptides are synthesized and purified; their therapeutic efficacy can be assayed either in vivo or in vitro. In one embodiment, the binding activities of the recombinant EPO polypeptides of the present invention can be ascertained using various assays as described in Examples 2-6 and 8-9. In one embodiment, in vitro binding activity is ascertained by measuring the ability of the polypeptide to stimulate proliferation of TF-1 cells. In one embodiment, in vivo activity is deduced by analyzing haematocrit levels (FIGS. 3-5) and/or as a percentage of reticulocytes.

In one embodiment, the EPO polypeptides of the present invention can be used to treat a subject, with a variety of erythropoietin-associated conditions. In some embodiments, a subject is a human subject.

In some embodiment, the phrase "erythropoietin-associated conditions" refers to any condition associated with below normal, abnormal, or inappropriate modulation of erythropoietin. In some embodiment, levels of erythropoietin associated with such conditions are determined by any measure accepted and utilized by those of skill in the art. In some embodiment, erythropoietin-associated conditions typically include anemic conditions.

In some embodiment, "anemic conditions" refers to any condition, disease, or disorder associated with anemia. In some embodiments, anemic conditions include, but are not limited to, aplastic anemia, autoimmune hemolytic anemia, bone marrow transplantation, Churg-Strauss syndrome, Diamond Blackfan anemia, Fanconi's anemia, Felty syndrome, graft versus host disease, hematopoietic stem cell transplantation, hemolytic uremic syndrome, myelodysplasic syndrome, nocturnal paroxysmal hemoglobinuria, osteomyelofibrosis, pancytopenia, pure red-cell aplasia, purpura Schoenlein-Henoch, sideroblastic anemia, refractory anemia with excess of blasts, rheumatoid arthritis, Shwachman syndrome, sickle cell disease, thalassemia major, thalassemia minor, thrombocytopenic purpura, etc.

In one embodiment, the present invention comprises CTP-hGH-CTP polypeptides. In one embodiment, recombinant DNA technology methods are used for the production of CTP-hGH-CTP polypeptides as illustrated in Example 7. In one embodiment, the therapeutic efficacy of the CTP-hGH-CTP polypeptides of the present invention is assayed in vivo. In one embodiment, the therapeutic efficacy of the CTP-hGH-CTP polypeptides of the present invention is assayed in vitro. In one embodiment, the binding activities of the recombinant hGH polypeptides of the present invention are measured using Nb2 (a prolactin-dependent rat lymphoma cell line (ECACC Cell Bank)) or a FCD-P1 murine cell line, previously transfected with human growth hormone receptor. In one embodiment, binding of hGH to these receptors induces cell proliferation which, in one embodiment, is measured by the levels of MTT cellular stain as a function of hGH activity. In one embodiment, in vivo activity is deduced by measuring weight gain over time in treated growth hormone-deficient animals.

In some embodiments, human growth hormone polypeptides of the present invention can be used to treat a subject, with conditions related to growth and weight, such as a growth deficiency disorder, AIDS wasting, aging, impaired immune function of HIV-infected subjects, a catabolic illness, surgical recovery, a congestive cardiomyopathy, liver transplantation, liver regeneration after hepatectomy, chronic renal failure, renal osteodystrophy, osteoporosis, achondroplasia/hypochondroplasia, skeletal dysplasia, a chronic inflammatory or nutritional disorder such as Crohn's disease, short bowel syndrome, juvenile chronic arthritis, cystic fibrosis, male infertility, X-linked hypophosphatemic rickets, Down's syndrome, Spina bifida, Noonan Syndrome, obesity, impaired muscle strength and fibromyalgia. In some embodiments, interferon polypeptides of the present invention are used to treat a subject, with a variety of conditions such as hairy cell leukemia (HCL), Kaposi's sarcoma (KS), chronic myelogenous leukemia (CML), chronic Hepatitis C(CHC), condylomata acuminata (CA), chronic Hepatitis B, malignant melanoma, follicular non-Hodgkin's lymphoma, multiple sclerosis, chronic granulomatous disease, *Mycobacterium avium* complex (MAC), pulmonary fibrosis and osteoporosis.

In some embodiments, Glucagon-like peptide-1 (GLP-1) polypeptides of the present invention are used to treat a subject with non-insulin dependent diabetes, obesity, stroke, myocardial infarction, stroke, stress-induced hyperglycemia, or irritable bowel syndrome.

In one embodiment, the polypeptides of the present invention can be provided to the individual per se. In one embodiment, the polypeptides of the present invention can be provided to the individual as part of a pharmaceutical composition where it is mixed with a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the polypeptide sequence of interest, which is accountable for the biological effect.

In some embodiments, any of the compositions of this invention will comprise at least two CTP sequences bound to a protein of interest, in any form. In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which can be used interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

Various embodiments of dosage ranges are contemplated by this invention. The dosage of the polypeptide of the present invention, in one embodiment, is in the range of 0.05-80 mg/day. In another embodiment, the dosage is in the range of 0.05-50 mg/day. In another embodiment, the dosage is in the range of 0.1-20 mg/day. In another embodiment, the dosage is in the range of 0.1-10 mg/day. In another embodiment, the dosage is in the range of 0.1-5 mg/day. In another embodiment, the dosage is in the range of 0.5-5 mg/day. In another embodiment, the dosage is in the range of 0.5-50 mg/day. In another embodiment, the dosage is in the range of 5-80 mg/day. In another embodiment, the dosage is in the range of 35-65 mg/day. In another embodiment, the dosage is in the range of 35-65 mg/day. In another embodiment, the dosage is in the range of 20-60 mg/day. In another embodiment, the dosage is in the range of 40-60 mg/day. In another embodiment, the dosage is in a range of 45-60 mg/day. In another embodiment, the dosage is in the range of 40-60 mg/day. In another embodiment, the dosage is in a range of 60-120 mg/day. In another embodiment, the dosage is in the range of 120-240 mg/day. In another embodiment, the dosage is in the range of 40-60 mg/day. In another embodiment, the dosage is in a range of 240-400 mg/day. In another embodiment, the dosage is in a range of 45-60 mg/day. In another embodiment, the dosage is in the range of 15-25 mg/day. In another embodiment, the dosage is in the range of 5-10 mg/day. In another embodiment, the dosage is in the range of 55-65 mg/day.

In one embodiment, the dosage is 20 mg/day. In another embodiment, the dosage is 30 mg/day. In another embodiment, the dosage is 40 mg/day. In another embodiment, the dosage is 50 mg/day. In another embodiment, the dosage is 60 mg/day. In another embodiment, the dosage is 70 mg/day. In another embodiment, the dosage is 80 mg/day. In another embodiment, the dosage is 90 mg/day. In another embodiment, the dosage is 100 mg/day.

Oral administration, in one embodiment, comprises a unit dosage form comprising tablets, capsules, lozenges, chewable tablets, suspensions, emulsions and the like. Such unit dosage forms comprise a safe and effective amount of the desired compound, or compounds, each of which is in one embodiment, from about 0.7 or 3.5 mg to about 280 mg/70 kg, or in another embodiment, about 0.5 or 10 mg to about 210 mg/70 kg. The pharmaceutically unacceptable carriers suitable for the preparation of unit dosage forms for peroral administration are well known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and crosscarmelose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, the compositions comprise from about 0.01% to about 10.0% w/v of a subject compound, more preferably from about 0.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention are formulated in conventional manner using one or more physiologically acceptable carriers comprising excipients and auxiliaries, which facilitate processing of the active ingredients into preparations which can be used pharmaceutically. In one embodiment, formulation is dependent upon the route of administration chosen.

In one embodiment, injectables of the invention are formulated in aqueous solutions. In one embodiment, injectables of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfite and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water-based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contains suitable stabilizers or agents which increase the solubility of the active ingredients to allow for the preparation of highly concentrated solutions.

In another embodiment, the active compound can be delivered in a vesicle, in particular a liposome (see Langer, *Science*

249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. *Biomed. Eng.* 14:201 (1987); Buchwald et al., Surgery 88:507 (1980); Saudek et al., *N. Engl. J. Med.* 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled release systems are discussed in the review by Langer (Science 249:1527-1533 (1990).

In some embodiments, the active ingredient is in powder form for constitution with a suitable vehicle, e.g., sterile, pyrogen-free water-based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of *theobroma*; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically acceptable carrier to be used in conjunction with the compound is basically determined by the way the compound is to be administered. If the subject compound is to be injected, in one embodiment, the pharmaceutically acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, crosscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of an effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also prepared, placed in an appropriate container, and labeled for treatment of an indicated condition.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the polypeptides of the present invention can be provided to the individual with additional active agents to achieve an improved therapeutic effect as compared to treatment with each agent by itself. In another embodiment, measures (e.g., dosing and selection of the complementary agent) are taken to minimize adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A Laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Example 1

Generation of EPO constructs

Materials and Methods:
Construction of expression vector pCI-dhfr: pCI-neo mammalian expression vector was purchased from Promega (Catalog No. E1841). The vector contains a CMV IE enhancer/promoter and neomycin phosphotransferase gene. The pSV2-dhfr clone was purchased from ATCC (Catalog No. 37146). The plasmid contains the murine dhfr gene. The construction of pCI-dhfr vector was performed as follows:
  a. The pSV2-dhfr plasmid was digested with restriction enzyme BglII (3' end of the dhfr gene). DNA polymerase I, Large (Klenow) Fragment was used to fill in the 5' overhangs to form blunt ends. The DNA was then digested with restriction enzyme AvrII (5' end of the dhfr gene). The dhfr gene (AvrII-blunt end) fragment was isolated.

b. The pCI-neo vector was digested with restriction enzyme BstXI (3' end of the neo gene). DNA polymerase I, Large (Klenow) Fragment was used to remove the 3' overhangs to form blunt ends. The DNA was then digested with restriction enzyme AvrII (5' end of the neo gene). The expression vector (AvrII—blunt end) was isolated.

c. The dhfr gene was ligated into pCI vector to form an expression vector containing the dhfr gene (pCI-dhfr).

Construction of hEPO-CTP variants: A cassette gene containing the C-Terminal peptide (CTP) of the beta subunit of hCG was fused to the coding sequence of human EPO(NP_000790.2) at different locations. Four EPO-CTP variants were constructed as illustrated in FIGS. 1A-D. The proEPO signal peptide was used for the construction of the secreted EPO-CTP variants. XbaI-NotI fragments containing Epo sequences were ligated into the pCI-dhfr expression vector of the present invention.

Table 2 hereinbelow summarizes the primer sequences used for constructing the CTP-containing polypeptides of the present invention.

EPO-3-p56-6 (Epo-3—SEQ ID NO: 3): Primers were purchased from Sigma-Genosys. A PCR reaction was performed using primer 15 (SEQ ID NO: 12) and primer $2^R$ (SEQ ID NO: 13) and plasmid DNA of pCI-dhfr-EPO-ctp x2 (701-2-p24-2) as a template. As a result of the PCR amplification, a 486 bp product was formed and ligated into TA cloning vector (Invitrogen, catalog K2000-01). Stu I-NotI fragment containing *Epo-ctp x2 sequence was isolated (209 bp).

Three sequential PCR reactions were performed. The first reaction was conducted with primer 1 (SEQ ID NO: 7) and primer $23^R$ (SEQ ID NO: 14) and plasmid DNA of pGT123-epo-ctp as a template; as a result of the PCR amplification, an 80 bp product was formed (signal peptide).

The second reaction was conducted with primer 24 (SEQ ID NO: 15) and primer $11^R$ (SEQ ID NO: 11) and plasmid DNA of 701-4-p42-1 as a template; as a result of the PCR amplification, a 610 bp product was formed.

The last reaction was conducted with primers 1 (SEQ ID NO: 7) and $11^R$ (SEQ ID NO: 11) and a mixture of the products of the previous two reactions as a template; as a result of the PCR amplification, a 700 bp product was formed and the XbaI-StuI fragment was isolated.

The two fragments (XbaI-StuI and StuI-NotI) were inserted into the eukaryotic expression vector pCI-dhfr (triple ligation) to yield the 701-3-p56-6 clone.

TABLE 2

| Primer number | SEQ ID NO | sequence | Restriction site (underlined in sequence) |
|---|---|---|---|
| 1 | 7 | 5' AA<u>TCTAGA</u>GGTCATCATGGGGGTGC 3' | XbaI |
| 2 | 8 | 5' ATT<u>GCGGCCGC</u>GGATCCAGAAGACCTTTATTG 3' | NotI |
| $17^R$ | 9 | 5' TA<u>AATATT</u>GGGGTGTCCGAGGGCCC 3' | SspI |
| 10 | 10 | 5' CC<u>AATATT</u>ACCACAAGCCCCACCACGCCTCAT 3' | SspI |
| $11^R$ | 11 | 5' T<u>GCGGCCGC</u>GGATCCTTATCTGTCCCCTGTCCTGC 3' | NotI |
| 15 | 12 | 5' GCCCTGCTGTCGGAAGC 3' | |
| $2^R$ | 13 | 5' ATT<u>GCGGCCGC</u>GGATCCAGAAGACCTTTATTG | NotI |
| $23^R$ | 14 | 5' CTTTGAGGAAGAGGAGCCCAGGACTGGGAGGC3' | |
| 24 | 15 | 5' CCTGGGCTCCTCTTCCTCAAAGGC 3' | |
| $28^R$ | 16 | 5' GCTTCCGACAGCAGGGC 3' | |

EPO-1 701-1-p17-6 (Epo-1—SEQ ID NO: 1): The XbaI-NotI 702 bp fragment was constructed by PCR using the above primers (SEQ ID NOs: 7-16). Then the XbaI-NotI PCR fragment containing Epo-ctp sequence was ligated into pCI-dhfr expression vector.

EPO-2 701-2-p24-2 (Epo-2—SEQ ID NO: 2): The XbaI/ApaI fragment (hGH-ctp) of pCI-dhfr-401-2-p21-2 (hGH-ctpx2) was replaced with the XbaI/ApaI fragment (EPO-ctp) of 701-1-p17-6 to create an Epo-ctpx2.

EPO-4-701-4-p42-1(Epo-4—SEQ ID NO: 4): First, a fragment from pCI-dhfr-EPO-ctp (701-1-p17-6) was constructed by PCR using primers 1 and 17 followed by XbaI/SspI digestion. This resulted in a fragment containing EPO and partial 5' CTP.

Secondly, a new fragment was constructed by overlapping PCR, on pGT123-hEpo as a template, using primer 10 and primer 11. SspI/NotI digestion resulted in a fragment containing 3' partial CTP and Epo.

The two fragments were ligated into pCI-dhfr to construct the p701-4-p42-1 clone.

EPO-5-p91-4 (Epo-5—SEQ ID NO: 5-(ctp-Epo): Primers were ordered from Sigma-Genosys. A PCR reaction was performed using primer 1 (SEQ ID NO: 7) and primer $11^R$ (SEQ ID NO: 11) and plasmid DNA of pCI-dhfr-ctp-EPO-ctp x2 (701-3-p56-6) as a template; as a result of the PCR amplification, a 670 bp product was formed and ligated into TA cloning vector (Invitrogen, catalog K2000-01). XbaI-NotI fragment containing ctp-Epo sequence was ligated into the eukaryotic expression vector pCI-dhfr to yield the 701-5-p91-4 clone.

EPO-6-p90-1 (Epo-6—SEQ ID NO: 6-(ctp-Epo-ctp): Three PCR reactions were performed. The first reaction was conducted with primer 1 (SEQ ID NO: 7) and primer $38^R$ (SEQ ID NO: 16) and plasmid DNA of 701-3-p56-6 as a template; as a result of the PCR amplification, a 400 bp product was formed.

The second reaction was conducted with primer 15 (SEQ ID NO: 12) and primer $2^R$ (SEQ ID NO: 13) and plasmid DNA of 701-1-p17-6 as a template; as a result of the PCR amplification, a 390 bp product was formed.

The last reaction was conducted with primers 1 (SEQ ID NO: 7) and $2^R$ (SEQ ID NO: 13) and a mixture of the products of the previous two reactions as a template; as a result of the PCR amplification, a 787 bp product was formed and ligated into a TA cloning vector (Invitrogen, catalog K2000-01). The XbaI-NotI fragment containing ctp-Epo-ctp sequence was ligated into the eukaryotic expression vector pCI-dhfr to yield the 701-6-p90-1 clone.

Example 2

Expression and Isolation of EPO-CTP Polypeptides

Materials and Methods

DNA transfection and clone selection: DG44 cells were transfected with pCI-DHFR expression vectors containing EPO-CTP variants using FuGENE6 Reagent (FuGENE Transfection Reagent—Roche Cat. 11 815 091 001). 48 hr following transfection, cells were diluted and seeded at 50-200 cells per well in a selective medium (CD DG44 Medium w/o HT (Gibco: Scotland part: #07990111A) Sku num.: ME060027 supplemented with 8 mM L-Glutamine Biological Industries: Cat: 03-020-1A) and 18 mL/L of 10% Pluronic F-68 solution (Gibco: Cat: 240040-032). Selected clones were screened for highest protein production using commercial ELISA. Three to five producing clones per each variant were frozen for a backup cell bank. A selected clone for each variant was adapted to growth in larger scale cultures up to 1L flasks on an orbital shaker platform. Supernatants were collected and analyzed by ELISA, SDS-PAGE and Western blot. Following the withdrawal of aliquots, the protein-containing supernatants were kept frozen until further use.

Cell culture: DG44 cells were maintained in DG44 medium with HT (cat# 12610-010, Gibco) supplemented with 8 mM L-Glutamine (Biological Industries: Cat: 03-020-1A) and 18 mL/L of 10% Pluronic F-68 solution (Gibco: Cat: 240040-032), at 37° C. in a humidified 8% $CO_2$ incubator. Transfected clones were maintained in DG44 basal medium without HT supplement, hypoxanthine and thymidine, with pluronic acid and L-glutamine.

Sample preparation: Supernatants were collected, filtrated and analyzed by ELISA to determine protein concentration. SDS-PAGE and Western blot were used to determine purity and identity. Following ELISA, sample concentrations were defined and the solution was dialyzed against PBS. Following the withdrawal of aliquots, the protein-contained supernatants were kept frozen at −20° C. until further use.

Western Blotting Samples were electrophoresed on non-denaturing 15% SDS-polyacrylamide gels. Gels were allowed to equilibrate for 10 min in 25 mM Tris and 192 mM glycine in 20% (vol/vol) methanol). Proteins were transferred to a 0.2 μm pore size nitrocellulose membrane (Sigma, Saint Louis, Mo.) at 250 mA for 3 h, using a Mini Trans-Blot electrophoresis cell (Biorad Laboratories, Richmond, Calif.). The nitrocellulose membrane was incubated in 5% non-fat dry milk for 2 h at room temperature. The membrane was incubated with EPO anti-serum (1:1000 titer) overnight at 4° C. followed by three consecutive washes in PBS containing 0.1% Tween (10 min/wash). The membrane was incubated with secondary antibody conjugated to Horse Radish Peroxidase (HRP) (Zymed, San Francisco, Calif.) for 2 h at room temperature, followed by three washes. Finally, the nitrocellulose paper was reacted with enhanced chemiluminescent substrate (ECL) (Pierce, Rockford, Ill.) for 5 min, dried with a Whatman sheet, and exposed to X-ray film.

Results

Table 3 hereinbelow shows the concentrations of the various CTP-modified EPO forms obtained from 5 selected clones and their preparation for further testing.

TABLE 3

| #Version | # Clone | Stock Titer IU/ml[1] | Post dilution in Mock sup. according to Epo3 titer IU/ml[2] | Post ultrafiltration IU/ml[3] |
|---|---|---|---|---|
| Epo0 SEQ ID NO: 16 | 17 | 3093 | 102 | 335 |
| Epo1 SEQ ID NO: 1 | 47 | 1049 | 104 | 291 |
| Epo2 SEQ ID NO: 2 | 67 | 2160 | 110 | 303 |
| Epo3 SEQ ID NO: 3 | 85 | 105 | 119 | 392 |
| Epo4 SEQ ID NO: 4 | 112 | 6100 | ND | 342 |

[1]EPO variants stock concentration were determined by ELISA (Quantikine IVD Epo ELISA, DEP00, R&D Systems)
[2]Samples EPO-0, 1, 2 and 4 were diluted to 105 IU/ml in mock sup (Adjusted to Epo3 titer). Epo0 = wild type EPO expressed in the same system as the CTP modified EPOs
[3]All samples were concentrated and dialyzed by ultrafiltration against PBS to a final concentration of 180 IU/ml.

All proteins were detected by Western blot as illustrated in FIG. 2.

Example 3

Biological Activity of the EPO-CTP Polypeptides of the Present Invention

The TF-1 bioactivity test represents the ability of the EPO-CTP variant to bind its receptor and then stimulate activity which results in cell proliferation. Therefore, this test was used as a first step in evaluating the biological potency of the EPO-CTP polypeptides of the present invention.

Materials and Methods

Cell Proliferation Analysis: Proliferation assay was performed with the cell line TF-1, measuring levels of MTT cellular stain as a function of EPO activity (Kitamura et al., Kitamura, T. et al. (1989) *Establishment and characterization of a unique human cell line that proliferates*; Hammerling U. et al. In vitro bioassay for human erythropoietin based on proliferative stimulation of an erythroid cell line and analysis of carbohydrate-dependent microheterogeneity. Journal of Pharm. Biomed. Analysis 14(11): 1455-1469 (1996). Exponentially growing TF-1 cells were washed twice, plated at about $10^4$ cells/well in microtiter plates, and incubated in basal medium with a titrated dilution series of EPO (Recormon®), EPO standard (NIBSC standard), rhEPO (MOD-7010), MOD-701 variants (EPO-1, EPO-2, EPO-3 and EPO-4) for 48 hours. Four hours prior to assaying for cell proliferation, MTT reagent was added to the wells, and absorbance was measured by ELISA reader. A calculated protein concentration value for each variant protein was obtained from Eprex®'s (Epoetin (EPO)-man-made form of the human hormone) dose-response standard curve.

Results

The in vitro biological activity of EPO polypeptides was determined with an Epo-dependent cell line, human erythroleukemia TF-1 (DSMZ Cell Bank) [Dong et al., Biochemical and Biophysical Research Communications, Volume 339, Issue 1, 6 Jan. 2006, Pages 380-385]. The MTT assay was performed [Hammerling U. et al. In vitro bioassay for human erythropoietin based on proliferative stimulation of an erythroid cell line and analysis of carbohydrate-dependent microheterogeneity. Journal of Pharm. Biomed. Analysis 14(11): 1455-1469 (1996)], and the laboratory standard of EPO used to generate the standard curve was calibrated against the International Standard (Epo ampoule code 87/684 of NIBSC).

The results are summarized in Table 4 hereinbelow. The results indicate that the highest potency was achieved by using EPO 3 and EPO 0 in both 2 and 0.5 IU/ml concentrations.

TABLE 4

| Eprex STD IU/ml | TF-1 Bioactivity IU/ml | | | | | | |
|---|---|---|---|---|---|---|---|
| | EPO 0 SEQ ID NO: 16 | EPO 1 SEQ ID NO: 1 | EPO 2 SEQ ID NO: 2 | EPO 3 SEQ ID NO: 3 | EPO 4 SEQ ID NO: 4 | Recormon | EPO st |
| 2 | 4.93 | 2.32 | 2.13 | 6.91 | 3.55 | 3.44 | 7.40 |
| 0.5 | 1.60 | 0.76 | 0.53 | 1.34 | 0.84 | 0.87 | 1.53 |

Conclusion

As summarized in Table 4 hereinabove, different levels of potency were exerted by EPO-CTP polypeptides, indicating differences in receptor binding. EPO-CTP polypeptides differ by the number of CTP cassettes and the location to which they are fused. EPO-1 and EPO-2 contain 1 CTP sequence or 2 CTP sequences at the C-terminal of EPO, while EPO-3 contains 1 CTP at the N-terminal and 2 CTP sequences at the C-terminal. EPO-4 is a dimer of two EPO molecules linked by CTP sequence. EPO-3 demonstrated a potency level quite similar to WT-EPO, while EPO-1 and EPO-4 were about 50% less potent than WT-EPO, and EPO-2 potency was even less than 50%.

Example 4

Evaluation of the EPO-CTP Polypeptides of the Present Invention in a Mouse Model The following experiment was performed in order to compare the bio-activity of the EPO-CTP polypeptides of the present invention and commercial EPO.

Materials and Methods

| Animals: | |
|---|---|
| Species/Strain: | ICR or CD-1 Mice of either sex about 20-25 g |
| Group Size: | n = 7 |
| No. Groups: | 9 |
| Total No. Animals: | n = 63 |

Experimental design of the study: The experiment was set up as summarized in Table 5 hereinbelow.

TABLE 5

| Group No. | No. Mice per Group | TREATMENT | | Dosing |
|---|---|---|---|---|
| | | Compound | Dose Level | Regimen |
| 1 | n = 7 | Vehicle (Control) | 0 | 1× weekly |
| 2 | | MOCK | | |
| 3 | | MOD-7010 | 15 µg/kg | |
| 4 | | MOD-7011 | | |
| 5 | | MOD-7012 | | |
| 6 | | MOD-7013 | | |
| 7 | | MOD-7014 | | |
| 8 | | Commercial | 15 µg/kg | |
| 9 | | rhEPO | 5 µg/kg | 3× weekly |

Animal treatment: All animals were administered with either control or the test EPO polypeptides of the present invention by bolus injection. The injection volume did not exceed 10 ml/kg. The length of the experiment was 22 days. A morbidity and mortality check was performed daily.

Reticulocyte count and hematocrit (hct) examination: Reticulocyte count was carried out in all test animals at day 2 and 14 hrs following the 1st respective vehicle or treatment injection. HCT was determined in all animals once prior to initial treatment ("0" Baseline control) and at 24 hrs after the 1st respective vehicle or treatment injection, and thereafter twice weekly until study termination (Day 22).

Results

Figure 4:
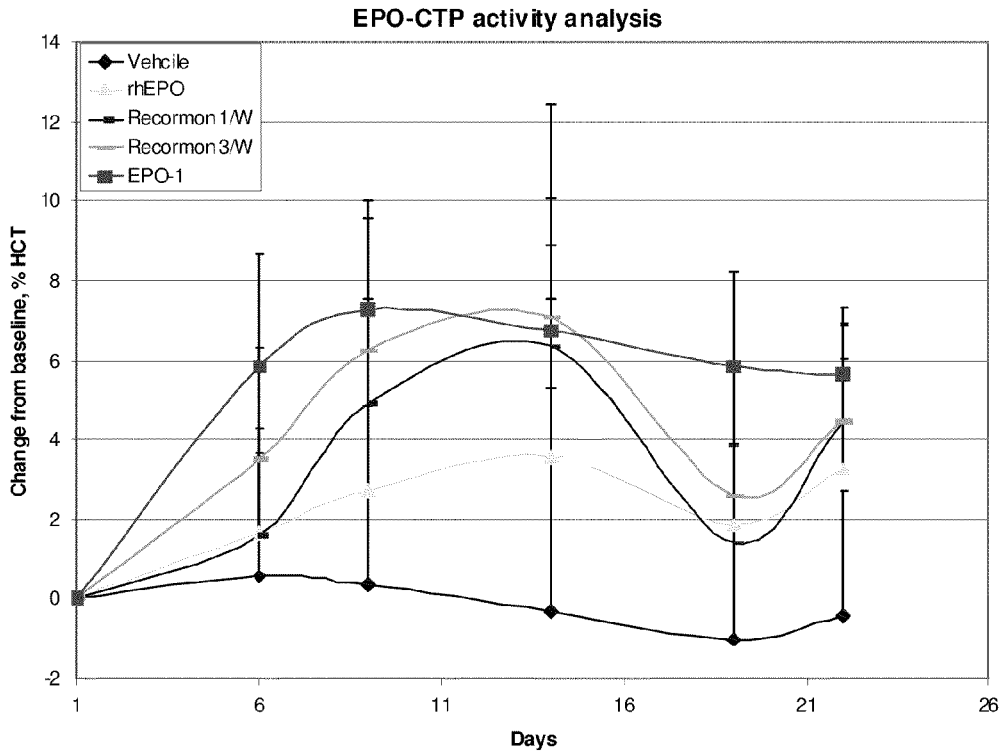
FIG. 4 is a graph illustrating the in vivo bioactivity of recombinant hEPO derivatives and EPO-1 (SEQ ID NO: 1). ICR mice (n=7/group) received a single i.v. injection/week (15 µg/kg) for three weeks of EPO-1, rhEPO-WT (SEQ ID NO: 16), Recormon® or Recormon® (5 µg/kg) 3 times a week. Control animals were injected i.v. with PBS. Blood samples were collected three times a week and haematocrit levels were detected. Each point represents the group average of haematocrit (%)±SE.
Figure 5:
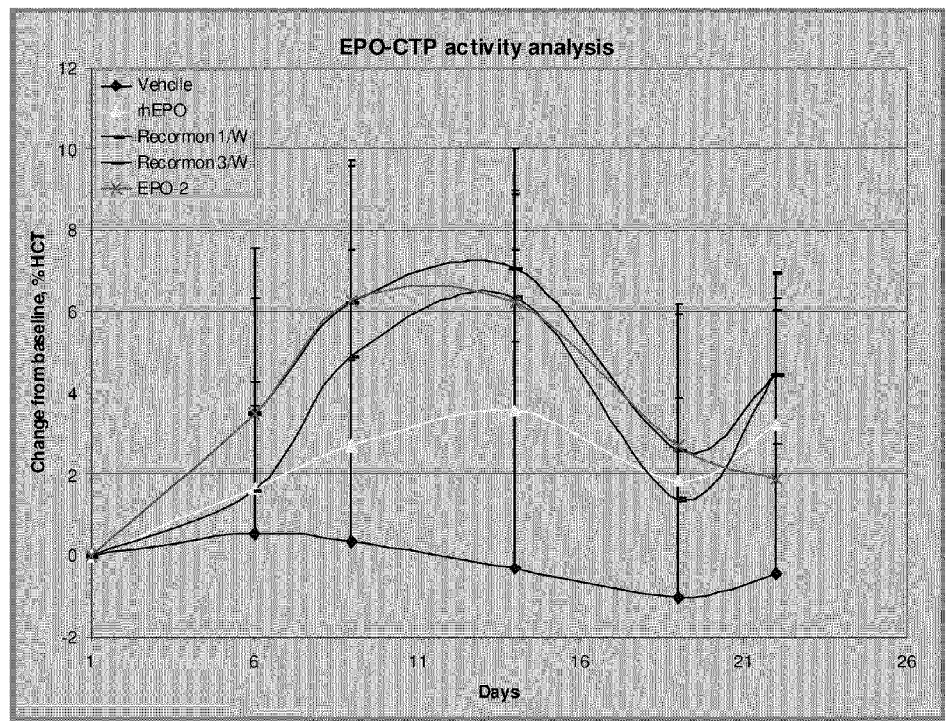
FIG. 5 is a graph illustrating the in vivo bioactivity of recombinant hEPO derivatives and EPO-2 (SEQ ID NO: 2). ICR mice (n=7/group) received a single i.v. injection/week (15 µg/kg) for three weeks of EPO-2 (SEQ ID NO: 2), rhEPO-WT (SEQ ID NO: 16), Recormon® or Recormon® (5 µg/kg) 3 times a week. Control animals were injected i.v. with PBS. Blood samples were collected three times a week and haematocrit levels were detected. Each point represents the group average of haematocrit (%)±SE.
Figure 6:
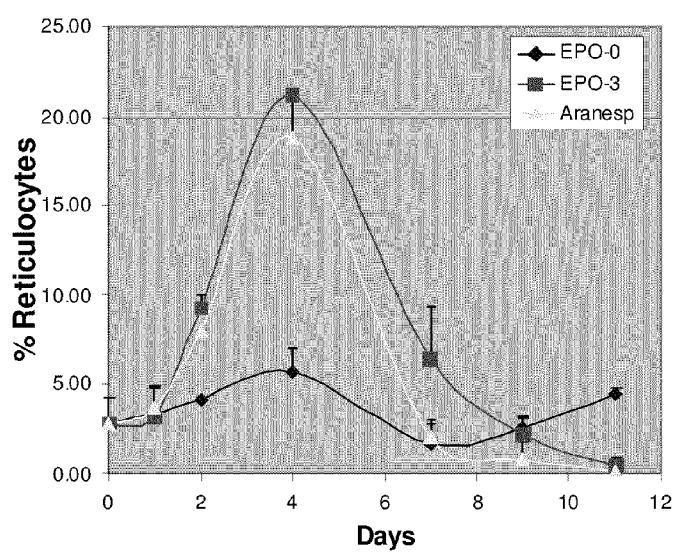
FIG. 6 is a time graph illustrating the change in reticulocyte level following a single bolus dose of EP0-0 (SEQ ID NO: 16), EPO-3 (SEQ ID NO: 3) and Aranesp®.
Figure 7:
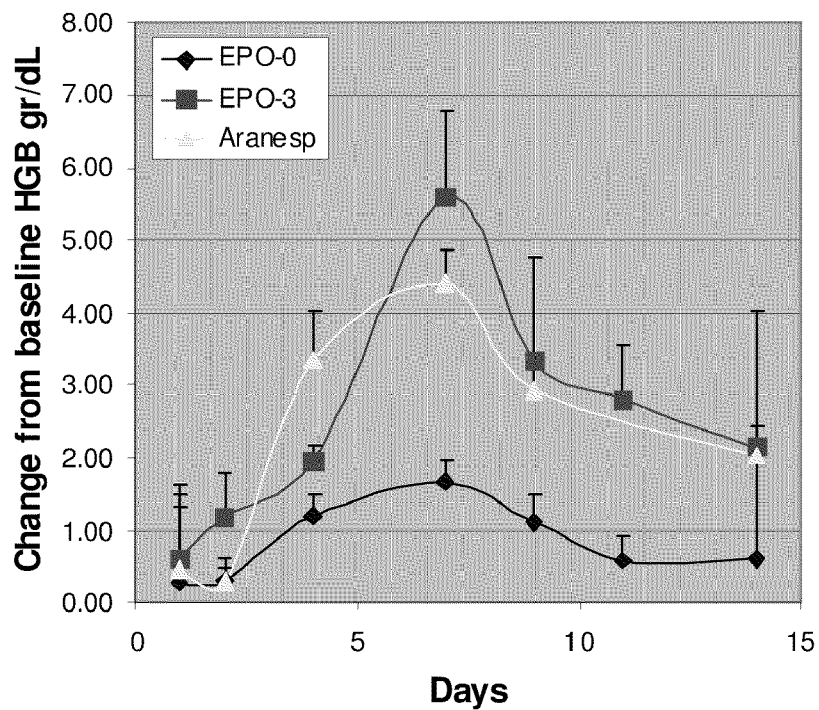
FIG. 7 is a time graph illustrating the change in hemoglobin level (presented as change from baseline) following a single bolus dose of EP0-0 (SEQ ID NO: 16), EPO-3 (SEQ ID NO: 3) and Aranesp®.
Figure 8:
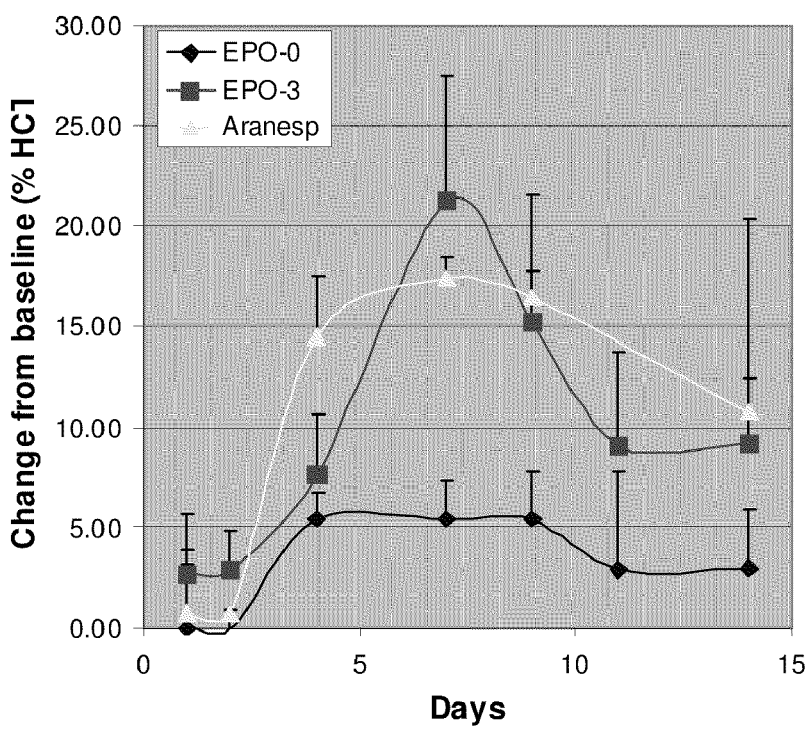
FIG. 8 is a time graph illustrating the change in hematocrit level following a single bolus dose of EP0-0 (SEQ ID NO: 16), EPO-3 (SEQ ID NO: 3) and Aranesp®.

The hematocrit results which are illustrated in FIGS. 3-5 show that EPO 3 has the highest hematocrit percentage change from baseline compared to EPO 1, EPO 2, Recormon® 1, Recormon® 3, rhEPO, and vehicle. The results demonstrating the percentage of reticulocytes in mice treated with the EPO-CTP polypeptides are summarized in Table 6 hereinbelow. These results show that EPO-3 is the most potent stimulator of erythropoiesis.

TABLE 6

| | % reticulocytes | |
|---|---|---|
| Days | 2 | 14 |
| Control | 3.72 | 3.46 |
| | 1.08 | 0.8 |
| Mock | 3.5 | 3.64 |
| | 0.6 | 1.13 |
| 7010 SEQ ID NO: 16 | 3.5 | 3.9 |
| | 0.6 | 1.54 |
| 7011 SEQ ID NO: 1 | 3.52 | 1.94 |
| | 1.38 | 1.08 |
| 7012 SEQ ID NO: 2 | 3.82 | 3.0 |
| | 1.02 | 0.88 |
| 7013 SEQ ID NO: 3 | 2.66 | 5.20 |
| | 0.97 | 2.96 |
| 7014 SEQ ID NO: 4 | 3.48 | 3.82 |
| | 0.71 | 0.90 |

TABLE 6-continued

|  | % reticulocytes | |
| --- | --- | --- |
| Days | 2 | 14 |
| Recormon 1/W | 3.23 | 3.27 |
|  | 0.73 | 0.59 |
| Recormon 3/w | 4.13 | 4.24 |
|  | 1.21 | 1.14 |

Conclusion

The in vivo experiment was designed to measure two parameters; the first was to measure erythropoiesis parameters such as percentage of reticulocytes and increase of hemoglobin, RBC and hematocrit levels. The second was to measure the durability of the biological activity of each variant by injecting once weekly doses.

A superior performance of EPO-3 in its ability to stimulate erythropoiesis was observed in normal mice.

Example 5

Comparison of the EPO-CTP Polypeptides of the Present Invention to Aranesp®

The following experiment was performed in order to compare the biological activity of a single bolus dose of some EPO-CTP polypeptides of the present invention, commercial EPO and Aranesp®. Aranesp® is a commercial long-acting recombinant erythropoietin in which two site mutations were introduced, resulting in two additional N-glycosylation sites and an increase in the number of incorporated sialic acid residues.

Materials and Methods

Animals:

Species/Strain: Female CD-1 Mice of either sex about 20-25 g

Group Size: n=3

Experimental design of the study: The experiment was set up as summarized in Table 7 hereinbelow.

TABLE 7

| Group # | Test Article | animals/ group/ time-point | Dose Solution Conc. (µg/mL) | Dose Volume (mL/kg) | Time-Points* (hours post-administration) |
| --- | --- | --- | --- | --- | --- |
| 1 | MOD-7010 SEQ ID NO: 11 | 3 | 1.5 | 10 | 0 (Pre-dose), 0.25, 0.5, 1, 2, 6, 24, 48, 96, 168, 216, 264 and 336 hr post-dose administration |
| 2 | MOD-7013 SEQ ID NO: 3 | 3 | 1.5 | 10 | 0.25, 0.5, 1, 2, 6, 24, 48, 96, 168, 216, 264 and 336 hr post-dose administration |
| 3 | Aranesp | 3 | 1.5 | 10 | 0.25, 0.5, 1, 2, 6, 24, 48, 96, 168, 216, 264 and 336 hr post-dose administration |

Animal treatment: All animals were administered with either control or the test EPO polypeptides of the present invention by bolus injection. The injection volume did not exceed 10 ml/kg. The length of the experiment was 14 days. A morbidity and mortality check was performed daily.

Reticulocyte count and hematocrit (hct) examination: Reticulocyte count and hematocrit examination were performed as described above.

Results

The results are illustrated in FIGS. 6-9. Following a single i.v. injection of 15 µg/kg of EPO 3, all three blood parameters associated with erythropoietin i.e. number of reticulocytes, hemoglobin level and hematocrit, were improved relative to those obtained with similar injected dose of rhEPO or Aranesp®.

Example 6

Comparison of the Pharmacokinetics of EPO-CTP Polypeptides of the Present Invention to Aranesp®

The following experiment was performed in order to compare the pharmacokinetics of EPO-CTP polypeptide of the present invention, commercial EPO and Aranesp®.

Materials and Methods

Serum samples were analyzed in order to determine specific concentration levels for each sample. Concentration and time-point data were processed using WinNonLin noncompartmental analysis. Parameters determined included: AUC, CL, Ke, $t_{1/2}$, Cmax, $T_{max}$, and Vdz.

Serum concentrations were determined using two ELISA kits in parallel. EPO-3 serum concentration was measured using StemCell ELISA kit in comparison to EPO-0 and Aranesp® serum concentration which were determined using R&D system ELISA kit.

Results

The results of the pharmacokinetic analysis are summarized in Table 8, hereinbelow. These results show that EPO 3 exhibited favorable pharmacokinetic measures as indicated for example in AUC measures, $t_{1/2}$, and Cmax. Tmax measures were equal to EPO-0, EPO-3, and Aranesp®.

TABLE 8

| Parameters | Units | EPO-0 | EPO-3 | Aranesp |
| --- | --- | --- | --- | --- |
| AUClast | hr*mIU/mL | 31739 | 306072 | 178661 |
| CL | mL/hr/kg | 1.1152 | 0.2188 | 0.1207 |
| Ke | 1/hr | 0.157 | 0.0529 | 0.0639 |
| t½ | hr | 4.4139 | 13.1141 | 10.84 |
| Cmax | mIU/mL | 10766 | 16466 | 13266 |

TABLE 8-continued

| Parameters | Units | EPO-0 | EPO-3 | Aranesp |
| --- | --- | --- | --- | --- |
| Tmax | Hr | 0.25 | 0.25 | 0.25 |
| Vdz | mL/kg | 7.1017 | 4.1394 | 1.8877 |

Figure 9:
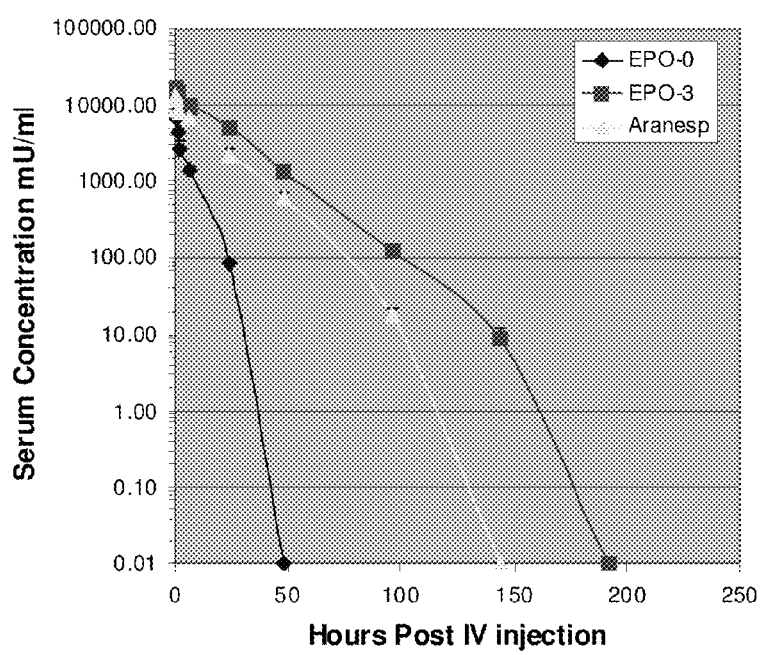
FIG. 9 is a graph illustrating the change in serum concentration of EPO-0 (SEQ ID NO: 16), EPO-3 (SEQ ID NO: 3) and Aranesp® post i.v. injection.

The results of the serum concentration analysis are illustrated in FIG. 9. These results show that EPO-3 was still detectable in the serum after about 190 hours. Both EPO-0 and Aranesp® were not detectable in the serum after about 140 hours and 50 hours, respectively.

Conclusion

Clearance of EPO-3 (MOD-7013) from the blood of CD-1 mice was significantly slower than that for rhEPO or Aranesp®. The corresponding calculated half-life times were: rhEPO—4.41 h; Aranesp®—0.84 h; and MOD-7013-13.11 h.

Example 7

Generation of hGH Constructs

Materials and Methods

Four hGH clones (variants of 20 kD protein) were synthesized. Xba I —Not I fragments containing hGH sequences from the four variants were ligated into the eukaryotic expression vector pCI-dhfr previously digested with XbaI —NotI. DNA from the 4 clones (401-0, 1, 2, 3 and 4) was prepared. Another partial hGH clone (1-242 bp) from 22 kD protein was also synthesized (0606114). Primers were ordered from Sigma-Genosys. The primer sequences used to generate the hGH-CTP polypeptides of the present invention are summarized in Table 9 hereinbelow.

TABLE 9

| Primer number | SEQ ID NO | sequence | Restriction site (underlined in sequence) |
|---|---|---|---|
| 25 | 27 | 5' <u>CTCTAGA</u>GGACATGGCCAC 3' | XbaI |
| $32^R$ | 28 | 5' ACAGGGAGGTCTGGGGGTTCT GCA 3' | |
| 33 | 29 | 5' TGCAGAACCCCCAGACCTCCC TGTGC 3' | |
| $4^R$ | 30 | 5' CCAAACTCATCAATGTATCTT A 3' | |
| 25 | 31 | 5' <u>CTCTAGA</u>GGACATGGCCAC 3' | XbaI |
| $35^R$ | 32 | 5' CGAACTCCTGGTAGGTGTCAA AGGC 3' | |
| 34 | 33 | 5' GCCTTTGACACCTACCAGGAG TTCG 3' | |
| $37^R$ | 34 | 5' <u>GCGGCCGC</u>ATCCAGACCTTC ATCACTGAGGC 3' | NotI |
| $39^R$ | 35 | 5' <u>GCGGCCGC</u>GGACTCATCAGAAGCC GCAGCTGCCC 3' | |

Construction of 402-0-p69-1 (hGH) SEQ ID NO: 36: MOD-4020 is the wild type recombinant human growth hormone (without CTP) which was prepared for use as control in the below described experiments.

Three PCR reactions were performed. The first reaction was conducted with primer 25 and primer $32^R$ and plasmid DNA of 0606114 (partial clone of hGH 1-242 bp) as a template; as a result of the PCR amplification, a 245 bp product was formed.

The second reaction was conducted with primer 33 and primer $4^R$ and plasmid DNA of 401-0-p57-2 as a template; as a result of the PCR amplification, a 542 bp product was formed.

The last reaction was conducted with primers 25 and $4^R$ and a mixture of the products of the previous two reactions as a template; as a result of the PCR amplification, a 705 bp product was formed and ligated into the TA cloning vector (Invitrogen, catalog K2000-01). The XbaI-NotI fragment containing hGH-0 sequence was ligated into the eukaryotic expression vector pCI-dhfr. The vector was transfected into DG-44 CHO cells. Cells were grown in protein-free medium.

Construction of 402-1-p83-5 (hGH-CTP)—SEQ ID NO: 37 and 402-2-p72-3(hGH-CTPx2)-SEQ ID NO: 38: MOD-4021 is a recombinant human growth hormone which was fused to 1 copy of the C-terminal peptide of the beta chain of human Chorionic Gonadotropin (CTP). The CTP cassette of MOD-4021 was attached to the C-terminus (one cassette). MOD-4022 is a recombinant human growth hormone which was fused to 2 copies of the C-terminal peptide of the beta chain of human Chorionic Gonadotropin (CTP). The two CTP cassettes of MOD-4022 were attached to the C-terminus (two cassettes).

Construction of hGH-CTP and hGH-CTP-CTP was performed in the same way as the construction of hGH-0. pCI-dhfr-401-1-p20-1 (hGH*-ctp) and pCI-dhfr-401-2-p21-2 (hGH*-ctp x2) were used as templates in the second PCR reaction.

Figure 10:
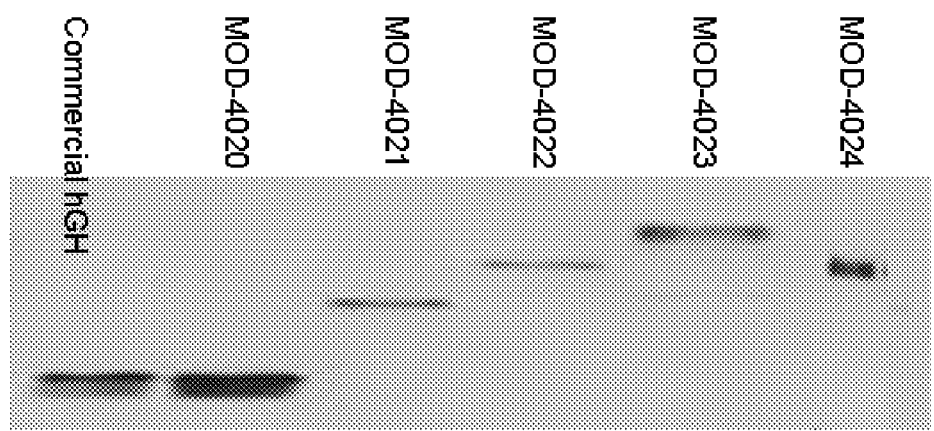
FIG. 10 is a Western blot illustrating the molecular weight & identity of MOD-4020 (SEQ ID NO: 36), MOD-4021 (SEQ ID NO: 37), MOD-4022 (SEQ ID NO: 38), MOD-4023 (SEQ ID NO: 39) and MOD-4024 (SEQ ID NO: 40). A pAGE SDS gel was blotted and stained using monoclonal anti-hGH antibodies. The photograph indicates that like commercial and wild type hGH, MOD-7020-4 variants are recognized by anti-hGH antibodies.

MOD-4021 and MOD-4022 were expressed in DG-44 CHO cells. Cells were grown in protein-free medium. The molecular weight of MOD-4021 is ~30.5 Kd since hGH has a MW of 22 Kd, while each "CTP cassette" contributes 8.5 Kd to the overall molecular weight (see FIG. 10). The molecular weight of MOD-4022 is ~39 Kd (see FIG. 10).

Construction of 402-3-p81-4 (CTP-hGH-CTP-CTP)—SEQ ID NO: 39 and 402-4-p82-9(CTP*hGH-CTP-CTP)—SEQ ID NO: 40: MOD-4023 is a recombinant human growth hormone which was fused to 3 copies of the C-terminal peptide of the beta chain of human Chorionic Gonadotropin (CTP). The three CTP cassettes of MOD-4023 were attached to both N-terminus (one cassette) and the C-terminus (two cassettes). MOD-4024 is a recombinant human growth hormone which is fused to 1 truncated and 2 complete copies of the C-terminal peptide of the beta chain of human Chorionic Gonadotropin (CTP). The truncated CTP cassette of MOD-4024 was attached to the N-terminus and two CTP cassettes were attached to the C-terminus (two cassettes).

Three PCR reactions were performed. The first reaction was conducted with primer 25 and primer $35^R$ and plasmid DNA of p401-3-p12-5 or 401-4-p22-1 as a template; as a result of the PCR amplification, a 265 or 220 bp product was formed. The second reaction was conducted with primer 34 and primer $37^R$ and plasmid DNA of TA-hGH-2-q65-1 as a template; as a result of the PCR amplification, a 695 bp product was formed. The last reaction was conducted with primers 25 and $37^R$ and a mixture of the products of the previous two reactions as a template; as a result of the PCR amplification, a 938 or 891 bp product was formed and ligated into TA cloning vector (Invitrogen, catalog K2000-01). Xba I —Not I fragment containing hGH sequence was ligated into our eukaryotic expression vector pCI-dhfr.

MOD-4023 and MOD-4024 were expressed in DG-44 CHO cells. Cells were grown in protein-free medium. The molecular weight of MOD-4023 is ~47.5 Kd (see FIG. 10) and the molecular weight of MOD-4024 is ~43.25 Kd (see FIG. 10).

Construction of 402-6-p95a-8 (CTP-hGH-CTP)—SEQ ID NO: 41: Construction of hGH-6 was performed in the same way as the construction of hGH-3. pCI-dhfr-402-1-p83-5 (hGH-ctp) was used as a template in the second PCR reaction.

Construction of 402-5-p96-4 (CTP-hGH)—SEQ ID NO: 42: A PCR reaction was performed using primer 25 and primer $39^R$ and plasmid DNA of pCI-dhfr-ctp-EPO-ctp (402-6-p95a-8) as a template; as a result of the PCR amplification, a 763 bp product was formed and ligated into TA cloning vector (Invitrogen, catalog K2000-01). Xba I -Not I fragment containing ctp-hGH sequence was ligated into our eukaryotic expression vector pCI-dhfr to yield 402-5-p96-4 clone.

Example 8

In vivo Bioactivity Tests of hGH-CTP Polypeptides of the Present Invention

The following experiment was performed in order to test the potential long acting biological activity of hGH-CTP polypeptides in comparison with commercial recombinant human GH and MOD-4020.

Materials and Methods

Female hypophysectomized rats (60-100 g) received a weekly s.c. injection of 21.7 μg hGH-CTP polypeptides or a once daily 5 μg s.c. injection of control commercial rhGH.

Weight was measured in all animals before treatment, 24 hours following first injection and then every other day until the end of the study on day 21. Each point represents the group's average weight gain percentage ((Weight day 0−weight last day)/Weight day 0). Average weight gain was normalized against once-daily injection of commercial hGH. The treatment schedule is summarized in Table 10.

TABLE 10

| No. | Drug | N | Route | Treatment Schedule | Equimolar Dose (μg/rat) | Accumulate Dosage (μg/rat) | Dose Vol. (ml) |
|---|---|---|---|---|---|---|---|
| 1 | Vehicle | 7 | s.c. | days 1, 7 and 13; 1/W | NA | NA | 0.25 |
| 2 | Mock | 7 | s.c | days 1, 7 and 13; 1/W | NA | NA | 0.25 |
| 3 | MOD-4020 SEQ ID NO: 36 | 7 | s.c | days 1, 7 and 13; 1/W | 21.7 | 65 | 0.25 |
| 4 | MOD-4021 SEQ ID NO: 37 | 7 | s.c. | days 1, 7 and 13; 1/W | 21.7 | 65 | 0.25 |
| 5 | MOD-4022 SEQ ID NO: 38 | 7 | s.c. | days 1, 7 and 13; 1/W | 21.7 | 65 | 0.25 |
| 6 | MOD-4023 SEQ ID NO: 39 | 7 | s.c. | days 1, 7 and 13; 1/W | 21.7 | 65 | 0.25 |
| 7 | MOD-4024 SEQ ID NO: 40 | 7 | s.c. | days 1, 7 and 13; 1/W | 21.7 | 65 | 0.25 |
| 8 | Commercial hGH v.1 | 7 | s.c. | days 1, 7 and 13; 1/W | 21.7 | 65 | 0.25 |
| 9 | Commercial hGH v.1 | 7 | s.c. | days 1-13; d/W | 5 | 65 | 0.25 |

Results

Results are summarized in FIG. 11. These results show that MOD-4023 (SEQ ID NO: 39) and MOD-4024 (SEQ ID NO: 40) induced over 120% weight gain compared to commercial rhGH which induced 100% weight gain.

Conclusion

Three weekly doses (Days of injections; 1, 7, and 13) of 21.7 μg of MOD-4023 (SEQ ID NO: 39) and MOD-4024 (SEQ ID NO: 40) induced a 30% greater weight increase in hypophysectomised rats compared to commercial rhGH injected at the same accumulated dose which was administered once per day at a dose of 5 μg for 13 days.

What is claimed is:

1. A polypeptide consisting of a non-human growth hormone polypeptide, one chorionic gonadotrophin carboxy terminal peptide attached to the amino terminus of said non-human growth hormone polypeptide, and two chorionic gonadotrophin carboxy terminal peptides attached to the carboxy terminus of said non-human growth hormone polypeptide.

2. The polypeptide of claim 1, wherein the sequence of at least a single chorionic gonadotrophin carboxy terminal peptide consists of an amino acid sequence selected from the group consisting of SEQ ID NO: 17 and SEQ ID NO: 18.

3. The polypeptide of claim 1, wherein at least a single chorionic gonadotrophin carboxy terminal peptide is truncated.

4. A composition comprising the polypeptide of claim 1 and a pharmaceutically acceptable carrier.

5. A polypeptide consisting of a non-human growth hormone polypeptide, one chorionic gonadotrophin carboxy terminal peptide attached to the amino terminus of said non-human growth hormone polypeptide, two chorionic gonadotrophin carboxy terminal peptides attached to the carboxy terminus of said non-human growth hormone polypeptide, and a signal peptide attached to the amino terminus of said one chorionic gonadotrophin carboxy terminal peptide.

6. The polypeptide of claim 5, wherein the sequence of said signal peptide is as set forth in SEQ ID NO: 19.

7. The polypeptide of claim 5, wherein the sequence of at least a single chorionic gonadotropin carboxy terminal peptide consists of an amino acid sequence selected from the group consisting of SEQ ID NO: 17 and SEQ ID NO: 18.

8. The polypeptide of claim 5, wherein at least a single chorionic gonadotrophin carboxy terminal peptide is truncated.

9. A composition comprising the polypeptide of claim 5 and a pharmaceutically acceptable carrier.

10. A method of extending the biological half life of a non-human growth hormone polypeptide, comprising the step of attaching one chorionic gonadotrophin carboxy terminal peptide to the amino terminus of said non-human growth hormone polypeptide and two chorionic gonadotrophin carboxy terminal peptides to the carboxy terminus of said non-human growth hormone polypeptide, thereby extending the biological half life of a non-human growth hormone polypeptide.

11. The method of claim 10, wherein the sequence of at least a single chorionic gonadotrophin carboxy tei iiiinal peptide consists of an amino acid sequence selected from the group consisting of: SEQ ID NO: 17 and SEQ ID NO: 18.

12. The method of claim 10, wherein at least a single chorionic gonadotrophin carboxy terminal peptide is truncated.

13. A method of extending the biological half life of a non-human growth hormone polypeptide, comprising the step of attaching one chorionic gonadotrophin carboxy terminal peptide to the amino terminus of said non-human growth hormone polypeptide and two chorionic gonadotrophin carboxy terminal peptides to the carboxy terminus of said non-human growth hormone polypeptide, and a signal peptide attached to the amino terminus of said one chorionic gonadotrophin carboxy terminal peptide, thereby extending the biological half life of a non-human growth hormone polypeptide.

14. The method of claim 13, wherein the sequence of at least a single chorionic gonadotrophin carboxy terminal peptide consists of an amino acid sequence selected from the group consisting of: SEQ ID NO: 17 and SEQ ID NO: 18.

15. The method of claim 13, wherein at least a single chorionic gonadotrophin carboxy terminal peptide is truncated.

16. The method of claim 13, wherein the sequence of said signal peptide is as set forth in SEQ ID NO: 19.

* * * * *

SEQUENCE LISTING

<160> NUMBER OF SEQ ID NOS: 47

<210> SEQ ID NO 1
<211> LENGTH: 221
<212> TYPE: PRT
<213> ORGANISM: Homo sapiens

<400> SEQUENCE: 1

Met Gly Val His Glu Cys Pro Ala Trp Leu Trp Leu Leu Leu Ser Leu
1               5                   10                  15

```
Leu Ser Leu Pro Leu Gly Leu Pro Val Leu Gly Ala Pro Arg Leu
         20                  25                  30

Ile Cys Asp Ser Arg Val Leu Glu Arg Tyr Leu Leu Glu Ala Lys Glu
             35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
             100                 105                 110

Gln Pro Trp Glu Pro Leu Gln Leu His Val Asp Lys Ala Val Ser Gly
         115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
             180                 185                 190

Arg Ser Ser Ser Ser Lys Ala Pro Pro Pro Ser Leu Pro Ser Pro Ser
         195                 200                 205

Arg Leu Pro Gly Pro Ser Asp Thr Pro Ile Leu Pro Gln
210                 215                 220

<210> SEQ ID NO 2
<211> LENGTH: 249
<212> TYPE: PRT
<213> ORGANISM: Homo sapiens

<400> SEQUENCE: 2

Met Gly Val His Glu Cys Pro Ala Trp Leu Trp Leu Leu Leu Ser Leu
1                5                  10                  15

Leu Ser Leu Pro Leu Gly Leu Pro Val Leu Gly Ala Pro Pro Arg Leu
             20                  25                  30

Ile Cys Asp Ser Arg Val Leu Glu Arg Tyr Leu Leu Glu Ala Lys Glu
         35                  40                  45

Ala Glu Asn Ile Thr Thr Gly Cys Ala Glu His Cys Ser Leu Asn Glu
 50                  55                  60

Asn Ile Thr Val Pro Asp Thr Lys Val Asn Phe Tyr Ala Trp Lys Arg
 65                  70                  75                  80

Met Glu Val Gly Gln Gln Ala Val Glu Val Trp Gln Gly Leu Ala Leu
                 85                  90                  95

Leu Ser Glu Ala Val Leu Arg Gly Gln Ala Leu Leu Val Asn Ser Ser
             100                 105                 110

Gln Pro Trp Glu Pro Leu Gln Leu His Val Asp Lys Ala Val Ser Gly
         115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175
```

```
Arg Gly Lys Leu Lys Leu Tyr Thr Gly Glu Ala Cys Arg Thr Gly Asp
            180                 185                 190
Arg Ser Ser Ser Lys Ala Pro Pro Ser Leu Pro Ser Pro Ser
        195                 200                 205
Arg Leu Pro Gly Pro Ser Asp Thr Pro Ile Leu Pro Gln Ser Ser Ser
    210                 215                 220
Ser Lys Ala Pro Pro Ser Leu Pro Ser Pro Ser Arg Leu Pro Gly
225                 230                 235                 240
Pro Ser Asp Thr Pro Ile Leu Pro Gln
                245

<210> SEQ ID NO 3
<211> LENGTH: 277
<212> TYPE: PRT
<213> ORGANISM: Homo sapiens

<400> SEQUENCE: 3

Met Gly Val His Glu Cys Pro Ala Trp Leu Trp Leu Leu Leu Ser Leu
1               5                   10                  15
Leu Ser Leu Pro Leu Gly Leu Pro Val Leu Gly Ser Ser Ser Ser Lys
            20                  25                  30
Ala Pro Pro Pro Ser Leu Pro Ser Pro Ser Arg Leu Pro Gly Pro Ser
        35                  40                  45
Asp Thr Pro Ile Leu Pro Gln Ala Pro Pro Arg Leu Ile Cys Asp Ser
    50                  55                  60
Arg Val Leu Glu Arg Tyr Leu Leu Glu Ala Lys Glu Ala Glu Asn Ile
65                  70                  75                  80
Thr Thr Gly Cys Ala Glu His Cys Ser Leu Asn Glu Asn Ile Thr Val
                85                  90                  95
Pro Asp Thr Lys Val Asn Phe Tyr Ala Trp Lys Arg Met Glu Val Gly
            100                 105                 110
Gln Gln Ala Val Glu Val Trp Gln Gly Leu Ala Leu Leu Ser Glu Ala
        115                 120                 125
Val Leu Arg Gly Gln Ala Leu Leu Val Asn Ser Ser Gln Pro Trp Glu
    130                 135                 140
Pro Leu Gln Leu His Val Asp Lys Ala Val Ser Gly Leu Arg Ser Leu
145                 150                 155                 160
Thr Thr Leu Leu Arg Ala Leu Gly Ala Gln Lys Glu Ala Ile Ser Pro
                165                 170                 175
Pro Asp Ala Ala Ser Ala Ala Pro Leu Arg Thr Ile Thr Ala Asp Thr
            180                 185                 190
Phe Arg Lys Leu Phe Arg Val Tyr Ser Asn Phe Leu Arg Gly Lys Leu
        195                 200                 205
Lys Leu Tyr Thr Gly Glu Ala Cys Arg Thr Gly Asp Arg Ser Ser Ser
    210                 215                 220
Ser Lys Ala Pro Pro Ser Leu Pro Ser Pro Ser Arg Leu Pro Gly
225                 230                 235                 240
Pro Ser Asp Thr Pro Ile Leu Pro Gln Ser Ser Ser Lys Ala Pro
                245                 250                 255
Pro Pro Ser Leu Pro Ser Pro Ser Arg Leu Pro Gly Pro Ser Asp Thr
            260                 265                 270
Pro Ile Leu Pro Gln
        275

<210> SEQ ID NO 4
```

```
<211> LENGTH: 387
<212> TYPE: PRT
<213> ORGANISM: Homo sapiens

<400> SEQUENCE: 4

Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
            20                  25                  30

Ile Cys Asp Ser Arg Val Leu Glu Arg Tyr Leu Leu Glu Ala Lys Glu
                35                  40                  45

Ala Glu Asn Ile Thr Thr Gly Cys Ala Glu His Cys Ser Leu Asn Glu
50                  55                      60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln Ala Pro Pro
210                 215                 220

Arg Leu Ile Cys Asp Ser Arg Val Leu Glu Arg Tyr Leu Leu Glu Ala
225                 230                 235                 240

Lys Glu Ala Glu Asn Ile Thr Thr Gly Cys Ala Glu His Cys Ser Leu
                245                 250                 255

Asn Glu Asn Ile Thr Val Pro Asp Thr Lys Val Asn Phe Tyr Ala Trp
            260                 265                 270

Lys Arg Met Glu Val Gly Gln Gln Ala Val Glu Val Trp Gln Gly Leu
        275                 280                 285

Ala Leu Leu Ser Glu Ala Val Leu Arg Gly Gln Ala Leu Leu Val Asn
290                 295                 300

Ser Ser Gln Pro Trp Glu Pro Leu Gln Leu His Val Asp Lys Ala Val
305                 310                 315                 320

Ser Gly Leu Arg Ser Leu Thr Thr Leu Leu Arg Ala Leu Gly Ala Gln
                325                 330                 335

Lys Glu Ala Ile Ser Pro Pro Asp Ala Ala Ser Ala Ala Pro Leu Arg
            340                 345                 350

Thr Ile Thr Ala Asp Thr Phe Arg Lys Leu Phe Arg Val Tyr Ser Asn
        355                 360                 365

Phe Leu Arg Gly Lys Leu Lys Leu Tyr Thr Gly Glu Ala Cys Arg Thr
370                 375                 380

Gly Asp Arg
385
```

<210> SEQ ID NO 5
<211> LENGTH: 221
<212> TYPE: PRT
<213> ORGANISM: Homo sapiens

<400> SEQUENCE: 5

Met Gly Val His Glu Cys Pro Ala Trp Leu Trp Leu Leu Ser Leu
1               5                   10                  15

Leu Ser Leu Pro Leu Gly Leu Pro Val Leu Gly Ser Ser Ser Lys
                20                  25                  30

Ala Pro Pro Ser Leu Pro Ser Pro Ser Arg Leu Pro Gly Pro Ser
            35                  40                  45

Asp Thr Pro Ile Leu Pro Gln Ala Pro Pro Arg Leu Ile Cys Asp Ser
        50                  55                  60

Arg Val Leu Glu Arg Tyr Leu Leu Glu Ala Lys Glu Ala Glu Asn Ile
65              70                  75                  80

Thr Thr Gly Cys Ala Glu His Cys Ser Leu Asn Glu Asn Ile Thr Val
                85                  90                  95

Pro Asp Thr Lys Val Asn Phe Tyr Ala Trp Lys Arg Met Glu Val Gly
                100                 105                 110

Gln Gln Ala Val Glu Val Trp Gln Gly Leu Ala Leu Leu Ser Glu Ala
            115                 120                 125

Val Leu Arg Gly Gln Ala Leu Leu Val Asn Ser Ser Gln Pro Trp Glu
130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

Phe Arg Lys Leu Phe Arg Val Tyr Ser Asn Phe Leu Arg Gly Lys Leu
        195                 200                 205

Lys Leu Tyr Thr Gly Glu Ala Cys Arg Thr Gly Asp Arg
    210                 215                 220

<210> SEQ ID NO 6
<211> LENGTH: 249
<212> TYPE: PRT
<213> ORGANISM: Homo sapiens

<400> SEQUENCE: 6

Met Gly Val His Glu Cys Pro Ala Trp Leu Trp Leu Leu Ser Leu
1               5                   10                  15

Leu Ser Leu Pro Leu Gly Leu Pro Val Leu Gly Ser Ser Ser Lys
                20                  25                  30

Ala Pro Pro Ser Leu Pro Ser Pro Ser Arg Leu Pro Gly Pro Ser
            35                  40                  45

Asp Thr Pro Ile Leu Pro Gln Ala Pro Pro Arg Leu Ile Cys Asp Ser
        50                  55                  60

Arg Val Leu Glu Arg Tyr Leu Leu Glu Ala Lys Glu Ala Glu Asn Ile
65              70                  75                  80

Thr Thr Gly Cys Ala Glu His Cys Ser Leu Asn Glu Asn Ile Thr Val
                85                  90                  95

Pro Asp Thr Lys Val Asn Phe Tyr Ala Trp Lys Arg Met Glu Val Gly
                100                 105                 110

Gln Gln Ala Val Glu Val Trp Gln Gly Leu Ala Leu Leu Ser Glu Ala
            115                 120                 125

Val Leu Arg Gly Gln Ala Leu Leu Val Asn Ser Ser Gln Pro Trp Glu
        130                 135                 140

Pro Leu Gln Leu His Val Asp Lys Ala Val Ser Gly Leu Arg Ser Leu
145                 150                 155                 160

Thr Thr Leu Leu Arg Ala Leu Gly Ala Gln Lys Glu Ala Ile Ser Pro
                165                 170                 175

Pro Asp Ala Ala Ser Ala Ala Pro Leu Arg Thr Ile Thr Ala Asp Thr
            180                 185                 190

Phe Arg Lys Leu Phe Arg Val Tyr Ser Asn Phe Leu Arg Gly Lys Leu
        195                 200                 205

Lys Leu Tyr Thr Gly Glu Ala Cys Arg Thr Gly Asp Arg Ser Ser Ser
210                 215                 220

Ser Lys Ala Pro Pro Pro Ser Leu Pro Ser Pro Ser Arg Leu Pro Gly
225                 230                 235                 240

Pro Ser Asp Thr Pro Ile Leu Pro Gln
            245

<210> SEQ ID NO 7
<211> LENGTH: 25
<212> TYPE: DNA
<213> ORGANISM: Artificial
<220> FEATURE:
<223> OTHER INFORMATION: Forward primer for EPO-CTP constructs

<400> SEQUENCE: 7
aatctagagg tcatcatggg ggtgc                                         25

<210> SEQ ID NO 8
<211> LENGTH: 32
<212> TYPE: DNA
<213> ORGANISM: Artificial
<220> FEATURE:
<223> OTHER INFORMATION: Forward primer for EPO-CTP constructs

<400> SEQUENCE: 8
attgcggccg cggatccaga agacctttat tg                                 32

<210> SEQ ID NO 9
<211> LENGTH: 25
<212> TYPE: DNA
<213> ORGANISM: Artificial
<220> FEATURE:
<223> OTHER INFORMATION: Reverse primer for EPO-CTP constructs

<400> SEQUENCE: 9
taaatattgg ggtgtccgag ggccc                                         25

<210> SEQ ID NO 10
<211> LENGTH: 32
<212> TYPE: DNA
<213> ORGANISM: Artificial
<220> FEATURE:
<223> OTHER INFORMATION: Forward primer for EPO-CTP constructs

<400> SEQUENCE: 10
ccaatattac cacaagcccc accacgcctc at                                 32

<210> SEQ ID NO 11
<211> LENGTH: 35
<212> TYPE: DNA
<213> ORGANISM: Artificial

```
<220> FEATURE:
<223> OTHER INFORMATION: Reverse primer for EPO-CTP constructs

<400> SEQUENCE: 11
tgcggccgcg gatccttatc tgtcccctgt cctgc                                35

<210> SEQ ID NO 12
<211> LENGTH: 17
<212> TYPE: DNA
<213> ORGANISM: Artificial
<220> FEATURE:
<223> OTHER INFORMATION: Forward primer for EPO-CTP constructs

<400> SEQUENCE: 12
gccctgctgt cggaagc                                                    17

<210> SEQ ID NO 13
<211> LENGTH: 32
<212> TYPE: DNA
<213> ORGANISM: Artificial
<220> FEATURE:
<223> OTHER INFORMATION: Reverse primer for EPO-CTP constructs

<400> SEQUENCE: 13
attgcggccg cggatccaga agacctttat tg                                   32

<210> SEQ ID NO 14
<211> LENGTH: 32
<212> TYPE: DNA
<213> ORGANISM: Artificial
<220> FEATURE:
<223> OTHER INFORMATION: Reverse primer for EPO-CTP constructs

<400> SEQUENCE: 14
ctttgaggaa gaggagccca ggactgggag gc                                   32

<210> SEQ ID NO 15
<211> LENGTH: 24
<212> TYPE: DNA
<213> ORGANISM: Artificial
<220> FEATURE:
<223> OTHER INFORMATION: Forward primer for EPO-CTP constructs

<400> SEQUENCE: 15
cctgggctcc tcttcctcaa aggc                                            24

<210> SEQ ID NO 16
<211> LENGTH: 17
<212> TYPE: DNA
<213> ORGANISM: Artificial Sequence
<220> FEATURE:
<223> OTHER INFORMATION: Reverse primer for EPO-CTP constructs

<400> SEQUENCE: 16
gcttccgaca gcagggc                                                    17

<210> SEQ ID NO 17
<211> LENGTH: 34
<212> TYPE: PRT
<213> ORGANISM: Artificial
<220> FEATURE:
<223> OTHER INFORMATION: CTP amino acid sequence

<400> SEQUENCE: 17

Asp Pro Arg Phe Gln Asp Ser Ser Ser Ser Lys Ala Pro Pro Pro Ser
 1               5                  10                  15
```

```
Leu Pro Ser Pro Ser Arg Leu Pro Gly Pro Ser Asp Thr Pro Ile Leu
            20                  25                  30

Pro Gln

<210> SEQ ID NO 18
<211> LENGTH: 28
<212> TYPE: PRT
<213> ORGANISM: Artificial
<220> FEATURE:
<223> OTHER INFORMATION: CTP amino acid sequence

<400> SEQUENCE: 18

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 19
<211> LENGTH: 27
<212> TYPE: PRT
<213> ORGANISM: Homo sapiens

<400> SEQUENCE: 19

Met Gly Val His Glu Cys Pro Ala Trp Leu Trp Leu Leu Ser Leu
1               5                   10                  15

Leu Ser Leu Pro Leu Gly Leu Pro Val Leu Gly
            20                  25

<210> SEQ ID NO 20
<211> LENGTH: 786
<212> TYPE: DNA
<213> ORGANISM: Homo sapiens

<400> SEQUENCE: 20
tctagaggtc atcatggggg tgcacgaatg tcctgcctgg ctgtggcttc tcctgtccct      60
tctgtcgctc cctctgggcc tcccagtcct gggctcctct tcctcaaagg cccctccccc    120
gagccttcca gtccatccc  gactcccggg gccctcggac accccaatat taccacaagc    180
cccaccacgc ctcatctgtg acagccgagt cctggagagg tacctcttgg aggccaagga    240
ggccgagaat atcacgacgg gctgtgctga cactgcagc  ttgaatgaga atatcactgt    300
cccagacacc aaagttaatt ctatgcctg  gaagaggatg gaggtcgggc agcaggccgt    360
agaagtctgg cagggcctgg ccctgctgtc ggaagctgtc ctgcggggcc aggccctgtt    420
ggtcaactct tcccagccgt gggagcccct gcagctgcat gtggataaag ccgtcagtgg    480
ccttcgcagc ctcaccactc tgcttcgggc tctgggagcc cagaaggaag ccatctcccc    540
tccagatgcg gcctcagctg ctccactccg aacaatcact gctgacactt tccgcaaact    600
cttccgagtc tactccaatt tcctccgggg aaagctgaag ctgtacacag ggaggcctg    660 caggacaggg gacagatcct cttcctcaaa ggcccctccc ccgagccttc caagtccatc    720
ccgactcccg ggccctcgg  acaccccgat cctcccacaa taaaggtctt ctggatccgc    780
ggccgc                                                                786

<210> SEQ ID NO 21
<211> LENGTH: 873
<212> TYPE: DNA
<213> ORGANISM: Homo sapiens

<400> SEQUENCE: 21
tctagaggtc atcatggggg tgcacgaatg tcctgcctgg ctgtggcttc tcctgtccct      60
```

```
tctgtcgctc cctctgggcc tcccagtcct gggctcctct tcctcaaagg cccctccccc      120
gagccttcca agtccatccc gactcccggg ccctcggac accccaatat taccacaagc       180
cccaccacgc ctcatctgtg acagccgagt cctggagagg tacctcttgg aggccaagga     240
ggccgagaat atcacgacgg gctgtgctga acactgcagc ttgaatgaga atatcactgt     300
cccagacacc aaagttaatt tctatgcctg gaagaggatg gaggtcgggc agcaggccgt     360
agaagtctgg cagggcctgg ccctgctgtc ggaagctgtc ctgcggggcc aggccctgtt     420
ggtcaactct tcccagccgt gggagcccct gcagctgcat gtggataaag ccgtcagtgg     480
ccttcgcagc ctcaccactc tgcttcgggc tctgggagcc cagaaggaag ccatctcccc     540
tccagatgcg gcctcagctg ctccactccg aacaatcact gctgacactt ccgcaaact      600 cttccgagtc tactccaatt tcctccgggg aaagctgaag ctgtacacag gggaggcctg    660
caggacaggg gacagatcct cttcctcaaa ggcccctccc ccgagccttc caagtccatc    720
ccgactcccg ggccctccg acaccaat cctgccacag agcagctcct ctaaggcccc     780
tcctccatcc ctgccatccc cctcccggct gcctggcccc tctgacaccc ctatcctgcc    840
tcagtgatga aggtcttctg gatccgcggc cgc                                 873
```

<210> SEQ ID NO 22
<211> LENGTH: 221
<212> TYPE: PRT
<213> ORGANISM: Homo sapiens

<400> SEQUENCE: 22

```
Met Gly Val His Glu Cys Pro Ala Trp Leu Trp Leu Leu Ser Leu
1               5                   10                  15

Leu Ser Leu Pro Leu Gly Leu Pro Val Leu Gly Ala Pro Arg Leu
                20                  25                  30

Ile Cys Asp Ser Arg Val Leu Glu Arg Tyr Leu Leu Glu Ala Lys Glu
                35                  40                  45

Ala Glu Asn Ile Thr Thr Gly Cys Ala Glu His Cys Ser Leu Asn Glu
        50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Ser Gln Ala Leu Leu Val Asn Ser Ser
                100                 105                 110

Gln Pro Trp Glu Pro Leu Gln Leu His Val Asp Lys Ala Val Ser Gly
                115                 120                 125

Leu Arg Ser Leu Thr Thr Leu Leu Arg Ala Leu Gly Ala Gln Lys Glu
        130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
                180                 185                 190

Arg Ser Ser Ser Lys Ala Pro Pro Ser Leu Pro Ser Pro Ser
        195                 200                 205

Arg Leu Pro Gly Pro Ser Asp Thr Pro Ile Leu Pro Gln
        210                 215                 220
```

```
<210> SEQ ID NO 23
<211> LENGTH: 217
<212> TYPE: PRT
<213> ORGANISM: Homo sapiens

<400> SEQUENCE: 23

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Val Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 24
<211> LENGTH: 166
<212> TYPE: PRT
<213> ORGANISM: Homo sapiens

<400> SEQUENCE: 24

Met Ser Tyr Asn Leu Leu Gly Phe Leu Gln Arg Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125
```

```
Ile Leu His Tyr Leu Lys Ala Lys Glu Tyr Ser His Cys Ala Trp Thr
    130                 135                 140
Ile Val Arg Val Glu Ile Leu Arg Asn Phe Tyr Phe Ile Asn Arg Leu
145                 150                 155                 160
Thr Gly Tyr Leu Arg Asn
                165

<210> SEQ ID NO 25
<211> LENGTH: 30
<212> TYPE: PRT
<213> ORGANISM: Homo sapiens

<400> SEQUENCE: 25

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg
            20                  25                  30

<210> SEQ ID NO 26
<211> LENGTH: 21
<212> TYPE: PRT
<213> ORGANISM: Homo sapiens

<400> SEQUENCE: 26

Met Thr Asn Lys Cys Leu Leu Gln Ile Ala Leu Leu Leu Cys Phe Ser
1               5                   10                  15
Thr Thr Ala Leu Ser
            20

<210> SEQ ID NO 27
<211> LENGTH: 19
<212> TYPE: DNA
<213> ORGANISM: Artificial
<220> FEATURE:
<223> OTHER INFORMATION: XbaI Forward primer for HGH-CTP constructs

<400> SEQUENCE: 27
ctctagagga catggccac                                            19

<210> SEQ ID NO 28
<211> LENGTH: 24
<212> TYPE: DNA
<213> ORGANISM: Artificial
<220> FEATURE:
<223> OTHER INFORMATION: Reverse primer for HGH-CTP constructs

<400> SEQUENCE: 28
acagggaggt ctgggggttc tgca                                      24

<210> SEQ ID NO 29
<211> LENGTH: 26
<212> TYPE: DNA
<213> ORGANISM: Artificial
<220> FEATURE:
<223> OTHER INFORMATION: Forward primer for HGH-CTP constructs

<400> SEQUENCE: 29
tgcagaaccc ccagacctcc ctgtgc                                    26

<210> SEQ ID NO 30
<211> LENGTH: 22
<212> TYPE: DNA
<213> ORGANISM: Artificial
<220> FEATURE:
```

```
-continued

<223> OTHER INFORMATION: Reverse primer for HGH-CTP constructs

<400> SEQUENCE: 30
ccaaactcat caatgtatct ta                                              22

<210> SEQ ID NO 31
<211> LENGTH: 19
<212> TYPE: DNA
<213> ORGANISM: Artificial
<220> FEATURE:
<223> OTHER INFORMATION: XbaI Forward primer for HGH-CTP constructs

<400> SEQUENCE: 31
ctctagagga catggccac                                                  19

<210> SEQ ID NO 32
<211> LENGTH: 25
<212> TYPE: DNA
<213> ORGANISM: Artificial
<220> FEATURE:
<223> OTHER INFORMATION: Reverse primer for HGH-CTP constructs

<400> SEQUENCE: 32
cgaactcctg gtaggtgtca aaggc                                           25

<210> SEQ ID NO 33
<211> LENGTH: 25
<212> TYPE: DNA
<213> ORGANISM: Artificial
<220> FEATURE:
<223> OTHER INFORMATION: Forward primer for HGH-CTP constructs

<400> SEQUENCE: 33
gcctttgaca cctaccagga gttcg                                           25

<210> SEQ ID NO 34
<211> LENGTH: 33
<212> TYPE: DNA
<213> ORGANISM: Artificial
<220> FEATURE:
<223> OTHER INFORMATION: NotI Reverse primer for HGH-CTP constructs

<400> SEQUENCE: 34
acgcggccgc atccagacct tcatcactga ggc                                  33

<210> SEQ ID NO 35
<211> LENGTH: 34
<212> TYPE: DNA
<213> ORGANISM: Artificial
<220> FEATURE:
<223> OTHER INFORMATION: Reverse primer for HGH-CTP constructs

<400> SEQUENCE: 35
gcggccgcgg actcatcaga agccgcagct gccc                                 34

<210> SEQ ID NO 36
<211> LENGTH: 217
<212> TYPE: PRT
<213> ORGANISM: Homo sapiens

<400> SEQUENCE: 36

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30
```

```
Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
210                 215

<210> SEQ ID NO 37
<211> LENGTH: 245
<212> TYPE: PRT
<213> ORGANISM: Homo sapiens

<400> SEQUENCE: 37

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
             20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
 50                  55                  60

Glu Gln Lys Tyr Ser Phe Leu Gln Asn Pro Gln Thr Ser Leu Cys Phe
 65                  70                  75                  80

Ser Glu Ser Ile Pro Thr Pro Ser Asn Arg Glu Glu Thr Gln Gln Lys
                 85                  90                  95

Ser Asn Leu Glu Leu Leu Arg Ile Ser Leu Leu Leu Ile Gln Ser Trp
                100                 105                 110

Leu Glu Pro Val Gln Phe Leu Arg Ser Val Phe Ala Asn Ser Leu Val
            115                 120                 125

Tyr Gly Ala Ser Asp Ser Asn Val Tyr Asp Leu Leu Lys Asp Leu Glu
130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190
```

```
Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
210                 215                 220

Pro Pro Ser Leu Pro Ser Pro Ser Arg Leu Pro Gly Pro Ser Asp Thr
225                 230                 235                 240

Pro Ile Leu Pro Gln
            245

<210> SEQ ID NO 38
<211> LENGTH: 273
<212> TYPE: PRT
<213> ORGANISM: Homo sapiens

<400> SEQUENCE: 38

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140

Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe Ser Ser Ser Lys Ala Pro
210                 215                 220

Pro Pro Ser Leu Pro Ser Pro Ser Arg Leu Pro Gly Pro Ser Asp Thr
225                 230                 235                 240

Pro Ile Leu Pro Gln Ser Ser Ser Lys Ala Pro Pro Pro Ser Leu
            245                 250                 255

Pro Ser Pro Ser Arg Leu Pro Gly Pro Ser Asp Thr Pro Ile Leu Pro
                260                 265                 270

Gln

<210> SEQ ID NO 39
<211> LENGTH: 301
<212> TYPE: PRT
<213> ORGANISM: Homo sapiens

<400> SEQUENCE: 39
```

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
    50                  55                  60

Asp Asn Ala Met Leu Arg Ala His Arg Leu His Gln Leu Ala Phe Asp
65                  70                  75                  80

Thr Tyr Gln Glu Phe Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
                100                 105                 110

Pro Thr Pro Ser Asn Arg Glu Glu Thr Gln Gln Lys Ser Asn Leu Glu
            115                 120                 125

Leu Leu Arg Ile Ser Leu Leu Leu Ile Gln Ser Trp Leu Glu Pro Val
        130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
    210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Pro Ser Leu
                245                 250                 255

Pro Ser Pro Ser Arg Leu Pro Gly Pro Ser Asp Thr Pro Ile Leu Pro
            260                 265                 270

Gln Ser Ser Ser Lys Ala Pro Pro Ser Leu Pro Ser Pro Ser
        275                 280                 285

Arg Leu Pro Gly Pro Ser Asp Thr Pro Ile Leu Pro Gln
    290                 295                 300

<210> SEQ ID NO 40
<211> LENGTH: 285
<212> TYPE: PRT
<213> ORGANISM: Homo sapiens

<400> SEQUENCE: 40

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Phe Pro Thr Ile Pro Leu Ser Arg Leu Phe
            35                  40                  45

Asp Asn Ala Met Leu Arg Ala His Arg Leu His Gln Leu Ala Phe Asp
    50                  55                  60

Thr Tyr Gln Glu Phe Glu Ala Tyr Ile Pro Lys Glu Gln Lys Tyr
65                  70                  75                  80
```

Ser Phe Leu Gln Asn Pro Gln Thr Ser Leu Cys Phe Ser Glu Ser Ile
                85                  90                  95

Pro Thr Pro Ser Asn Arg Glu Glu Thr Gln Gln Lys Ser Asn Leu Glu
            100                 105                 110

Leu Leu Arg Ile Ser Leu Leu Ile Gln Ser Trp Leu Glu Pro Val
        115                 120                 125

Gln Phe Leu Arg Ser Val Phe Ala Asn Ser Leu Val Tyr Gly Ala Ser
145                 150                 155                 160

Thr Leu Met Gly Arg Leu Glu Asp Gly Ser Pro Arg Thr Gly Gln Ile
                165                 170                 175

Phe Lys Gln Thr Tyr Ser Lys Phe Asp Thr Asn Ser His Asn Asp Asp
                180                 185                 190

Ala Leu Leu Lys Asn Tyr Gly Leu Leu Tyr Cys Phe Arg Lys Asp Met
            195                 200                 205

Asp Lys Val Glu Thr Phe Leu Arg Ile Val Gln Cys Arg Ser Val Glu
210                 215                 220

Gly Ser Cys Gly Phe Ser Ser Ser Lys Ala Pro Pro Ser Leu
225                 230                 235                 240

Pro Ser Pro Ser Arg Leu Pro Gly Pro Ser Asp Thr Pro Ile Leu Pro
                245                 250                 255

Gln Ser Ser Ser Ser Lys Ala Pro Pro Pro Ser Leu Pro Ser Pro Ser
            260                 265                 270

Arg Leu Pro Gly Pro Ser Asp Thr Pro Ile Leu Pro Gln
            275                 280                 285

<210> SEQ ID NO 41
<211> LENGTH: 273
<212> TYPE: PRT
<213> ORGANISM: Homo sapiens

<400> SEQUENCE: 41

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
        50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105                 110

Pro Thr Pro Ser Asn Arg Glu Glu Thr Gln Gln Lys Ser Asn Leu Glu
        115                 120                 125

Leu Leu Arg Ile Ser Leu Leu Leu Ile Gln Ser Trp Leu Glu Pro Val
    130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

-continued

```
Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
        210                 215                 220

Asp Lys Val Glu Thr Phe Leu Arg Ile Val Gln Cys Arg Ser Val Glu
225                 230                 235                 240

Gly Ser Cys Gly Phe Ser Ser Ser Lys Ala Pro Pro Ser Leu
            245                 250                 255

Pro Ser Pro Ser Arg Leu Pro Gly Pro Ser Asp Thr Pro Ile Leu Pro
            260                 265                 270

Gln

<210> SEQ ID NO 42
<211> LENGTH: 245
<212> TYPE: PRT
<213> ORGANISM: Homo sapiens

<400> SEQUENCE: 42

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Ser Ser Ser Lys Ala
            20                  25                  30

Pro Pro Pro Ser Leu Pro Ser Pro Ser Arg Leu Pro Gly Pro Ser Asp
            35                  40                  45

Thr Pro Ile Leu Pro Gln Phe Pro Thr Ile Pro Leu Ser Arg Leu Phe
        50                  55                  60

Asp Asn Ala Met Leu Arg Ala His Arg Leu His Gln Leu Ala Phe Asp
65                  70                  75                  80

Thr Tyr Gln Glu Phe Glu Glu Ala Tyr Ile Pro Lys Glu Gln Lys Tyr
                85                  90                  95

Ser Phe Leu Gln Asn Pro Gln Thr Ser Leu Cys Phe Ser Glu Ser Ile
            100                 105                 110

Pro Thr Pro Ser Asn Arg Glu Glu Thr Gln Gln Lys Ser Asn Leu Glu
        115                 120                 125

Leu Leu Arg Ile Ser Leu Leu Leu Ile Gln Ser Trp Leu Glu Pro Val
130                 135                 140

Gln Phe Leu Arg Ser Val Phe Ala Asn Ser Leu Val Tyr Gly Ala Ser
145                 150                 155                 160

Asp Ser Asn Val Tyr Asp Leu Leu Lys Asp Leu Glu Glu Gly Ile Gln
                165                 170                 175

Thr Leu Met Gly Arg Leu Glu Asp Gly Ser Pro Arg Thr Gly Gln Ile
            180                 185                 190

Phe Lys Gln Thr Tyr Ser Lys Phe Asp Thr Asn Ser His Asn Asp Asp
        195                 200                 205

Ala Leu Leu Lys Asn Tyr Gly Leu Leu Tyr Cys Phe Arg Lys Asp Met
        210                 215                 220

Asp Lys Val Glu Thr Phe Leu Arg Ile Val Gln Cys Arg Ser Val Glu
225                 230                 235                 240

Gly Ser Cys Gly Phe
            245

<210> SEQ ID NO 43
<211> LENGTH: 12
```

```
<212> TYPE: PRT
<213> ORGANISM: Artificial
<220> FEATURE:
<223> OTHER INFORMATION: CTP amino acid sequence

<400> SEQUENCE: 43

Ser Ser Ser Ser Lys Ala Pro Pro Pro Ser Leu Pro
1               5                   10

<210> SEQ ID NO 44
<211> LENGTH: 853
<212> TYPE: DNA
<213> ORGANISM: Homo sapiens

<400> SEQUENCE: 44
tctagaggac atggccaccg gcagcaggac cagcctgctg ctggccttcg gcctgctgtg       60
cctgccatgg ctgcaggagg gcagcgccag ctcttcttct aaggctccac ccccatctct      120
gcccagcccc agcagactgc cgggcccag cgacacaccc attctgcccc agttccccac       180 catcccctg agcaggctgt cgacaacgc catgctgagg gctcacaggc tgcaccagct        240
ggcctttgac acctaccagg agttcgagga agcctacatc cccaaggagc agaagtacag      300
cttcctgcag aaccccagat cctccctgtg cttcagcgag agcatcccca cccccagcaa      360
cagagaggag acccagcaga gagcaacct ggagctgctg aggatctccc tgctgctgat       420
ccagagctgg ctggagcccg tgcagttcct gagaagcgtg ttcgccaaca gcctggtgta      480
cggcgccagc gacagcaacg tgtacgacct gctgaaggac ctggaggagg catccagac      540 cctgatgggc cggctggagg acggcagccc caggaccggc cagatcttca gcagaccta      600 cagcaagttc gacaccaaca gccacaacga cgacgccctg ctgaagaact acgggctgct      660
gtactgcttc agaaaggaca tggacaaggt ggagaccttc ctgaggatcg tgcagtgcag      720
aagcgtggag ggcagctgcg gcttcagctc cagcagcaag gcccctcccc gagcctgcc      780 ctccccaagc aggctgcctg ggccctccga cacaccaatc tgcctcagt gatgaaggtc      840 tggatgcggc cgc                                                         853

<210> SEQ ID NO 45
<211> LENGTH: 937
<212> TYPE: DNA
<213> ORGANISM: Homo sapiens

<400> SEQUENCE: 45
tctagaggac atggccaccg gcagcaggac cagcctgctg ctggccttcg gcctgctgtg       60
cctgccatgg ctgcaggagg gcagcgccag ctcttcttct aaggctccac ccccatctct      120
gcccagcccc agcagactgc cgggcccag cgacacaccc attctgcccc agttccccac       180 catcccctg agcaggctgt cgacaacgc catgctgagg gctcacaggc tgcaccagct        240
ggcctttgac acctaccagg agttcgagga agcctacatc cccaaggagc agaagtacag      300
cttcctgcag aaccccagat cctccctgtg cttcagcgag agcatcccca cccccagcaa      360
cagagaggag acccagcaga gagcaacct ggagctgctg aggatctccc tgctgctgat       420
ccagagctgg ctggagcccg tgcagttcct gagaagcgtg ttcgccaaca gcctggtgta      480
cggcgccagc gacagcaacg tgtacgacct gctgaaggac ctggaggagg catccagac      540 cctgatgggc cggctggagg acggcagccc caggaccggc cagatcttca gcagaccta      600 cagcaagttc gacaccaaca gccacaacga cgacgccctg ctgaagaact acgggctgct      660
gtactgcttc agaaaggaca tggacaaggt ggagaccttc ctgaggatcg tgcagtgcag      720
```

```
aagcgtggag ggcagctgcg gcttcagctc cagcagcaag gcccctcccc cgagcctgcc    780
ctccccaagc aggctgcctg ggccctccga cacaccaatc ctgccacaga gcagctcctc    840
taaggcccct cctccatccc tgccatccc ctccggctg cctggcccct ctgacacccc      900
tatcctgcct cagtgatgaa ggtctggatg cggccgc                             937
```

<210> SEQ ID NO 46
<211> LENGTH: 889
<212> TYPE: DNA
<213> ORGANISM: Homo sapiens

<400> SEQUENCE: 46

```
tctagaggac atggccaccg gcagcaggac cagcctgctg ctggccttcg gcctgctgtg     60
cctgccatgg ctgcaggagg gcagcgccag ctcttcttct aaggctccac ccccgagcct   120
gcccttcccc accatccccc tgagcaggct gttcgacaac gccatgctga gggctcacag   180
gctgcaccag ctggcctttg acacctacca ggagttcgag gaagcctaca tccccaagga   240
gcagaagtac agcttcctgc agaaccccca gacctccctg tgcttcagcg agagcatccc   300 caccccagc aacagagagg agacccagca gaagagcaac ctggagctgc tgaggatctc    360
cctgctgctg atccagagct ggctggagcc cgtgcagttc ctgagaagcg tgttcgccaa   420 cagcctggt tacggcgcca gcgacagcaa cgtgtacgac ctgctgaagg acctggagga   480
gggcatccag accctgatgg gccggctgga ggacggcagc cccaggaccg ccagatctt   540 caagcagacc tacagcaagt cgacaccaa cagccacaac gacgacgccc tgctgaagaa   600
ctacgggctg ctgtactgct tcagaaagga catggacaag gtggagacct tcctgaggat   660
cgtgcagtgc agaagcgtgg agggcagctg cggcttcagc tccagcagca aggcccctcc   720
cccgagcctg ccctccccaa gcaggctgcc tgggccctcc gacacaccaa tcctgccaca   780
gagcagctcc tctaaggccc ctcctccatc cctgccatcc cctcccggc tgcctggccc   840 ctctgacacc cctatcctgc ctcagtgatg aaggtctgga tgcggccgc               889
```

<210> SEQ ID NO 47
<211> LENGTH: 217
<212> TYPE: PRT
<213> ORGANISM: Homo sapiens

<400> SEQUENCE: 47

```
Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr Ile Pro Leu
            20                  25                  30

Ser Arg Leu Phe Asp Asn Ala Met Leu Arg Ala His Arg Leu His Gln
        35                  40                  45

Leu Ala Phe Asp Thr Tyr Gln Glu Phe Glu Glu Ala Tyr Ile Pro Lys
    50                  55                  60

Glu Gln Lys Tyr Ser Phe Leu Gln Asn Pro Gln Thr Ser Leu Cys Phe
65                  70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
            100                 105                 110

Leu Glu Pro Val Gln Phe Leu Arg Ser Val Phe Ala Asn Ser Leu Val
        115                 120                 125

Tyr Gly Ala Ser Asp Ser Asn Val Tyr Asp Leu Leu Lys Asp Leu Glu
    130                 135                 140
```

```
Glu Gly Ile Gln Thr Leu Met Gly Arg Leu Glu Asp Gly Ser Pro Arg
145                 150                 155                 160

Thr Gly Gln Ile Phe Lys Gln Thr Tyr Ser Lys Phe Asp Thr Asn Ser
                165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215
```